United States Patent
Ju et al.

(10) Patent No.: US 11,584,932 B2
(45) Date of Patent: Feb. 21, 2023

(54) 5-HALOURACIL-MODIFIED MICRORNAS AND THEIR USE IN THE TREATMENT OF CANCER

(71) Applicant: The Research Foundation for The State University of New York, Albany, NY (US)

(72) Inventors: Jingfang Ju, East Setauket, NY (US); Andrew Fesler, Sound Beach, NY (US)

(73) Assignee: The Research Foundation for The State University of New York, Albany, NY (US)

(*) Notice: Subject to any disclaimer, the term of this patent is extended or adjusted under 35 U.S.C. 154(b) by 0 days.

(21) Appl. No.: 16/176,137

(22) Filed: Oct. 31, 2018

(65) Prior Publication Data

US 2019/0062754 A1   Feb. 28, 2019

Related U.S. Application Data

(63) Continuation-in-part of application No. PCT/US2017/059011, filed on Oct. 30, 2017.

(60) Provisional application No. 62/464,491, filed on Feb. 28, 2017, provisional application No. 62/422,298, filed on Nov. 15, 2016, provisional application No. 62/415,740, filed on Nov. 1, 2016.

(51) Int. Cl.
| | |
|---|---|
| *A61K 48/00* | (2006.01) |
| *C07H 21/02* | (2006.01) |
| *C12N 15/113* | (2010.01) |
| *A61P 35/00* | (2006.01) |
| *A61K 31/712* | (2006.01) |
| *A61K 45/06* | (2006.01) |

(52) U.S. Cl.
CPC ........ *C12N 15/1135* (2013.01); *A61K 31/712* (2013.01); *A61K 45/06* (2013.01); *A61K 48/00* (2013.01); *A61P 35/00* (2018.01); *C07H 21/02* (2013.01); *C12N 2310/14* (2013.01); *C12N 2310/141* (2013.01); *C12N 2310/335* (2013.01); *C12N 2310/3533* (2013.01)

(58) Field of Classification Search
CPC .............. C12N 2310/11; C12N 15/115; C12N 2310/141; C12N 2310/14; C12N 15/113
See application file for complete search history.

(56) References Cited

U.S. PATENT DOCUMENTS

| | | | |
|---|---|---|---|
| 8,748,098 B2 | 6/2014 | Hernando et al. | |
| 9,238,838 B2 | 1/2016 | Markel et al. | |
| 9,255,267 B2 | 2/2016 | Mendell et al. | |
| 10,087,443 B2 * | 10/2018 | Schaefer | C12N 15/113 |
| 2005/0261217 A1 | 11/2005 | Dobie et al. | |
| 2005/0261218 A1 | 11/2005 | Esau et al. | |
| 2007/0072204 A1 | 3/2007 | Hannon et al. | |
| 2007/0259349 A1 | 11/2007 | Bentwich et al. | |
| 2007/0259350 A1 | 11/2007 | Bentwich et al. | |
| 2007/0259352 A1 | 11/2007 | Bentwich et al. | |
| 2008/0076674 A1 | 3/2008 | Litman et al. | |
| 2008/0182237 A1 | 7/2008 | Bentwich et al. | |
| 2009/0136957 A1 | 5/2009 | Ivanovska et al. | |
| 2009/0137504 A1 | 5/2009 | Echwald et al. | |
| 2009/0253780 A1 | 10/2009 | Takeshita et al. | |
| 2010/0105760 A1 | 4/2010 | Collard et al. | |
| 2010/0113284 A1 | 5/2010 | Aristarkhov et al. | |
| 2010/0113560 A1 | 5/2010 | Lieberman et al. | |
| 2010/0227909 A1 | 9/2010 | Cleary et al. | |
| 2010/0279292 A1 | 11/2010 | Marsh et al. | |
| 2010/0286234 A1 | 11/2010 | Elmen et al. | |
| 2010/0311815 A1 | 12/2010 | Chinnaiyan et al. | |
| 2011/0071215 A1 | 3/2011 | Pass et al. | |
| 2011/0118337 A1 | 5/2011 | Chau et al. | |
| 2011/0166200 A1 | 7/2011 | Zhang et al. | |
| 2011/0166201 A1 | 7/2011 | Ju et al. | |
| 2011/0172293 A1 | 7/2011 | Fish et al. | |
| 2011/0263514 A1 | 10/2011 | Rana | |
| 2011/0301226 A1 | 12/2011 | Mendell et al. | |
| 2012/0087992 A1 | 4/2012 | Ju et al. | |
| 2012/0093789 A1 | 4/2012 | Srivastava et al. | |

(Continued)

FOREIGN PATENT DOCUMENTS

| | | |
|---|---|---|
| CN | 113573736 A | 10/2021 |
| EP | 2090665 A2 | 8/2009 |

(Continued)

OTHER PUBLICATIONS

Yu et al. (Gene, 532, 2013, 87-93).*

(Continued)

*Primary Examiner* — Amy H Bowman
(74) *Attorney, Agent, or Firm* — Scully, Scott, Murphy & Presser, P.C.

(57) ABSTRACT

The present disclosure provides nucleic acid compositions that incorporate one or more halouracil molecules. More specifically, the present disclosure reveals that the replacement of uracil nucleotides within a microRNA nucleotide sequence with a 5-halouracil increases the ability of the micro-RNA to inhibit cancer progression and tumorigenesis. As such, the present disclosure provides various nucleic acid (e.g., microRNA) compositions having 5-halouracil molecules incorporated in their nucleic acid sequences and methods for using the same. The present disclosure further provides pharmaceutical compositions comprising the modified nucleic acid compositions, and methods for treating cancers using the same.

7 Claims, 26 Drawing Sheets
(11 of 26 Drawing Sheet(s) Filed in Color)
Specification includes a Sequence Listing.

(56) References Cited

U.S. PATENT DOCUMENTS

| | | |
|---|---|---|
| 2012/0177599 A1 | 7/2012 | Pass et al. |
| 2012/0184603 A1 | 7/2012 | Litman et al. |
| 2012/0202981 A1 | 8/2012 | Lee et al. |
| 2012/0207723 A1 | 8/2012 | He et al. |
| 2012/0238618 A1 | 9/2012 | Elmén et al. |
| 2012/0264131 A1 | 10/2012 | Goel et al. |
| 2012/0322743 A1 | 12/2012 | Hernando et al. |
| 2013/0085077 A1 | 4/2013 | Croce et al. |
| 2013/0109628 A1 | 5/2013 | Wang et al. |
| 2013/0123138 A1 | 5/2013 | Pass et al. |
| 2014/0088300 A1 | 3/2014 | Schmitz, Sr. et al. |
| 2014/0256789 A1 | 9/2014 | Oren et al. |
| 2014/0336241 A1 | 11/2014 | Chajut et al. |
| 2014/0363469 A1* | 12/2014 | Meyers .............. A61K 39/245 424/231.1 |
| 2015/0087607 A1 | 3/2015 | Marcusson et al. |
| 2015/0133525 A1 | 5/2015 | Collard et al. |
| 2015/0159159 A1 | 6/2015 | Anderson et al. |
| 2015/0167007 A1 | 6/2015 | Collard et al. |
| 2015/0225725 A1 | 8/2015 | Collard et al. |
| 2015/0337305 A1* | 11/2015 | Bennett .............. C12N 15/111 514/44 A |
| 2015/0337332 A1* | 11/2015 | Ruohoa-Baker ......... C12N 9/22 514/44 R |
| 2015/0376711 A1* | 12/2015 | Michot .............. C12Q 1/6886 435/6.11 |
| 2016/0002640 A1 | 1/2016 | Collard et al. |
| 2016/0010092 A1 | 1/2016 | Collard et al. |
| 2016/0017331 A1 | 1/2016 | Chung et al. |
| 2016/0090636 A1 | 3/2016 | Ju et al. |
| 2016/0312301 A1 | 10/2016 | Lee et al. |
| 2016/0376598 A1 | 12/2016 | Lee et al. |
| 2017/0015999 A1 | 1/2017 | Yerushalmi |
| 2017/0081666 A1* | 3/2017 | Yao .................. A61K 31/7088 |
| 2017/0182177 A1 | 6/2017 | Rana |
| 2017/0211074 A1 | 7/2017 | Chen et al. |
| 2018/0066260 A1 | 3/2018 | Collard et al. |
| 2018/0207191 A1 | 7/2018 | Lancaster et al. |
| 2018/0221393 A1 | 8/2018 | Peled et al. |
| 2018/0320175 A1 | 11/2018 | Lee et al. |
| 2019/0062754 A1 | 2/2019 | Ju et al. |
| 2019/0112665 A1 | 4/2019 | Hoshen et al. |
| 2019/0247418 A1 | 8/2019 | Pavel et al. |
| 2019/0330632 A1 | 10/2019 | Anand et al. |
| 2020/0140859 A1 | 5/2020 | Pandolfi et al. |
| 2020/0354719 A1 | 11/2020 | Ju et al. |
| 2021/0324383 A1 | 10/2021 | Jaffee et al. |
| 2022/0090076 A1 | 3/2022 | Ju et al. |

FOREIGN PATENT DOCUMENTS

| | | | |
|---|---|---|---|
| EP | 2152722 A2 | 2/2010 | |
| EP | 2370582 A2 | 10/2011 | |
| EP | 2296669 B1 | 3/2012 | |
| EP | 2471956 A1 | 7/2012 | |
| EP | 1978986 B1 | 8/2013 | |
| EP | 2183393 B1 | 6/2014 | |
| EP | 2569432 B1 | 11/2017 | |
| EP | 2113567 B1 | 4/2019 | |
| EP | 3736022 A2 | 11/2020 | |
| EP | 3800256 A1 | 4/2021 | |
| JP | 2008519606 A | 6/2008 | |
| JP | 2009521952 A | 6/2009 | |
| JP | 2010-504349 A | 2/2010 | |
| JP | 2010504350 A | 2/2010 | |
| JP | 2012-532123 A | 12/2012 | |
| JP | 5198430 B2 | 5/2013 | |
| JP | 2013-166766 A | 8/2013 | |
| JP | 5535076 B2 | 7/2014 | |
| JP | 2015504847 A | 2/2015 | |
| JP | 2015518710 A | 7/2015 | |
| JP | 2015518711 A | 7/2015 | |
| JP | 2015518712 A | 7/2015 | |
| JP | 2015518713 A | 7/2015 | |
| JP | 2015518714 A | 7/2015 | |
| JP | 2015519057 A | 7/2015 | |
| JP | 2015523853 A | 8/2015 | |
| JP | 2015523854 A | 8/2015 | |
| JP | 2015523855 A | 8/2015 | |
| JP | 5841024 B2 | 1/2016 | |
| JP | 2016521556 A | 7/2016 | |
| JP | 5971948 B2 | 8/2016 | |
| JP | 6099868 B2 | 3/2017 | |
| JP | 2017511694 A | 4/2017 | |
| JP | 6704883 B2 | 6/2020 | |
| JP | 6738841 B2 | 8/2020 | |
| JP | 7130639 B2 | 9/2022 | |
| KR | 101343616 B1 | 12/2013 | |
| KR | 101596166 B1 | 2/2016 | |
| KR | 101838308 B1 | 3/2018 | |
| KR | 101853508 B1 | 6/2018 | |
| KR | 101857090 B1 | 6/2018 | |
| KR | 20210139237 A | 11/2021 | |
| WO | 96/41809 A1 | 12/1996 | |
| WO | WO 03/029459 A2 * | 4/2003 | ......... C12N 2310/11 |
| WO | 2006128245 A1 | 12/2006 | |
| WO | 2006133022 A2 | 2/2007 | |
| WO | 2007016548 A2 | 2/2007 | |
| WO | 2007033023 A2 | 3/2007 | |
| WO | 2007109236 A2 | 9/2007 | |
| WO | 2008008430 A2 | 1/2008 | |
| WO | 2008/036718 A2 | 3/2008 | |
| WO | 2008095096 A2 | 10/2008 | |
| WO | WO 2009/012468 A2 * | 1/2009 | ......... C12N 2310/11 |
| WO | WO 2009/036236 A1 * | 3/2009 | ........... C12N 15/115 |
| WO | WO 2009/036332 A1 * | 3/2009 | ........... C12N 15/111 |
| WO | 2009049129 A1 | 4/2009 | |
| WO | 2009075787 A1 | 6/2009 | |
| WO | 2009126726 A1 | 10/2009 | |
| WO | 2009154835 A2 | 12/2009 | |
| WO | 2010006111 A2 | 1/2010 | |
| WO | 2010023658 A2 | 3/2010 | |
| WO | 2010065156 A1 | 6/2010 | |
| WO | WO 2010/115050 A2 * | 10/2010 | ........... C12N 15/115 |
| WO | 2010127195 A2 | 11/2010 | |
| WO | WO 2010/126370 A2 * | 11/2010 | ........... C12N 15/113 |
| WO | 2011/002200 A2 | 1/2011 | |
| WO | 2011014980 A1 | 2/2011 | |
| WO | 2011024157 A1 | 3/2011 | |
| WO | WO 2011/108930 A1 * | 9/2011 | ........... C12N 15/111 |
| WO | 2011128886 A1 | 10/2011 | |
| WO | 2011146674 A2 | 11/2011 | |
| WO | 2011157294 A1 | 12/2011 | |
| WO | 2012009347 A2 | 1/2012 | |
| WO | 2012009508 A2 | 1/2012 | |
| WO | 2012082821 A2 | 6/2012 | |
| WO | WO 2012/092485 A1 * | 7/2012 | ......... C12N 2310/11 |
| WO | WO 2012/096573 A1 * | 7/2012 | ......... C12N 2310/11 |
| WO | 2013/056216 A1 | 4/2013 | |
| WO | WO 2013/158046 A1 * | 10/2013 | ........... C12N 15/111 |
| WO | 2014/100252 A | 6/2014 | |
| WO | WO 2014/201417 A1 * | 12/2014 | ......... C12N 2310/11 |
| WO | 2018/085198 A1 | 5/2018 | |
| WO | 2019245135 A1 | 12/2019 | |
| WO | 2020061397 A1 | 3/2020 | |
| WO | 2020102142 A1 | 5/2020 | |
| WO | 2020154207 A1 | 7/2020 | |
| WO | 2020186124 A1 | 9/2020 | |
| WO | 2021097437 A1 | 5/2021 | |

OTHER PUBLICATIONS

Zhang et al. (Journal of Hematology & Oncology, 2010, 3:46, pp. 1-9).*

Elliott et al. (Journal of Molecular and Cellular Cardiology, 62, 2013, 1-7).*

NCBI Reference Sequence No. NP_001230005.1 (3 pages) (Oct. 21, 2018).

NCBI Reference Sequence No. NG_009361.1 (48 pages) (Apr. 13, 2018).

NCBI Reference Sequence No. NM_000633.2 (7 pages) (Oct. 21, 2018).

(56) References Cited

OTHER PUBLICATIONS

NCBI Reference Sequence No. NP_000624.2 (4 pages) (Oct. 21, 2018).
NCBI Reference Sequence No. NM_000657.2 (4 pages) (Oct. 21, 2018).
NCBI Reference Sequence No. NP_000648.2 (3 pages) (Oct. 21, 2018).
NCBI Reference Sequence No. NG_028255.1 (14 pages) (Oct. 23, 2018).
NCBI Reference Sequence No. NM_001071.2 (4 pages) (Aug. 21, 2017).
NCBI Reference Sequence No. NP_001062.1 (3 pages) (Oct. 22, 2018).
NCBI Reference Sequence No. NM_001243076.2 (5 pages) (Oct. 21, 2018).
Accession No. MIMAT0004557 (1 page) (2018).
Accession No. MI0000737 (2 pages) (2018).
Accession No. MIMAT0001620 (1 page) (2018).
Accession No. MIMAT000682 (2 pages) (2018).
Accession No. MI0000342 (2 pages) (2018).
Accession No. MIMAT00004571 (2 pages) (2018).
Accession No. MIMAT0000318 (2 pages) (2018).
Accession No. MIMAT0004657 (2 pages) (2018).
Accession No. MIMAT000617 (2 pages) (2018).
Accession No. MIMAT0000437 (2 pages) (2018).
Iwaizumi M. et al., "DNA Mismatch Repair Proficiency Executing 5-Fluorouracil Cytotoxicity in Colorectal Cancer Cells", Cancer Biology & Therapy 12(8):756-764 (Oct. 15, 2011).
Karaayvaz M. et al., "miR-129 Promotes Apoptosis and Enhances Chemosensitivity to 5-Fluorouracil in Colorectal Cancer", Cell Death and Disease 4:e659 (2013).
Pettersen H.S. et al., "UNG-Initiated Base Excision Repair is the Major Repair Route for 5-Fluorouracil in DAN, But 5-Fluorouracil Cytotoxicity Depends Mainly on RNA Incorporation", Nucleic Acids Research 39(19):8430-8444 (Jul. 2011).
International Search Report and Written Opinion dated Feb. 6, 2018 received in International Patent Application No. PCT/US2017/059011.
Acunzo M. et al., "Downregulation of miR-15a and miR-16-1 at 13q14 in Chronic Lymphocytic Leukemia", Clinical Chemistry 62(4):655-656 (2016).
Altuvia Y. et al., "Clustering and Conservation Patterns of Human microRNAs", Nucleic Acids Research 33(8):2697-2706 (2005).
Ambros V., "The Functions of Animal microRNAs", Nature 431:350-355 (Sep. 16, 2004).
Aqeilan Ri et al., "miR-15a and miR-16-1 in Cancer; Discovery, Function and Future Perspectives", Cell Death and Differentiation 17:215-220 (2010).
Bartel D.P., "MicroRNAs: Target Recognition and Regulatory Functions", Cell 136(2):215-233 (Jan. 23, 2009).
Bartel DP, "MicroRNAs: Genomics, Biogenesis, Mechanism, and Function", Cell 116:281-297 (Jan. 23, 2004).
Beaucage S.L. et al., "Deoxynucleoside Phosphoramidites—A New Class of Key Intermediates for Deoxypolynucleotides Synthesis", Tetrahedron Letters 22(20):1856-1862 (1981).
Carreras C.W. et al., "The Catalytic Mechanism and Structure of Thymidylate Synthase", Annu. Rev. Biochem. 64:721-762 (1995).
Crose C.M., "Causes and Consequences of microRNA Dysregulation in Cancer", Nature Reviews Genetics 10:704-714 (Oct. 2009).
Dunham CM et al., "Recombinant RNA Expression", Nature Methods 4(7):547-548 (Jul. 2007).
Gottesman M.M. et al., "Multidrug Resistance in Cancer: Role of ATP-Dependent Transporters", Nature Reviews—Cancer 2:48-58 (Jan. 2002).
Kasashima K. et al., "Altered Expression Profiles of MicroRNAs During TPA-Induced Differentiation of HL-60 Cells", Biochemical and Biophysical Research Communications 322:403-410 (2004).
Lagos-Quintana M. et al., "New microRNAs from Mouse and Human", RNA 9(2):175-179 (2003).
Landgraf P. et al., "A Mammalian microRNA Expression Atlas Based on Small RNA Library Sequencing", Cell 129:1401-1414 (Jun. 29, 2007).
Li J. et al., "The Emerging Role of miR-506 in Cancer", Oncotarget 7(38):62778-62788 (2016).
Li J. et al., "Downregulated miR-506 Expression Facilitates Pancreatic Cancer Progression and Chemoresistance Via SPHK1/Akt/NF-κB Signaling", Oncogene 35:5501-5514 (2016).
Lui W-O et al., "Patterns of Known and Novel Small RNAs in Human Cervical Cancer", Cancer Research 67(13):6031-6043 (Jul. 1, 2007).
Maitra A. et al., "Pancreatic Cancer", Annual Review of Pathology: Mechanisms of Disease 3:157-188 (2008).
Matteucci M.D. et al., "Synthesis of Deoxyoligonucleotides on a Polymer Support", J. Am. Chem. Soc. 103:3185-3191 (1981).
Oettle H. et al., "Adjuvant Chemotherapy With Gemcitabine and Long-Term Outcomes Among Patients With Resected Pancreatic Cancer", JAMA 310(14):1473-1481 (Oct. 9, 2013).
Scaringe S.A. et al., "Novel RNA Synthesis Method Using 5'-O-Silyl-2'-O-Orthoester Protecting Groups", J. Am. Chem. Soc. 120(45):11820-11821 (1998).
Siegel R.L. et al., "Cancer Statistics", Cancer J. Clin. 65(1):5-29 (Jan./Feb. 2015).
Song B. et al., "Molecular Mechanism of Chemoresistance by miR-215 in Osteosarcoma and Colon Cancer Cells", Molecular Cancer 9(96):1476-1498 (2010).
Song B. et al., "miR-192 Regulates Dihydrofolate Reductase and Cellular Proliferation Through the p53-microRNA Circuit", Clin. Cancer Res. 14(24):8080-8086 (Dec. 15, 2008).
Wu J. et al., "miR-129 Regulates Cell Proliferation by Downregulating Cdk6 Expression", Cell Cycle 9(9):1809-1818 (May 1, 2010).
Zhai H. et al., "Inhibition of Colorectal Cancer Stem Cell Survival and Invasive Potential by Has-miR-140-5p Mediated Suppression of Smad2 and Autophagy", Oncotarget 6(23):19735-19746 (2015).
Zhai H. et al., "Inhibition of Autophagy and Tumor Growth in Colon Cancer by miR-502", Oncogene 32(12):1570-1579 (2013).
Accession No. MI0000252 (2 pages) (2018).
Accession No. MIMAT0000242 (2 pages) (2018).
Accession No. MIMAT0004548 (1 page) (2018).
Accession No. MI0000069 (3 pages) (2018).
Accession No. MI0000068 (2 pages) (2018).
Accession No. MIMAT0004488 (2 pages) (2018).
Accession No. MI0000456 (2 pages) (2018).
Accession No. MIMAT0000431 (2 pages) (2018).
NCBI Reference Sequence No. NT_010498.16 (6 pages) (Mar. 26, 2018).
Accession No. MIMAT0004597 (2 pages) (2018).
Accession No. MI0000234 (2 pages) (2018).
Accession No. MI0000291 (2 pages) (2018).
Accession No. MIMAT0000222 (2 pages) (2018).
Accession No. MIMAT0000272 (2 pages) (2018).
Accession No. MIMAT0004543 (1 page) (20180, 2018.
Accession No. MIMAT0026476 (1 page) (2018).
Accession No. MI0003186 (2 pages) (2018).
Accession No. MIMAT0002873 (1 page) (2018).
Accession No. MIMAT0004775 (1 page) (2018).
Accession No. MI0003193 (2 pages) (2018).
Accession No. MIMAT0002878 (1 page) (2018).
Accession No. MI0000268 (2 pages) (2018).
Accession No. MIMAT0000255 (2 pages) (2018).
Accession No. MIMAT0004601 (1 page) (2018).
Accession No. MI0000488 (2 pages) (2018).
Accession No. MI0000732 (2 pages) (2018).
Accession No. MIMAT0000460 (2 pages) (2018).
Accession No. MIMAT0004671 (2 pages) (2018).
Accession No. MI0000060 (3 pages) (2018).
Accession No. MIMAT0000062 (2 pages) (2018).
Accession No. MIMAT0004481 (2 pages) (2018).
NCBI Reference Sequence No. NG_029591.1 (25 pages) (Oct. 21, 2017).
Wu N. et al., "Development of Novel miR-129 Mimics With Enhanced Efficacy to Eliminate Chemoresistant Colon Cancer Stem Cells", Oncotarget 9(10):8887-8897 (2018).

(56) References Cited

OTHER PUBLICATIONS

Invitation to Pay Additional Fees dated Dec. 31, 2019 received in International Application No. PCT/US19/58706.
Fesler A. et al., "Development of 5-FU Modified Tumor Suppressor miRNAs as a Platform for miRNA Based Cancer Therapeutics", Abstract 4403, in Proceedings of the American Association for Cancer Research Annual Meeting, AACR; Cancer Research 78(13 Suppl) (Jul. 2018).
International Search Report and Written Opinion dated Mar. 5, 2020 received in International Application No. PCT/US19/58706.
Chiu Y-L et al., "siRNA Function in RNAi: A Chemical Modification Analysis", RNA 9(9):1034-1048 (Jan. 1, 2003).
Lam J KW et al., "siRNA Versus miRNA as Therapeutics for Gene Silencing", Molecular Therapy-Nucleic Acids 4:e252 (Jan. 1, 2015).
Watts J.K. et al., "Chemically Modified siRNA: Tools and Applications", Drug Discovery Today 13(19/20):842-855 (Oct. 1, 2008).
Wu S-Y et al., "Development of Modified siRNA Molecules Incorporating 5-Fluoro-2-Deoxyuridine Residues to Enhance Cytotoxicity", Nucleic Acids Research 41(8):4650-4659 (Apr. 1, 2013).
Supplementary Partial European Search Report dated May 29, 2020 received in European Application No. 17 86 7742.3.
Extended Supplementary European Search Report dated Sep. 3, 2020 received in European Application No. 17 86 7742.3.
Chen Z. et al., "miR-124 and miR-506 Inhibit Colorectal Cancer Progression by Targeting DNMT3B and DNMT1", Oncotarget 6(35):38139-38150 (2015).
Yu X. et al., "Growth Inhibitory Effects of Three miR-129 Family Members on Gastric Cancer" Gene 535:87-93 (2013).
Japanese Notice of Reasons for Rejection dated Jul. 26, 2021 received in Japanese Application No. 2019-523008, together with an English-language translation.
Brazilian Search Report dated Sep. 15, 2021 received in Brazilian Application No. BR112019008810-5, together with an English-language translation.
Peng F. et al., "Direct Targeting of SUZ12/ROCK2 by miR-200b/c Inhibits Cholangiocarcinoma Tumourigenesis and Metastasis", British Journal of Cancer 109:3092-3104 (2013).
Invitation to Pay Additional Fees dated Oct. 6, 2021 received in International Application No. PCT/US21/38796.
Mexican Office Action dated Mar. 29, 2022 received in Mexican Application No. MX/a/2019/005101, together with an English-language translation.
Chinese Office Action dated Jun. 1, 2022 received in Chinese Patent Application No. 201780081456.7, together with an English-language translation.
Japanese Notice of Reasons for Rejection dated Feb. 7, 2022 received in Japanese Application No. 2019-523008, together with an English-language translation.
Korean Office Action dated May 10, 2022 received in Korean Patent Application No. 10-2019-7015788, together with an English-language translation.

\* cited by examiner

5' CU$^F$U$^F$U$^F$U$^F$U$^F$GCGGU$^F$CU$^F$GGGCU$^F$U$^F$GC 3'

FIG. 1A

5' CUUUUUGCGGU$^F$CU$^F$GGGCU$^F$U$^F$GC 3'

FIG. 1B

5' U$^F$AGCAGCACAU$^F$AAU$^F$GGU$^F$U$^F$U$^F$GU$^F$G 3'

FIG. 1C

5' UAGCAGCACAU$^F$AAU$^F$GGU$^F$U$^F$U$^F$GU$^F$G 3'

FIG. 1D

5' CAGU$^F$GGUUUUACCCU$^F$AUGGU$^F$AG 3'

FIG. 1E

5' CAGU$^F$GGU$^F$U$^F$U$^F$U$^F$ACCCU$^F$AU$^F$GGU$^F$AG 3'

FIG. 1F

5' CU$^F$GACCU$^F$AU$^F$GAAU$^F$U$^F$GACAGCC 3'

FIG. 1G

5' AU^FCCU^FU^FGCUAU^FCU^FGGGU^FGCU^FA 3'

FIG. 1H

5' U^FAU^FU^FCAGGAAGGU^FGU^FU^FACU^FU^FAA 3'

FIG. 1I

5' U^FGGCAGU^FGU^FCU^FU^FAGCU^FGGU^FU^FGU^F 3'

FIG. 1J

3' U^FAACACU^FGU^FCU^FGGU^FAACGAU^FGU^F 5'

FIG. 1K

3' U^FAAU^FACU^FGCCU^FGGU^FAAU^FGAU^FGA 5'

FIG. 1L

3' U^FAAU^FACU^FGCCGGGU^FAAU^FGAU^FGGA 5'

FIG. 1M

5' GU^FCCAGU^FU^FU^FCCCAGGAAU^FCCCU^F 3'

FIG. 1N

5' U$^F$GU$^F$AACAGCAACU$^F$CCAU$^F$GU$^F$GGA 3'

FIG. 1O

5' U$^F$GAGGU$^F$AGU$^F$AGGU$^F$U$^F$GU$^F$AU$^F$AGU$^F$U$^F$ 3'

FIG. 1P

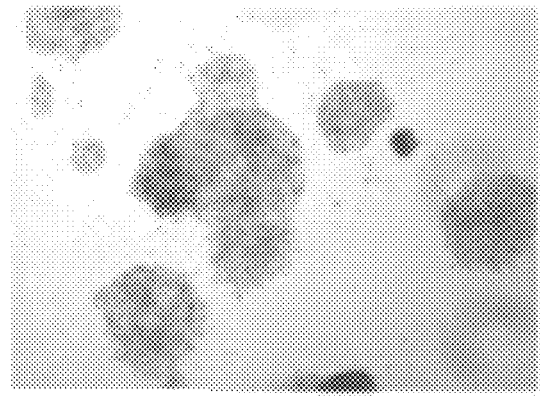
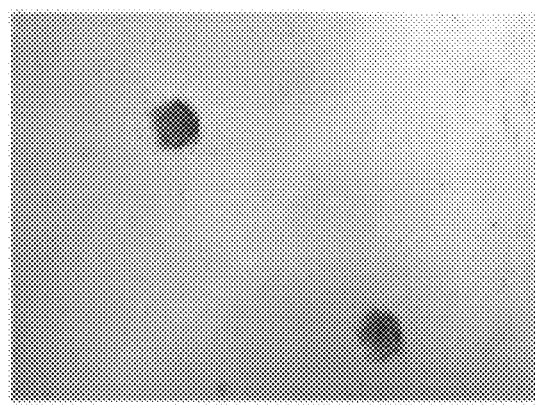
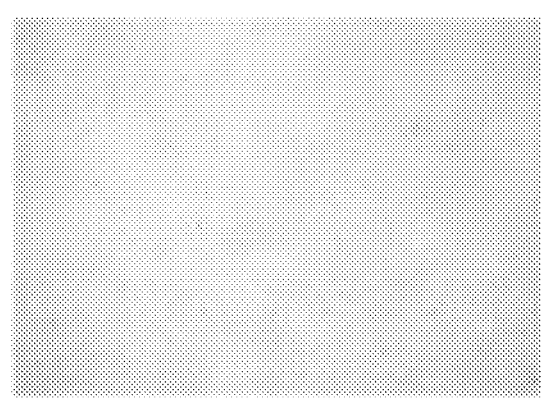
FIG. 10

A

B

C

D

A
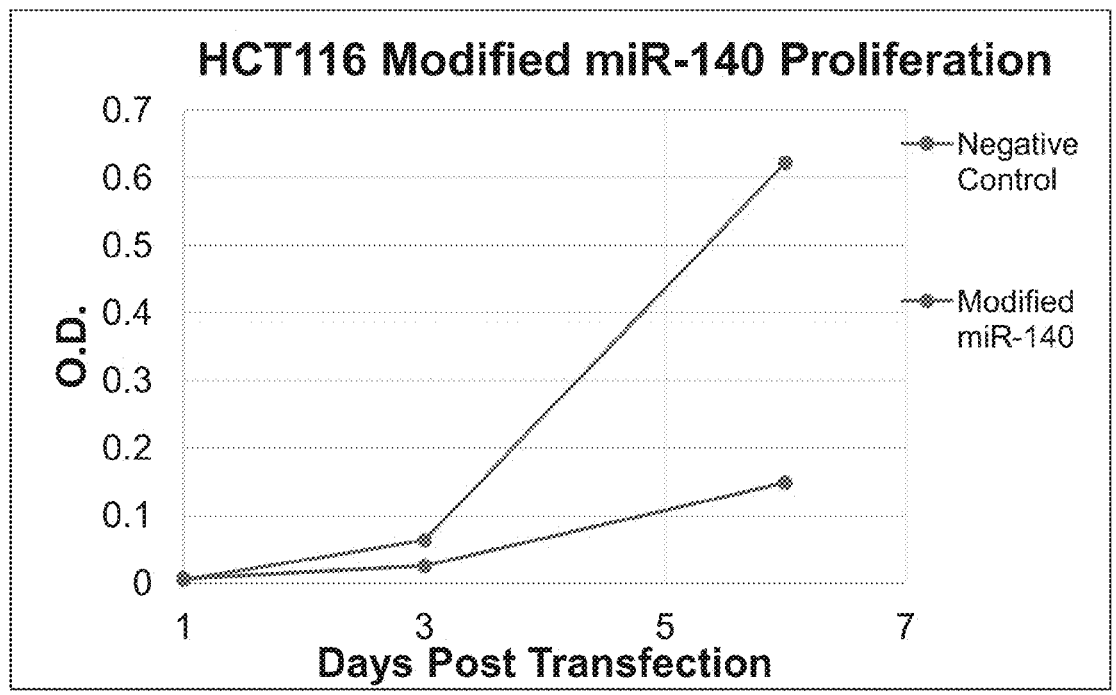
B
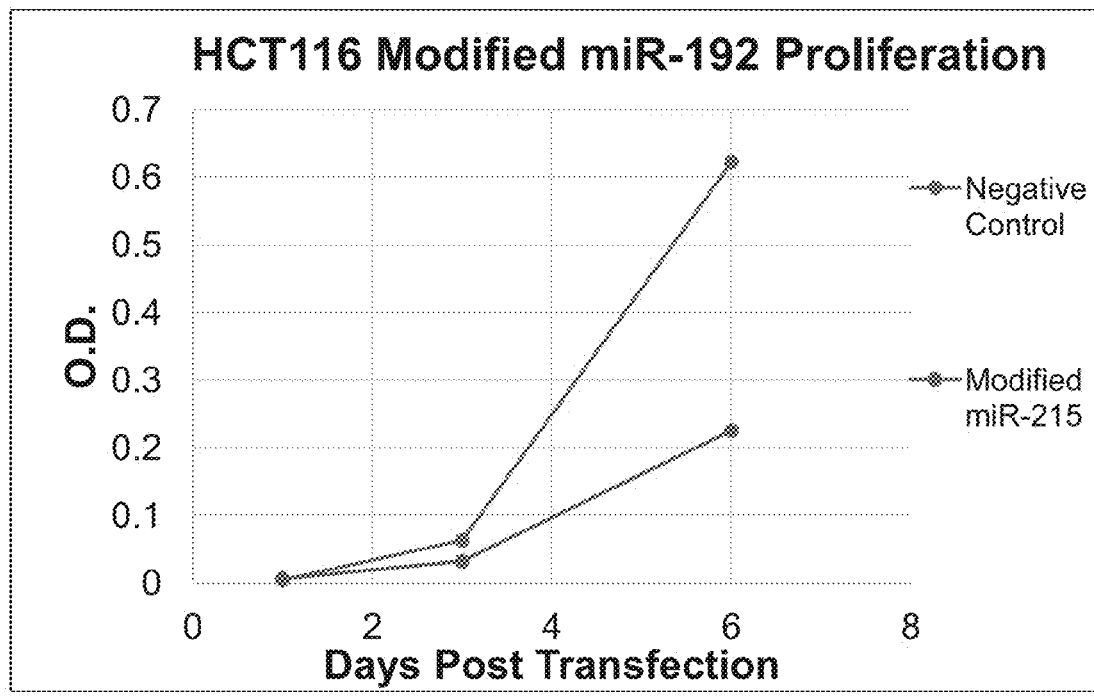
FIGS. 13A-B

A

B

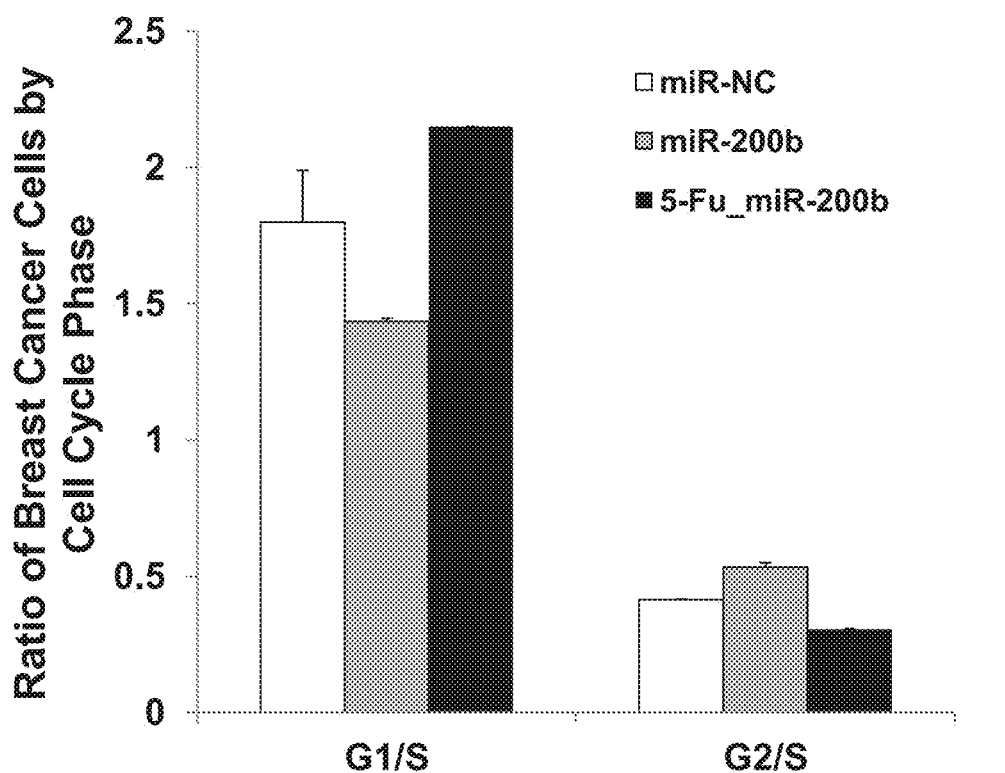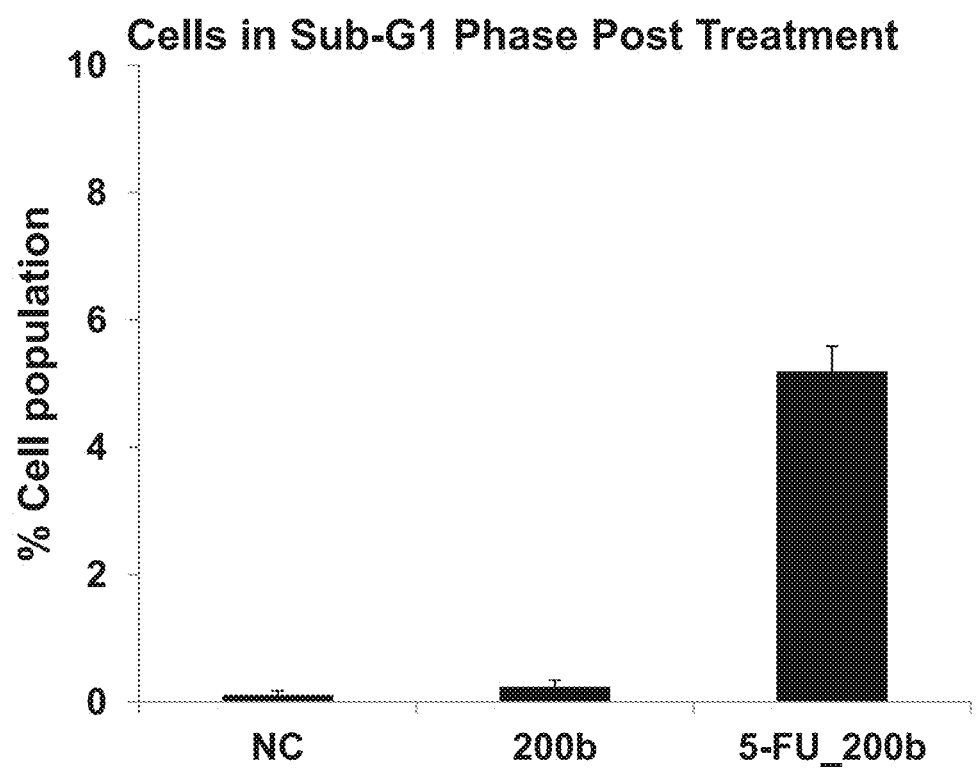
FIG. 16C

A

B

5-HALOURACIL-MODIFIED MICRORNAS AND THEIR USE IN THE TREATMENT OF CANCER

CROSS REFERENCE TO RELATED APPLICATIONS

This application is a continuation in-part of PCT/US2017/059011 filed on Oct. 30, 2017, which claims benefit of U.S. Provisional Application No. 62/464,491, filed Feb. 28, 2017, U.S. Provisional Application No. 62/422,298, filed Nov. 15, 2016, and U.S. Provisional Application No. 62/415,740, filed Nov. 1, 2016, the entire contents of each of which are incorporated herein by reference.

GOVERNMENT SUPPORT

This invention was made with government support under grant numbers HL127522 and CA197098 awarded by the National Institutes of Health. The government has certain rights in the invention.

INCORPORATION BY REFERENCE OF SEQUENCE LISTING

The Sequence Listing in the ASCII text file, named as 050_8992_US_SequenceListing.txt, and submitted to the United States Patent and Trademark Office via EFS-Web, is incorporated herein by reference.

FIELD OF THE DISCLOSURE

The present disclosure is generally directed to nucleic acid compositions that include 5-halouracil. More specifically, the present disclosure provides modified microRNA compositions that contain one or more 5-halouracil compounds and methods for using the same. Furthermore, the instant application provides pharmaceutical compositions that include the inventive nucleic acid compositions and methods for treating cancer using the same.

BACKGROUND

MicroRNAs (miRNAs, miRs) are a class of highly conserved, non-coding small ribonucleic acid (RNA) molecules that mediate translation in a cell or organism by negatively regulating the expression of their target genes and thus causing translational arrest, messenger RNA (mRNA) cleavage or a combination thereof. See Bartel D P. *Cell*. (2009) 136(2):215-33. By targeting multiple transcripts, miRNAs regulate a wide range of biological processes including apoptosis, differentiation and cell proliferation; thus, aberrant microRNA function can lead to cancer (see Ambros V. *Nature*. (2004) 431 pp. 350-355) and as such, miRNAs have recently been identified as biomarkers, oncogenes or tumor suppressors. See, e.g., Croce, C M. *Nat Rev Genet*. (2009) 10 pp. 704-714.

According to the World Health Organization, Cancer is a leading cause of death worldwide, accounting for 8.8 million deaths in 2015. The most common causes of cancer death are cancers of the lung (1.69 million deaths), liver (788,000 deaths), colorectal (774,000 deaths), stomach (i.e., gastric cancer) accounting for 774,000 deaths, and breast (754,000 deaths). See Surveillance, Epidemiology, and End Results Program. SEER Cancer Stat Facts. *National Cancer Institute*. Bethesda, Md. (2018).

Lung cancer is the leading cause of cancer death in both men and women in the United States, with only 18.6% of patients diagnosed with lung cancer surviving beyond 5 years. Surveillance, Epidemiology, and End Results Program. SEER Cancer Stat Facts: Lung and Bronchus Cancer. *National Cancer Institute*. Bethesda, Md. (2018). There are two primary categories of lung cancer: non-small cell lung cancer and small cell lung cancer. Non-small cell lung cancer is further delineated by type of cancer cells present in a tissue. As such, non-small cell lung cancer is broken down into following sub-classes of lung cancer: squamous cell carcinoma (also called epidermoid carcinoma), large cell carcinoma, adenocarcinoma (i.e., cancer that originates in cells lining alveoli), pleomorphic, carcinoid tumor and salivary gland carcinoma. Meanwhile, there are two main types of small cell lung cancer: small cell carcinoma and combined small cell carcinoma. SEER Cancer Stat Facts: Lung and Bronchus Cancer. *National Cancer Institute*. Bethesda, Md. (2018). The most common treatment for non-small cell lung cancers is gemcitabine (2',2'-difluoro 2'deoxycytidine), taxol (e.g., paclitaxel), cisplatin (a DNA cross-linking agent), and combinations thereof. However, many types of antibody-based therapeutics are also used to treat non-small cell lung cancer (e.g., gefitinib, pembrolizumab, alectinib). Small cell lung cancer is commonly treated by methotrexate, doxorubicin hydrochloride, and topotecan based chemotherapeutic agents.

Breast cancer is the second most common cancer in women, with the most common he most common type of breast cancer being ductal carcinoma. Ductal carcinoma begins in the cells of the ducts. In contrast, lobular carcinoma, which is often found in both breasts, originates in the lobes or lobules. Many chemotherapeutic agents are used to treat breast cancer including, but not limited to, cytotoxic drugs such as taxols (paclitaxel, docetaxel) doxorubicin hydrochloride, 5-FU, gemcitabine hydrochloride, methotrexate, and tamoxifen citrate. In addition many antibody-based therapeutic agents are administered to treat various types of breast cancer, such as trastuzumab, olaparib and pertuzumab.

Colorectal cancer (CRC) is the third most common malignancy and the second most common cancer-related cause of death in the United States. See, Hegde S R, et al., *Expert review of gastroenterology & hepatology*. (2008) 2(1) pp. 135-49. There are many chemotherapeutic agents used to treat cancer; however pyrimidine antagonists, such as fluoropyrimidine-based chemotherapeutic agents (e.g., 5-fluorouracil, S-1) are the gold standard for treating colorectal cancer. Pyrimidine antagonists, block the synthesis of pyrimidine containing nucleotides (Cytosine and Thymine in DNA; Cytosine and Uracil in RNA). Because pyrimidine antagonists have similar structures when compared to endogenous nucleotides, they compete with the natural pyrimidines to inhibit crucial enzymatic activity involved in the replication process leading to the prevention of DNA and/or RNA synthesis and inhibition of cell division.

Gastric cancer (i.e., stomach cancer or gastric adenocarcinoma) is the fourth most common cause of cancer-related death in the world, and it remains difficult to cure in Western countries, primarily because most patients present with advanced disease. In the United States, stomach malignancy is currently the 14th most common cancer. American Cancer Society: Cancer Facts and Figures 2018. *American Cancer Society*. Atlanta, Ga. (2018). Gastric cancers typically present in to forms, intestinal adenocarcinomas, which are well differentiated, or diffuse adenocarcinomas that are poorly differentiated and do not form glandular structures. Due to a lack of effective non-invasive treatment options, surgery remains the primary treatment for gastric cancers. However, a combination of 5-fluorouracil (5-FU) and leucovorin can also be administered to gastric cancer patients.

Pancreatic cancer is a deadly cancer that is very difficult to treat. See Siegel, R L et al. *Cancer J. Clin.* (2015) 65 pp. 5-29. Unique aspects of pancreatic cancer include a very low 5 year survival rate of less than 7% (Id.), late presentation, early metastasis and a poor response to chemotherapy and radiation. See Maitra A and Hruban R H, *Annu Rev. Pathol.* (2008) 3 pp. 157-188. To date gemcitabine-based chemotherapy (2',2'-difluoro 2'deoxycytidine) is the gold standard for the treatment of pancreatic cancer, however the effect of therapeutic intervention is limited due to drug resistance. Oettle, H et al. *JAMA* (2013) 310 pp. 1473-1481.

Blood born cancers, i.e., leukemia, are a common form of cancer, which is also very diverse, as evidenced by the number of different types of leukemia. In 2015, there were an estimated 405,815 people living with leukemia in the United States. The primary types of leukemia are: acute lymphocytic leukemia (ACL), acute lymphoblastic leukemia (ALL), acute mylogenous leukemia (AML), chronic lymphocytic leukemia (CLL) and chronic mylogenous leukemia (CML). Noone A M, et al. (eds). SEER Cancer Statistics Review, 1975-2015, *National Cancer Institute*. Bethesda, Md. (2018). Drugs approved for the treatment of leukemia include, for example, doxorubicin hydrochloride, 5-FU, gemcitabine hydrochloride, cytarabine, methotrexate, and tamoxifen citrate, rituximab, ibrutinib, imatinib and dasatinib.

5-fluorouracil (i.e., 5-FU, or more specifically, 5-fluoro-1H-pyrimidine-2,4-dione) is a well known pyrimidine antagonist that is used in many adjuvant chemotherapeutic medicants, such as Carac® cream, Efudex®, Fluoroplex®, and Adrucil®. It is well established that 5-FU targets a critical enzyme, thymidylate synthase (TYMS or TS), which catalyzes the methylation of deoxyuridine monophosphate (dUMP) to deoxythymidine monophosphate (dTMP) an essential step in DNA biosynthesis. Danenberg P. V., Biochim. *Biophys. Acta.* (1977) 473(2):73-92. However, despite the steady improvement of 5-FU-based therapy, the patient response rate to 5-FU-based chemotherapy remains modest, due to the development of drug resistance. Longley D. B, et al., *Apoptosis, Cell Signaling, and Human Diseases*, (2007) p. 263-78.

Nevertheless, the existing cancer therapies are still in their infancy, with many hurdles still waiting to be improved or overcome. For example, it is well known that, although fairly efficacious in treating a variety of cancers, 5-FU possesses substantial toxicity and can elicit a host of adverse side effects. 5-FU, like many cytotoxic chemotherapeutic agents, is administered systemically by IV or injection and non-specifically targets all dividing cells in the subject (including cancer cells). As such, new targeted anti-cancer therapeutics with less toxicity are sought as an alternative to existing cancer therapeutics.

With respect to miRNAs, these compounds are known to be susceptible to enzymatic degradation when administered, which results in poor stabilities. Moreover, tumor cells have been known to circumvent apoptotic pathways by developing resistance to common therapeutic agents, such as 5-FU and gemcitabine. See Gottesman M. M. et al., *Nature Reviews Cancer*, (2002) 2(1):48-58. Thus, there would be a significant benefit in more efficacious, stable, and less toxic medications for the treatment of cancer.

SUMMARY OF THE DISCLOSURE

Without being bound by any one particular theory, the present disclosure is premised on the discovery that the incorporation of 5-halouracil bases within the nucleotide sequences of microRNAs increases microRNA efficacy as an anticancer therapeutic agent, when compared to certain known chemotherapeutic agents alone and/or the native microRNA molecule. The current disclosure demonstrates that nucleic acid compositions (i.e., a microRNA), which incorporate at least one 5-halouracil base have exceptional efficacy as anti-cancer agents. Moreover, the data herein shows that contacting a cell with a modified microRNA composition of the present disclosure regulates cell-cycle progression and reduces tumorigenesis by, for example, reducing cancer cell proliferation and increasing the efficacy of chemotherapeutic agents. Furthermore, it is shown that the modified microRNAs of the present disclosure retain target specificity, can be delivered without the use of harmful and ineffective delivery vehicles (e.g., nanoparticles), and exhibit enhanced potency and stability without abolishing the natural function of the endogenous microRNA. Hence the present disclosure provides novel modified microRNA compositions with enhanced stability and potency, target specificity, and low-toxicity for the treatment of many types of cancer.

Therefore, in one aspect of the present disclosure nucleic acid compositions that include a modified microRNA nucleotide sequence having at least one uracil base (U, U-bases) that has been replaced by a 5-halouracil, such as 5-fluorouracil (5-FU) are described. In certain embodiments, the modified microRNA has more than one, or exactly one uracil that has been replaced by a 5-halouracil. In some embodiments, the modified microRNA nucleotide sequence includes two, three, four, five, six, seven, eight or more uracil bases that have been replaced by a 5-halouracil. In specific embodiments, all of the uracil nucleotide bases of native microRNA have been replaced by a 5-halouracil.

In some embodiments, the 5-halouracil is, for example, 5-fluorouracil, 5-chlorouracil, 5-bromouracil, or 5-iodouracil. In specific embodiments, the 5-halouracil is 5-fluorouracil.

In certain embodiments, the modified microRNA nucleotide sequence includes more than one 5-halouracil whereby each of the 5-halouracils are the same. In other embodiments, the modified microRNA nucleotide sequence includes more than one 5-halouracil whereby each of the 5-halouracils is different. In other embodiments, the modified microRNA nucleotide sequence includes more than two 5-halouracils, whereby the modified microRNA nucleotide sequence includes a combination of different 5-halouracils.

In an exemplary embodiment of the present disclosure, a nucleic acid composition that contains a miR-129 nucleotide sequence that has been modified by replacing at least one of the uracil nucleotide bases with a 5-halouracil is provided. More specifically, the nucleic acid composition contains at least the following native miR-129 nucleotide sequence: CUUUUUGCGGUCUGGGCUUGC [SEQ ID NO. 1], wherein at least one, two, three, four, five, six, seven, eight or all of the uracil bases in the shown nucleic acid sequence or that may be covalently appended to the shown sequence, are replaced by a 5-halouracil.

In a specific embodiment of the present disclosure, the modified microRNA has nucleic acid sequence consisting of CU$^F$U$^F$U$^F$U$^F$U$^F$GCGGU$^F$CU$^F$GGGCU$^F$U$^F$GC [SEQ ID NO. 4], wherein U$^F$ is a halouracil, specifically 5-fluorouracil.

In other embodiments, a seed portion of the native miR-129 nucleotide sequence, GUUUUUGC remains unmodified (i.e., does not include a 5-halouracil) while one or more (or all) of the remaining uracil nucleotide bases in the remainder of the modified miR-129 nucleotide sequence are replaced by an equivalent number of 5-halouracils. In a specific embodiment, the modified miR-129 microRNA of the present disclosure has nucleic acid sequence consisting of CUUUUUGCGGU$^F$CU$^F$GGGCU$^F$U$^F$GC [SEQ ID NO. 5], whereby U$^F$ is a halouracil, specifically 5-fluorouracil.

In some embodiments, the 5-halouracil is, for example, 5-fluorouracil, 5-chlorouracil, 5-bromouracil, or 5-iodouracil. In specific embodiments, the 5-halouracil is 5-fluorouracil.

In another embodiment of the present disclosure, nucleic acid compositions that contain a miR-15a nucleotide sequence that has been modified by replacing at least one of the uracil nucleotide bases with a 5-halouracil, such as 5-fluorouracil (5-FU) are provided. Specifically, the nucleic acid composition contains at least the following native miR-15a nucleotide sequence: UAGCAGCACAUAAUG-GUUUGUG [SEQ ID NO. 2], wherein at least one, two, three, four, five, six or all of the uracil nucleotide bases in the shown sequence, or that may be covalently appended to the shown sequence, are 5-halouracils.

In a specific embodiment of the present disclosure, the modified miR-15a microRNA has nucleic acid sequence consisting of U$^F$AGCAGCACAU$^F$AAU$^F$GGU$^F$U$^F$U$^F$GU$^F$G [SEQ ID NO. 6], wherein U$^F$ is a halouracil, specifically 5-fluorouracil.

In other embodiments, a seed portion of the native miR-15a nucleotide sequence, UAGCAGCA, remains unmodified with a 5-halouracil, while one or more (or all) of the remaining uracil bases in the remainder of the miR-15a nucleotide sequence (non-seed portion) are replaced by a 5-halouracil.

In a specific embodiment, the modified miR-15a microRNA has nucleic acid sequence consisting of UAGCAGCACAU$^F$AAU$^F$GGU$^F$U$^F$U$^F$GU$^F$G [SEQ ID NO. 7], wherein U$^F$ is a halouracil, specifically 5-fluorouracil.

In another exemplary embodiment, the present disclosure is directed to nucleic acid compositions that include a miR-140 nucleotide sequence that has been modified. In some embodiments, the native miR-140 nucleotide sequence has been modified by replacing at least one of the U bases with a 5-halouracil. More specifically, the nucleic acid composition contains at least the following native miR-140 nucleotide sequence: CAGUGGUUUUACCCUAUG-GUAG [SEQ ID NO. 8], wherein at least one, two, three, four, five, six, seven or all of the uracil bases in the shown nucleic acid sequence are replaced by a 5-halouracil.

In one set of embodiments, precisely one of the U bases in the native miR-140 nucleic acid sequence is a 5-halouracil. In a second set of embodiments, precisely or at least two U bases in the native miR-140 nucleotide sequence are replaced by 5-halouracils. In another set of embodiments, precisely or at least three U bases in the miR-140 nucleotide sequence are 5-halouracils. In other embodiments, precisely or at least four U bases in the native miR-140 nucleotide sequence are 5-halouracils. In some embodiments, precisely or at least five U bases in the miR-140 nucleotide sequence are 5-halouracils. In a yet other embodiments, precisely or at least six U bases in the miR-140 nucleotide sequence are 5-halouracils. In some embodiments, precisely or at least seven U bases in the miR-140 nucleotide sequence are 5-halouracils. In specific embodiments, all of the U bases in the miR-140 nucleotide sequence, whether in the native and/or in an appended portion, are 5-halouracils.

In an exemplary embodiment, the modified microRNA nucleic acid composition of the present disclosure has a nucleotide sequence of CAGU$^F$GGUUUUACCCU$^F$AUG-GU$^F$AG [SEQ ID NO. 9], wherein U$^F$ is a halouracil, specifically 5-fluorouracil.

In yet another embodiment, the modified microRNA nucleic acid composition of the present disclosure has a nucleotide sequence of CAGU$^F$GGU$^F$U$^F$U$^F$U$^F$ACCCU$^F$AU$^F$GGU$^F$AG [SEQ ID NO. 16], wherein U$^F$ is a halouracil, specifically 5-fluorouracil.

In another exemplary embodiment, the present disclosure is directed to nucleic acid compositions that include a modified native miR-192 or miR-215 nucleotide sequence that has been modified by replacing at least one of the uracil bases with a 5-halouracil. In some embodiments, the modified miR-192 nucleotide sequence has been modified by replacing at least one of the U bases with a 5-fluorouracil. More specifically, the nucleic acid composition contains at least the following native miR-192 nucleotide sequence: CUGACCUAUGAAUUGACAGCC [SEQ ID NO. 10], wherein at least one, two, three, four or all of the uracil bases in the shown nucleic acid sequence are replaced by a 5-halouracil.

In specific embodiments, precisely one of the U bases in the modified miR-192 nucleotide sequence is a 5-halouracil. In other embodiments, precisely or at least two U bases in the modified miR-192 nucleotide sequence are 5-halouracils. In another set of embodiments, precisely or at least three U bases in the modified miR-192 nucleotide sequence are 5-halouracils. In other embodiments, precisely or at least four U bases in the modified miR-192 or miR-215 nucleotide sequence are 5-halouracils. In specific embodiments, all of the U bases in the modified miR-192 or miR-215 sequence, whether in the native and/or in an appended portion of the nucleic acid, are 5-halouracils.

In an exemplary embodiment, the nucleic acid composition of the present disclosure has a modified miR-192 or modified miR-215 nucleotide sequence of CU$^F$GACCU$^F$AU$^F$GAAU$^F$U$^F$GACAGCC [SEQ ID NO. 11], wherein U$^F$ is a halouracil, specifically 5-fluorouracil.

In another exemplary embodiment, the present disclosure is directed to nucleic acid compositions that include a modified native miR-502 nucleotide sequence that has been modified by replacing uracil with 5-halouracil. In some embodiments, the modified miR-502 nucleotide sequence has been modified by replacing at least one of the U bases with a 5-fluorouracil. More specifically, the nucleic acid composition contains at least the following native miR-502 nucleotide sequence: AUCCUUGCUAUCUGGGUGCUA [SEQ ID NO. 12], wherein at least one, two, three, four, five, six, seven or all of the uracil bases in the shown nucleic acid sequence are replaced by a 5-halouracil.

In another set of embodiments, precisely one of the U bases in the miR-502 nucleotide sequence is a 5-halouracil. In a second set of embodiments, precisely or at least two U bases in the miR-502 nucleotide sequence are 5-halouracils. In another set of embodiments, precisely or at least three U bases in the miR-502 nucleotide sequence are 5-halouracils. In other embodiments, precisely or at least four U bases in the miR-502 nucleotide sequence are 5-halouracils. In other embodiments, precisely or at least five U bases in the miR-502 nucleotide sequence are 5-halouracils. In other embodiments, precisely or at least six U bases in the modified miR-502 nucleotide sequence are 5-halouracils. In other embodiments, precisely or at least seven U bases in the miR-502 nucleotide sequence are 5-halouracils. In specific embodiments, all of the U bases in the miR-502 nucleotide sequence, whether in the native and/or in an appended portion, are 5-halouracils.

In an exemplary embodiment, the modified miR-502 nucleic acid composition of the present disclosure has a modified nucleotide sequence of AU$^F$CCU$^F$U$^F$GCUAU$^F$CU$^F$GGGU$^F$GCU$^F$A [SEQ ID NO. 13], wherein U$^F$ is a halouracil, specifically 5-fluorouracil.

In another exemplary embodiment, the present disclosure is directed to nucleic acid compositions that include a modified miR-506 nucleotide sequence that includes a 5-halouracil. In some embodiments, the modified miR-506 nucleotide sequence has been modified by replacing at least one of the U bases with a 5-halouracil, such as 5-fluorouracil. For instance, the nucleic acid composition can contain at least the following native miR-506 nucleotide sequence: UAUUCAGGAAGGUGUUACUUAA [SEQ ID NO. 14], wherein at least one, two, three, four, five, six, seven or all of the uracil bases in the shown nucleic acid sequence are replaced by a 5-halouracil.

In another set of embodiments, precisely one of the U bases in the native miR-506 nucleotide sequence is replaced by a 5-halouracil. In a second set of embodiments, precisely or at least two U bases in the modified miR-506 nucleotide sequence are 5-halouracils. In another set of embodiments, precisely or at least three U bases in the modified miR-506 nucleotide sequence are 5-halouracils. In other embodiments, precisely or at least four U bases in the modified miR-506 nucleotide sequence are 5-halouracils. In other embodiments, precisely or at least five U bases in the modified miR-506 nucleotide sequence are 5-halouracils. In other embodiments, precisely or at least six U bases in the modified miR-506 nucleotide sequence are 5-halouracils. In other embodiments, precisely or at least seven U bases in the modified miR-506 nucleotide sequence are 5-halouracils. In specific embodiments, all of the U bases in the modified miR-506 nucleotide sequence, whether in the native and/or in an appended portion, are 5-halouracils.

In an exemplary embodiment, the miR-506 nucleic acid composition of the present disclosure has a modified microRNA nucleotide sequence of U$^F$AU$^F$U$^F$CAGGAAGGU$^F$GU$^F$U$^F$ACU$^F$U$^F$AA [SEQ ID NO. 15], wherein U$^F$ is a halouracil, specifically 5-fluorouracil.

In yet another embodiment, the present disclosure provides nucleic acid compositions that include a modified miR-34 nucleotide sequence that includes a 5-halouracil. In some embodiments, the modified miR-34 nucleotide sequence has been modified by replacing at least one of the U bases with a 5-halouracil, such as 5-fluorouracil. For instance, the nucleic acid composition can contain at least the following native miR-34 nucleotide sequence: UGGCAGUGUCUUAGCUGGUUGU [SEQ ID NO. 17], wherein at least one, two, three, four, five, six, seven, eight or all of the uracil bases in the shown nucleic acid sequence are replaced by a 5-halouracil.

In another set of embodiments, precisely one of the U bases in the native miR-34 nucleotide sequence is replaced by a 5-halouracil. In a second set of embodiments, precisely or at least two U bases in the modified miR-34 nucleotide sequence are 5-halouracils. In another set of embodiments, precisely or at least three U bases in the modified miR-34 nucleotide sequence are 5-halouracils. In other embodiments, precisely or at least four U bases in the modified miR-34 nucleotide sequence are 5-halouracils. In other embodiments, precisely or at least five U bases in the modified miR-34 nucleotide sequence are 5-halouracils. In other embodiments, precisely or at least six U bases in the modified miR-34 nucleotide sequence are 5-halouracils. In other embodiments, precisely or at least seven U bases in the modified miR-34 nucleotide sequence are 5-halouracils. In other embodiments, precisely or at least eight U bases in the modified miR-34 nucleotide sequence are 5-halouracils. In specific embodiments, all of the U bases in the modified miR-34 nucleotide sequence, whether in the native and/or in an appended portion, are 5-halouracils.

In an exemplary embodiment, the miR-34 nucleic acid composition of the present disclosure has a modified microRNA nucleotide sequence of U$^F$GGCAGU$^F$GU$^F$CU$^F$U$^F$AGCU$^F$GGU$^F$UFGU$^F$ [SEQ ID NO. 18], wherein U$^F$ is a halouracil, specifically 5-fluorouracil.

In yet another embodiment, the present disclosure provides nucleic acid compositions that include a modified miR-200a nucleotide sequence that includes a 5-halouracil. In some embodiments, the modified miR-200a nucleotide sequence has been modified by replacing at least one of the U bases with a 5-halouracil, such as 5-fluorouracil. For instance, the nucleic acid composition can contain at least the following native miR-200a nucleotide sequence: UAACACUGUCUGGUAACGAUGU [SEQ ID NO. 19], wherein at least one, two, three, four, five, six, or all of the uracil bases in the shown nucleic acid sequence are replaced by a 5-halouracil.

In another set of embodiments, precisely one of the U bases in the native miR-200a nucleotide sequence is replaced by a 5-halouracil. In a second set of embodiments, precisely or at least two U bases in the modified miR-200a nucleotide sequence are 5-halouracils. In another set of embodiments, precisely or at least three U bases in the modified miR-200a nucleotide sequence are 5-halouracils. In other embodiments, precisely or at least four U bases in the modified miR-200a nucleotide sequence are 5-halouracils. In other embodiments, precisely or at least five U bases in the modified miR-200a nucleotide sequence are 5-halouracils. In other embodiments, precisely or at least six U bases in the modified miR-200a nucleotide sequence are 5-halouracils. In specific embodiments, all of the U bases in the modified miR-200a nucleotide sequence, whether in the native and/or in an appended portion, are 5-halouracils.

In an exemplary embodiment, the miR-200a nucleic acid composition of the present disclosure has a modified microRNA nucleotide sequence of U$^F$AACACU$^F$GU$^F$CU$^F$GGU$^F$AACGAU$^F$GU$^F$ [SEQ ID NO. 20], wherein U$^F$ is a halouracil, specifically 5-fluorouracil.

In other embodiments, the present disclosure provides nucleic acid compositions that include a modified miR-200b nucleotide sequence that includes a 5-halouracil. In some embodiments, the modified miR-200b nucleotide sequence has been modified by replacing at least one of the U bases with a 5-halouracil, such as 5-fluorouracil. For instance, the nucleic acid composition can contain at least the following native miR-200b nucleotide sequence: UAAUACUGCCUGGUAAUGAUGA [SEQ ID NO. 21], wherein at least one, two, three, four, five, six, or all of the uracil bases in the shown nucleic acid sequence are replaced by a 5-halouracil.

In another set of embodiments, precisely one of the U bases in the native miR-200b nucleotide sequence is replaced by a 5-halouracil. In a second set of embodiments, precisely or at least two U bases in the modified miR-200b nucleotide sequence are 5-halouracils. In another set of embodiments, precisely or at least three U bases in the modified miR-200b nucleotide sequence are 5-halouracils. In other embodiments, precisely or at least four U bases in the modified miR-200b nucleotide sequence are 5-halouracils. In other embodiments, precisely or at least five U bases in the modified miR-200b nucleotide sequence are 5-halouracils. In other embodiments, precisely or at least six U bases in the modified miR-200b nucleotide sequence are 5-halouracils. In specific embodiments, all of the U bases in the modified miR-200b nucleotide sequence, whether in the native and/or in an appended portion, are 5-halouracils.

In an exemplary embodiment, the miR-200b nucleic acid composition of the present disclosure has a modified microRNA nucleotide sequence of $U^F AAU^F ACU^F GC$-$CU^F GGU^F AAU^F GAU^F GA$ [SEQ ID NO. 22], wherein $U^F$ is a halouracil, specifically 5-fluorouracil.

In yet another embodiment, the present disclosure provides nucleic acid compositions that include a modified miR-200c nucleotide sequence that includes a 5-halouracil. In some embodiments, the modified miR-200c nucleotide sequence has been modified by replacing at least one of the U bases with a 5-halouracil, such as 5-fluorouracil. For instance, the nucleic acid composition can contain at least the following native miR-200c nucleotide sequence: UAAUACUGCCGGGUAAUGAUGGA [SEQ ID NO. 23], wherein at least one, two, three, four, five or all of the uracil bases in the shown nucleic acid sequence are replaced by a 5-halouracil.

In another set of embodiments, precisely one of the U bases in the native miR-200c nucleotide sequence is replaced by a 5-halouracil. In a second set of embodiments, precisely or at least two U bases in the modified miR-200c nucleotide sequence are 5-halouracils. In another set of embodiments, precisely or at least three U bases in the modified miR-200c nucleotide sequence are 5-halouracils. In other embodiments, precisely or at least four U bases in the modified miR-200c nucleotide sequence are 5-halouracils. In other embodiments, precisely or at least five U bases in the modified miR-200c nucleotide sequence are 5-halouracils. In specific embodiments, all of the U bases in the modified miR-200c nucleotide sequence, whether in the native and/or in an appended portion, are 5-halouracil s.

In an exemplary embodiment, the miR-200c nucleic acid composition of the present disclosure has a modified microRNA nucleotide sequence of $U^F AAU^F A$-$CU^F GCCGGGGU^F AAU^F GAU^F GGA$ [SEQ ID NO. 24], wherein $U^F$ is a halouracil, specifically 5-fluorouracil.

In some embodiments, the present disclosure provides nucleic acid compositions that include a modified miR-145 nucleotide sequence that includes a 5-halouracil. In one instance, the modified miR-145 nucleotide sequence has been modified by replacing at least one of the U bases with a 5-halouracil, such as 5-fluorouracil. For example, the nucleic acid composition can contain at least the following native miR-145 nucleotide sequence: GUCCAGUUUUCCCAGGAAUCCCU [SEQ ID NO. 25], wherein at least one, two, three, four, five, six, or all of the uracil bases in the shown nucleic acid sequence are replaced by a 5-halouracil.

In another set of embodiments, precisely one of the U bases in the native miR-145 nucleotide sequence is replaced by a 5-halouracil. In a second set of embodiments, precisely or at least two U bases in the modified miR-145 nucleotide sequence are 5-halouracils. In another set of embodiments, precisely or at least three U bases in the modified miR-145 nucleotide sequence are 5-halouracils. In other embodiments, precisely or at least four U bases in the modified miR-145 nucleotide sequence are 5-halouracils. In other embodiments, precisely or at least five U bases in the modified miR-145 nucleotide sequence are 5-halouracils. In other embodiments, precisely or at least six U bases in the modified miR-145 nucleotide sequence are 5-halouracils. In specific embodiments, all of the U bases in the modified miR-145 nucleotide sequence, whether in the native and/or in an appended portion, are 5-halouracils.

In an exemplary embodiment, the miR-145 nucleic acid composition of the present disclosure has a modified microRNA nucleotide sequence of $GU^F CCAGU^F U^F$ $U^F U^F CCCAGGAAU^F CCCU^F$ [SEQ ID NO. 26], wherein $U^F$ is a halouracil, specifically 5-fluorouracil.

In another exemplary embodiment, nucleic acid compositions are provided that include a modified native miR-194 nucleotide sequence that has been modified by replacing at least one of the uracil bases with a 5-halouracil. In some embodiments, the modified miR-194 nucleotide sequence has been modified by replacing at least one of the U bases with a 5-fluorouracil. More specifically, the nucleic acid composition contains at least the following native miR-194 nucleotide sequence: UGUAACAGCAACUCCAU-GUGGA [SEQ ID NO. 27], wherein at least one, two, three, four or all of the uracil bases in the shown nucleic acid sequence are replaced by a 5-halouracil.

In specific embodiments, precisely one of the U bases in the modified miR-194 nucleotide sequence is a 5-halouracil. In another of embodiments, precisely or at least two U bases in the modified miR-194 nucleotide sequence are 5-halouracils. In another set of embodiments, precisely or at least three U bases in the modified miR-194 nucleotide sequence are 5-halouracils. In other embodiments, precisely or at least four U bases in the modified miR-194 nucleotide sequence are 5-halouracils. In specific embodiments, all of the U bases in the modified miR-194 sequence, whether in the native and/or in an appended portion of the nucleic acid, are 5-halouracils.

In an exemplary embodiment, the nucleic acid composition of the present disclosure has a modified miR-194 nucleotide sequence of $U^F GU^F AACAGCAACU^F C$-$CAU^F GU^F GGA$ [SEQ ID NO. 28], wherein $U^F$ is a halouracil, specifically 5-fluorouracil.

In yet another embodiment, the present disclosure provides nucleic acid compositions that include a modified miR-let-7 nucleotide sequence that includes a 5-halouracil. In some embodiments, the modified miR let-7 nucleotide sequence has been modified by replacing at least one of the U bases with a 5-halouracil, such as 5-fluorouracil. For instance, the nucleic acid composition can contain at least the following native miR-let-7 nucleotide sequence: UGAG-GUAGUAGGUUGUAUAGUU [SEQ ID NO. 29], wherein at least one, two, three, four, five, six, seven, eight or all of the uracil bases in the shown nucleic acid sequence are replaced by a 5-halouracil.

In another set of embodiments, precisely one of the U bases in the native miR-let-7 nucleotide sequence is replaced by a 5-halouracil. In a second set of embodiments, precisely or at least two U bases in the modified miR-let-7 nucleotide sequence are 5-halouracils. In another set of embodiments, precisely or at least three U bases in the modified miR-34 nucleotide sequence are 5-halouracils. In other embodiments, precisely or at least four U bases in the modified miR-let-7 nucleotide sequence are 5-halouracils. In other embodiments, precisely or at least five U bases in the modified miR-let-7 nucleotide sequence are 5-halouracils. In other embodiments, precisely or at least six U bases in the modified miR-let-7 nucleotide sequence are 5-halouracils. In other embodiments, precisely or at least seven U bases in the modified miR-let-7 nucleotide sequence are 5-halouracils. In other embodiments, precisely or at least eight U bases in the modified miR-let-7 nucleotide sequence are 5-halouracils. In specific embodiments, all of the U bases in the modified miR-let-7 nucleotide sequence, whether in the native and/or in an appended portion, are 5-halouracils.

In an exemplary embodiment, the miR-let-7 nucleic acid composition of the present disclosure has a modified microRNA nucleotide sequence of $U^F$GAGGU$^F$AGU$^F$AG-GU$^F$U$^F$GU$^F$AU$^F$AGU$^F$U$^F$ [SEQ ID NO. 30], wherein $U^F$ is a halouracil, specifically 5-fluorouracil.

In some embodiments, the 5-halouracil is, for example, 5-fluorouracil, 5-chlorouracil, 5-bromouracil, or 5-iodouracil. In specific embodiments, the 5-halouracil is 5-fluorouracil, or a combination thereof. In certain instances, all of the U-bases of the modified miR are substituted with a 5-fluorouracil.

The present disclosure is also directed to formulations of a modified microRNA composition described herein or a formulation that includes combinations thereof, i.e., at least two modified microRNAs. In certain embodiments, the formulations can include pharmaceutical preparations that comprise the above-described nucleic acid compositions and other known pharmacological agents, such as one or more pharmaceutically acceptable carriers.

The present disclosure reveals that the modified microRNAs each exhibit a potent efficacy as an anti-cancer therapeutic. Notably, each of the modified microRNA nucleic acid compositions tested reduce cancer cell proliferation, tumor growth and development in a dose dependent manner by inducing cell-cycle arrest in all six cancer types examined.

Therefore, another aspect of the present disclosure is directed to a method for treating cancer that includes administering to a subject an effective amount of one or more of nucleic acid compositions described herein. In certain embodiments of the present methods, the nucleic acid compositions include a modified miR-129, miR-15a, miR-192/miR-215, miR-140, miR-502, miR-506, miR-34, miR-200a, miR-200b, miR-200c, miR-145, miR-194, miR-let-7 nucleotide sequence or a combination thereof, wherein at least one, two, three, four, or more of the uracil nucleotide bases in each of the native (unmodified) nucleotide sequences have been replaced by a 5-halouracil.

In specific embodiments, the present methods include administering a nucleic acid composition of the present disclosure to a subject having cancer or a predisposition to cancer, whereby the nucleic acid composition is a modified miR-129 or a modified miR-15a nucleic acid. In a specific embodiment of the present disclosure, the modified microRNA administered has nucleic acid sequence selected from the group consisting of CU$^F$U$^F$U$^F$U$^F$U$^F$GCGGU$^F$-CU$^F$GGGCU$^F$U$^F$GC [SEQ ID NO. 4], CUUUUUGCG-GU$^F$CU$^F$GGGCU$^F$U$^F$GC [SEQ ID NO. 5], U$^F$AGCAGCA-CAU$^F$AAU$^F$GGU$^F$U$^F$U$^F$GU$^F$G [SEQ ID NO. 6], and UAGCAGCACAU$^F$AAU$^F$GGU$^F$U$^F$U$^F$GU$^F$G [SEQ ID NO. 7].

In other embodiments, the present methods include administering a nucleic acid composition of the present disclosure to a subject having cancer or a predisposition to cancer, whereby the nucleic acid composition is a modified miR-140 or a modified miR-192 nucleic acid. In a specific embodiment of the present disclosure, the modified microRNA administered has nucleic acid sequence selected from the group consisting of CAGU$^F$GGUUUUA CCCU$^F$AUGGU$^F$AG [SEQ ID NO. 9], CAGU$^F$GGU$^F$U$^F$U$^F$U$^F$ACCCU$^F$AU$^F$GGU$^F$AG [SEQ ID NO. 16], and CU$^F$GACCU$^F$AU$^F$GAAU$^F$U$^F$GACAGCC [SEQ ID NO. 11].

In another embodiment, the present methods include administering a nucleic acid composition of the present disclosure to a subject having cancer or a predisposition to cancer, whereby the nucleic acid composition is a modified miR-502 or a modified miR-506 nucleic acid. In a specific embodiment of the present disclosure, the modified microRNA administered has nucleic acid sequence selected from the group consisting of AU$^F$CCU$^F$U$^F$GCUAU$^F$-CU$^F$GGGU$^F$GCU$^F$A [SEQ ID NO. 13], and U$^F$AU$^F$U$^F$CAGGAAGGU$^F$GU$^F$U$^F$ACU$^F$U$^F$AA [SEQ ID NO. 15].

In another embodiment, the present methods include administering a nucleic acid composition of the present disclosure to a subject having cancer or a predisposition to cancer, whereby the nucleic acid composition includes a modified miR-34, a modified miR-145, a modified miR-200a, a modified miR-200b, a modified miR-200c, a modified miR-194 or a modified miR-let-7 nucleic acid. In a specific embodiment of the present disclosure, the modified microRNA administered has nucleic acid sequence selected from the group consisting of U$^F$GGCAGU$^F$GU$^F$CU$^F$U$^F$-AGCU$^F$GGU$^F$U$^F$GU$^F$ [SEQ ID NO. 18], U$^F$AACA-CU$^F$GU$^F$CU$^F$GGU$^F$AACGAU$^F$GU$^F$ [SEQ ID NO. 20], U$^F$AAU$^F$ACU$^F$GCCU$^F$GGU$^F$AAU$^F$GAU$^F$GA [SEQ ID NO. 22], U$^F$AAU$^F$ACU$^F$GCCGGGU$^F$AAU$^F$GAU$^F$GGA [SEQ ID NO. 24], GU$^F$CCAGU$^F$U$^F$U$^F$U$^F$CCCAG-GAAU$^F$CCCU$^F$ [SEQ ID NO. 26], U$^F$GU$^F$AACAGCAA-CU$^F$CCAU$^F$GU$^F$GGA [SEQ ID NO. 28], U$^F$GAGGU$^F$-AGU$^F$AGGU$^F$U$^F$GU$^F$AU$^F$AGU$^F$U$^F$ [SEQ ID NO. 30], and a combination thereof.

In some instances, the subject being treated by the present methods is a mammal. In certain embodiments, the subject being treated is a human, dog, horse, pig, mouse, or rat. In a specific embodiment, the subject is a human that has been diagnosed with cancer, or has been identified as having a predisposition to developing cancer. In some embodiments, the cancer being treated can be, for example, colorectal, stomach, esophageal, lung, ovarian cancer, pancreatic, or cervical cancer. In certain embodiments, the methods of the present disclosure treat a subject for one or more of the following types of cancer: colorectal cancer, gastric cancer, pancreatic cancer, lung cancer, blood cancer (e.g., leukemia) or breast cancer.

The data provided herein surprisingly shows an increased potency of the modified microRNAs described herein when compared to known anticancer agents, such as 5-FU alone in several different cancer models, including colorectal cancer, pancreatic cancer, and lung cancer. For example, the present disclosure provides the unexpected finding that the described modified nucleic acid compositions are substantially more potent in inhibiting cancer progression and tumorigenesis than 5-FU, miR-15a, miR-129, miR-140, miR-192, miR-215, miR-502, miR-506, miR-34, miR-145, miR-200a, miR-200b, miR-200c, miR-194 or miR-let-7 alone, or than a combination of 5-FU and corresponding native microRNAs.

As such, the present compositions and methods provide the additional benefit of permitting a lower dosing, which results in lower toxicity and fewer side effects. A further significant advantage exhibited by the described nucleic acid compositions is that the instant compositions have significantly improved efficacy compared to native miR-15a, miR-129, miR-140, miR-192, miR-215, miR-502, miR-506, miR-34, miR-145, miR-200a, miR-200b, miR-200c, miR-194 or miR-let-7 nucleic acids that have not been modified with a halouracil. Thus, at least in view of the noted advantages, the nucleic acid compositions disclosed herein represent a substantial advance in the treatment of all cancers.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIGS. 1A-1P. Chemical representation of exemplary modified microRNA nucleotide sequences of the present disclosure. (A) Chemical representation of miR-129 nucleotide sequence in which all U bases are replaced by a halouracil (i.e., $U^F$), as set forth in SEQ ID NO: 4. (B) Chemical representation of miR-129 in which only the non-seed portion of miR-129 has U bases replaced with halouracils), as set forth in SEQ ID NO: 5. (C) Chemical representation of miR-15a nucleotide sequence in which all U bases are replaced with a halouracil), as set forth in SEQ ID NO: 6. (D) Chemical representation of miR-15a in which only the non-seed portion of miR-15a has U bases replaced with halouracils), as set forth in SEQ ID NO: 7. (E) Chemical representation of the miR-140 nucleotide sequence in which certain (3) U bases are replaced by a halouracil as set forth in SEQ ID NO: 9. (F) Chemical representation of a modified miR-140 nucleotide sequence in which certain all U bases are replaced by a halouracil as set forth in SEQ ID NO: 16. (G) Chemical representation of the miR-192 nucleotide sequence in which certain (5) U bases are replaced by a halouracil as set forth in SEQ ID NO: 11. (H) Chemical representation of the miR-502 nucleotide sequence in which certain (7) U bases are replaced by a halouracil as set forth in SEQ ID NO: 13. (I) Chemical representation of the miR-506 nucleotide sequence in which all (i.e., 8) U bases are replaced by a halouracil as set forth in SEQ ID NO: 15. (J) Chemical representation of the modified miR-34 nucleotide sequence in which all (i.e., 9) U bases are replaced by a halouracil as set forth in SEQ ID NO: 18. (K) Chemical representation of the modified miR-200a nucleotide sequence in which all (i.e., 7) U bases are replaced by a halouracil as set forth in SEQ ID NO: 20. (L) Chemical representation of the modified miR-200b nucleotide sequence in which all (i.e., 7) U bases are replaced by a halouracil as set forth in SEQ ID NO: 22. (M) Chemical representation of the modified miR-200c nucleotide sequence in which all (i.e., 6) U bases are replaced by a halouracil as set forth in SEQ ID NO: 24. (N) Chemical representation of the modified miR-145 nucleotide sequence in which all (i.e., 7) U bases are replaced by a halouracil as set forth in SEQ ID NO: 26. (O) Chemical representation of the modified miR-194 nucleotide sequence in which all (i.e., 5) U bases are replaced by a halouracil as set forth in SEQ ID NO: 28. (P) Chemical representation of the modified miR-let-7 nucleotide sequence in which all (i.e., 9) U bases are replaced by a halouracil as set forth in SEQ ID NO: 30. The orientation of each exemplary modified microRNA depicted is provided by a 5' to 3' or 3' to 5' designation.

FIG. 10. Modified miR-15a expression reduces the ability of cancer stem cells to induce cancer cell colony formation. In colon cancer stem cells, expression of unmodified miR-15a (miR-15a) inhibited cancer cell colony formation when compared to the ability of cancer stem cells provided with a non-specific control microRNA (Negative). Treatment with an exemplary modified miR-15a (5-FU-miR-15a) of the present disclosure prevented cancer cell colony formation completely.

FIGS. 13A-13B. Exemplary modified microRNAs of the present disclosure exhibit an enhanced ability to inhibit human colorectal cancer cell proliferation. Additional exemplary modified microRNAs were tested for their ability to inhibit colorectal cancer cell proliferation in HCT116 human colorectal cancer cells. (A) An exemplary modified miR-140 mimic as set forth in SEQ ID NO: 9 was administered to human colorectal cancer cells and revealed an increased ability to inhibit colorectal cancer cell proliferation when compared to negative control microRNAs. (B) An exemplary modified miR-192 mimic as set forth in SEQ ID NO: 11 was administered to human colorectal cancer cells and revealed an increased ability to inhibit colorectal cancer cell proliferation when compared to negative control microRNAs.

FIGS. 16A-16C. Another exemplary modified microRNA nucleic acid enter cancer cells and effectively reduce target protein expression and inhibits tumor development and progression by inducing cell cycle arrest. (A) Graph showing target (ZEB-1 and Fibronectin) specificity and the ability of an exemplary modified miR-200b (with all U bases replaced with 5-FU, 5-FU-miR-200b) compared to that of control miRNA, and an unmodified miR-200b nucleic acid. (B) Modified miR-200b nucleic acids (5-FU-miR-200b) enter a breast cancer cell for triple negative breast cancer (MDA-MB-231 cell line) and breaks down TS-FdUMP indicating anti cancer activity. (C) Expression of modified miR-200b (5-FU-miR-200b) significantly increases the G1/S ratio (top) and sub G1 population (bottom) of cells compared to expression of exogenous native miR-200b and a negative control (miR-NC) indicating that modified miR-200b inhibits breast cancer cell cycle progression.

DETAILED DESCRIPTION OF THE DISCLOSURE

Figure 2A:
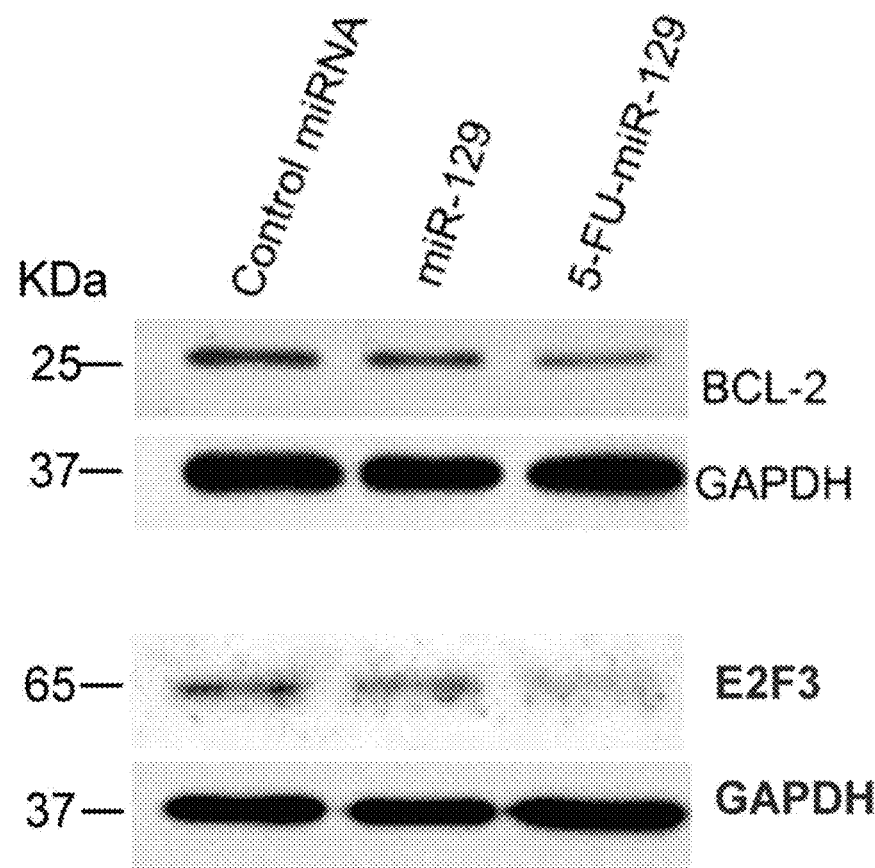
FIGS. 2A-2C. Exemplary modified microRNA nucleic acids enter cancer cells and effectively reduce target protein expression. (A) Graph showing target (E2F3) specificity and the ability of an exemplary modified miR-129 (with all U bases replaced with 5-FU, 5-FU-miR-129) compared to that of control miRNA, and an unmodified miR-129 nucleic acid. (B) A quantitative Real-Time PCR analysis showing that modified miR-129 nucleic acids (mimic) enter cancer cells. (C) Modified miR-129 nucleic acids (mimic) enter a cancer cell and break downs TS-FdUMP significantly better than 5-FU alone.

The present disclosure provides nucleic acid compositions that incorporate one or more halouracil molecules. Without being bound by any one particular theory, surprisingly, the present disclosure reveals that the replacement of uracil nucleotides within a microRNA oligonucleotide sequence with a 5-halouracil increases the ability of the microRNA to inhibit cancer development, progression and tumorigenesis. Moreover, the data herein shows that contacting a many types of cancer cells with a modified microRNA composition of the present disclosure regulates cell-cycle progression and reduces tumorigenesis by, for example, reducing cancer cell proliferation and increasing the efficacy of chemotherapeutic agents. Furthermore, it is shown that the modified microRNAs of the present disclosure retain target specificity, can be delivered without the use of harmful and ineffective delivery vehicles (e.g., nanoparticles), and exhibit enhanced potency and stability without abolishing the natural function of the endogenous microRNA. As such, the present disclosure provides various nucleic acid (e.g., microRNA) compositions having 5-halouracil molecules incorporated in their nucleic acid sequences and methods for using the same to treat cancer. The present disclosure further provides formulations, such as pharmaceutical compositions comprising the modified nucleic acid compositions, and methods for treating cancers that include administration of the same to a subject in need thereof.

Nucleic Acid Compositions.

The term "microRNA" or "miRNA" or "miR" is used interchangeably to refer to small non-coding ribose nucleic acid (RNA) molecules that are capable of regulating the expression of genes through interacting with messenger RNA molecules (mRNA), DNA or proteins. Typically, microRNAs are composed of nucleic acid sequences of about 19-25 nucleotides (bases) and are found in mammalian cells. Mature microRNA molecules are single stranded RNA molecules processed from double stranded precursor transcripts that form local hairpin structures. The hairpin structures are typically cleaved by the Dicer enzyme to form a double stranded microRNA duplex. See, e.g., Bartel, *Cell*, (2004) 116 pp. 281-297. The term microRNA as used herein incorporates both the duplex (i.e., double stranded miRs) and single stranded miRs (i.e., mature miRs) in both the 5' to 3' direction and complementary strand in the 3' to 5' direction. In specific embodiments, modified miRs of the present disclosure are composed of single stranded mature MiRs.

Usually, one of the two strands of a microRNA duplex is packaged in a microRNA ribonucleoprotein complex (microRNP). A microRNP in, for example, humans, also includes the proteins eIF2C2/Argonaute (Ago2), the helicase Gemin3, and Gemin 4. Other members of the Argonaute protein family, such as Ago1, 3, and 4, also associate with microRNAs and form microRNPs.

The term "modified microRNA", "modified miRNA", "modified miR" or "mimic" are used interchangeably herein to refer to a microRNA that differs from the native or endogenous microRNA (unmodified microRNA) polynucleotide. More specifically, in the present disclosure a modified microRNA differs from the unaltered or unmodified microRNA nucleic acid sequence by one or more base. In some embodiments of the present disclosure, a modified microRNA of the present disclosure includes at least one uracil (U) nucleotide base replaced by a 5-halouracil. In other embodiments a modified microRNA includes an additional nucleotide (i.e., adenine (A), cytosine (C), uracil (U), and guanine (G)) and at least one uracil base that is substituted with a 5-halouracil.

In one aspect of the present disclosure, nucleic acid compositions that include a modified microRNA nucleotide sequence having at least one uracil base (U, U bases) that has been replaced with a 5-halouracil, such as 5-fluorouracil (5-FU) are described. As further discussed herein, the nucleic acid compositions of the present disclosure are useful, at least, in the treatment of all cancers. In particular, the exemplary modified microRNAs of the present disclosure have been shown herein to be effective in the treatment of colorectal cancer, pancreatic cancer, lung cancer, gastric cancer, blood cancers (e.g., leukemia) and breast cancer.

In some embodiments, the nucleic acid compositions contain a nucleotide sequence that has been modified by derivatizing at least one of the uracil nucleobases at the 5-position with a group that provides a similar effect as a halogen atom. In some embodiments, the group providing the similar effect has a similar size in weight or spatial dimension to a halogen atom, e.g., a molecular weight of up to or less than 20, 30, 40, 50, 60, 70, 80, 90, or 80 g/mol. In certain embodiments, the group providing a similar effect as a halogen atom may be, for example, a methyl group, trihalomethyl (e.g., trifluoromethyl) group, pseudohalide (e.g., trifluoromethanesulfonate, cyano, or cyanate) or deuterium (D) atom. The group providing a similar effect as a halogen atom may be present in the absence of or in addition to a 5-halouracil base in the microRNA nucleotide sequence.

Moreover, in other embodiments, the group providing a similar effect as a halogen atom may be located in the native (or seed) portion and/or in an appended portion of the microRNA nucleotide sequence, which will be readily identified by one of ordinary skill in the art. In some embodiments, one or more (or all) of the above types of groups providing a similar effect as a halogen atom are excluded from the modified miRNA nucleotide sequence. When all such alternative groups are excluded, only one or more halogen atoms are present as substituents in the 5-position of one or more uracil groups in the microRNA nucleotide sequence.

In certain embodiments, the modified microRNA has more than one, or exactly one uracil that has been replaced with a 5-halouracil.

In some embodiments, the modified microRNA nucleotide sequence includes three, four, five, six, seven, eight or more uracil bases that have been replaced with a 5-halouracil.

In one embodiment, all of the uracil nucleotide bases of the modified mRNA have been replaced by a 5-halouracil.

In some embodiments, the 5-halouracil is, for example, 5-fluorouracil, 5-chlorouracil, 5-bromouracil, or 5-iodouracil. In specific embodiments, the 5-halouracil is 5-fluorouracil The term "miR-129" as used herein, is meant to be synonymous with the terms "microRNA-129" or "miRNA-129" and refers to an oligonucleotide having the following nucleotide sequence: CUUUUUGCGGUCUGGGCUUGC [SEQ ID NO. 1], where it is understood that C=cytosine, U=uracil, and G=guanine bases. The foregoing nucleotide sequence is herein referred to as an unmodified miR-129 (i.e., "native") sequence unless otherwise specified. In other embodiments, MiR-129 may also be referred to in the field as hsa-miR-129 with accession number MI0000252 for the stem loop containing double stranded microRNA; hsa-miR-129-5p for the mature miR 5' to 3' strand as set forth in accession number MIMAT0000242; and hsa-miR-129-3p for the 3' to 5' complementary strand of a duplex miR-129 molecule as set forth by accession number MIMAT0004548. MiR-129 is well known and has been studied in detail. See, e.g., J. Wu et al., *Cell Cycle*, (2010) 9:9, 1809-1818. As also well known in the art, the miR-129 sequence may be modified to produce a "miR-129 mimic", which has a sequence modified from the native sequence, but that retains the known function or activity of the native miR-129. Unless otherwise stated, all such modified miR-129 compositions are herein considered to be within the scope of the term "miR-129 mimic" as used herein.

A particular modified miR-129 nucleic acid sequence (mimic) of interest contains two U bases (i.e., two U-containing nucleotides) covalently appended to an end of the miR-129 native sequence, such as in CUUUUUGCGGU-CUGGGCUUGC-UU [SEQ ID NO. 3]. In the foregoing sequence, the two terminal U bases continue or extend the miR-129 native sequence from 21 nucleotide bases to 23 nucleotide bases. Generally, the miR-129 mimic contains no more than one, two, three, four, or five additional bases (i.e., as additional nucleotides) covalently appended to the miR-129 native sequence, wherein the additional bases are independently selected from C, U, G, and C, or the additional bases may be exclusively U. Typically, the miR-129 is used in single-strand form, but double-stranded versions are also considered herein.

In one embodiment, the present disclosure is directed to nucleic acid compositions that contain a miR-129 nucleotide sequence that has been modified by replacing at least one of the uracil nucleobases (i.e., U bases) with a 5-halouracil, i.e., wherein at least one of the U bases in the miR-129 sequence, whether in the native and/or in an appended portion, is a 5-halouracil. The 5-halouracil can be, for example, 5-fluorouracil, 5-chlorouracil, 5-bromouracil, or 5-iodouracil.

In a first set of embodiments, precisely one of the U bases in the miR-129 sequence is a 5-halouracil. In a second set of embodiments, precisely or at least two U bases in the miR-129 sequence are 5-halouracils. In a third set of embodiments, precisely or at least three U bases in the miR-129 sequence are 5-halouracils. In a fourth set of embodiments, precisely or at least four U bases in the miR-129 sequence are 5-halouracils. In a fifth set of embodiments, precisely or at least five U bases in the miR-129 sequence are 5-halouracils. In a sixth set of embodiments, all of the U bases in the miR-129 sequence, whether in the native and/or in an appended portion, are 5-halouracils.

In a specific embodiment, the nucleic composition of the present disclosure has a modified microRNA nucleotide sequence of $CU^FU^FU^FU^FU^FGCGGU^FCU^F GGGCU^FU^FGC$ as set forth in SEQ ID NO. 4, wherein $U^F$ is a halouracil, specifically 5-fluorouracil.

The U bases that are replaced with 5-halouracils in the miR-129 sequence may be located in an unmodified part of the miR-129 sequence, as provided above, or, in the case of a miR-129 mimic, may be located in one or more U bases covalently appended to the native miR-129, as also provided above. In other embodiments, a seed portion of the native miR-129 nucleotide sequence, GUUUUUGC remains unmodified with a 5-halouracil while one or more (or all) of the remaining U bases in the remainder of the miR-129 nucleotide sequence are replaced with the equivalent number of 5-halouracils.

For example, in a specific embodiment, the nucleic acid composition of the present disclosure has a modified microRNA nucleotide sequence of $CUUUUUGCGGU^F$-$CU^FGGGCU^FU^FGC$ as set forth in SEQ ID NO. 5, whereby $U^F$ is a halouracil, specifically 5-fluorouracil.

In alternative embodiments, the nucleic acid composition contains a miR-129 nucleotide sequence that has been modified by derivatizing at least one of the uracil (U) nucleobases at the 5-position with a group that provides a similar effect as a halogen atom. In some embodiments, the group providing the similar effect has a similar size in weight or spatial dimension to a halogen atom, e.g., a molecular weight of up to or less than 20, 30, 40, 50, 60, 70, 80, 90, or 80 g/mol. The group providing a similar effect as a halogen atom may be, for example, a methyl group, trihalomethyl (e.g., trifluoromethyl) group, pseudohalide (e.g., trifluoromethanesulfonate, cyano, or cyanate) or deuterium (D) atom. The group providing a similar effect as a halogen atom may be present in the absence of or in addition to a 5-halouracil base in the miR-129 nucleotide sequence. Moreover, the group providing a similar effect as a halogen atom may be located in the native (or seed) portion and/or in an appended portion of the miR-129 nucleotide sequence. In some embodiments, one or more (or all) of the above types of groups providing a similar effect as a halogen atom are excluded from the miR-129 nucleotide sequence. When all such alternative groups are excluded, only one or more halogen atoms are present as substituents in the 5-position of one or more uracil groups in the miR-129 nucleotide sequence.

In another exemplary embodiment, the present disclosure is directed to nucleic acid compositions that include a miR-15a nucleotide sequence that has been modified. In some embodiments, the miR-15a nucleotide sequence has been modified by replacing at least one of the U bases with a 5-halouracil.

The term "miR-15a", as used herein, is meant to be synonymous with the terms "microRNA-15a" or "miRNA-15a" and refers to an oligonucleotide having the following nucleotide sequence: UAGCAGCACAUAAUGGUUU-GUG [SEQ ID NO. 2], where it is understood that A=adenine, C=cytosine, U=uracil, and G=guanine bases. The foregoing nucleotide sequence is herein referred to as a miR-15a unmodified (i.e., "native") sequence unless otherwise specified. In other embodiments, MiR-15a may also be referred to in the field as hsa-miR-15a with accession number(s) MI0000069 for the stem loop containing double stranded microRNA; and hsa-miR-15a-5p with accession number MI0000068 for the mature miR 5' to 3'; and hsa-miR-15a-3p for the 3' to 5' complementary strand of a duplex miR-15a molecule as set forth by accession number MIMAT0004488. MiR-15a is well known and has been studied in detail, e.g., Xie T, et al. *Clin Transl Oncol*. (2015) 17(7):504-10; and Acunzo M, and Croce C M, *Clin. Chem*. (2016) 62(4):655-6. As stated above for miR-129 mimics, methods for creating a miR-15a mimic are known by those of ordinary skill in the art. Unless otherwise stated, all such modified miR-15a forms are herein considered to be within the scope of the term "miR-15a mimic", as used herein.

Generally, a modified miR-15a (i.e., miR-15a mimic) contains no more than one, two, three, four, or five additional nucleotides covalently appended to the miR-15a native sequence, wherein the additional bases are independently selected from C, U, G, and C, or the additional bases may be exclusively U. Typically, the miR-15a is used in single-strand form, but double-stranded versions are also considered herein.

In some embodiments, at least one of the U bases in the miR-15a sequence, whether in the native and/or in an appended portion, is a 5-halouracil. The 5-halouracil can be, for example, 5-fluorouracil, 5-chlorouracil, 5-bromouracil, or 5-iodouracil.

In a one set of embodiments, precisely one of the U bases in the miR-15a sequence is a 5-halouracil. In a second set of embodiments, precisely or at least two U bases in the miR-15a sequence are 5-halouracils. In another set of embodiments, precisely or at least three U bases in the miR-15a oligonucleotide sequence are 5-halouracils. In other embodiments, precisely or at least four U bases in the miR-15a sequence are 5-halouracils. In some embodiments, precisely or at least five U bases in the miR-15a sequence are 5-halouracils. In a yet other embodiments, precisely or at least six U bases in the miR-15a sequence are 5-halouracils. In specific embodiments, all of the U bases in the miR-15a sequence, whether in the native and/or in an appended portion, are 5-halouracils.

In one embodiment, the nucleic acid composition of the present disclosure has a modified microRNA nucleotide sequence of $U^FAGCAGCACAU^FAAU^FGGU^FU^FU^FGU^FG$ [SEQ ID NO. 6], wherein $U^F$ is a halouracil, specifically 5-fluorouracil.

The U bases that are replaced with 5-halouracils in the miR-15a sequence may be located in an unmodified part of the miR-15a sequence, as provided above, or, in the case of a miR-15a mimic, may be located in one or more uracil bases that are appended to the native miR-15a, as also provided above.

In other embodiments, a seed portion of the native miR-15a nucleotide sequence, UAGCAGCA, remains unmodified with a 5-halouracil while one or more (or all) of the remaining U bases in the remainder of the miR-15a nucleotide sequence (non-seed portion) are replaced with a 5-halouracil.

In specific embodiments, the nucleic acid composition of the present disclosure has a modified miR-15a nucleotide sequence of $UAGCAGCACAU^FAAU^FGGU^FU^FU^FGU^FG$ [SEQ ID NO. 7], wherein $U^F$ is a halouracil, specifically 5-fluorouracil.

In certain embodiments, the nucleic acid composition contains a miR-15a nucleotide sequence that has been modified by derivatizing at least one of the uracil (U) nucleobases at the 5-position with a group that provides a similar effect as a halogen atom. In some embodiments, the group providing the similar effect has a similar size in weight or spatial dimension to a halogen atom, e.g., a molecular weight of up to or less than 20, 30, 40, 50, 60, 70, 80, 90, or 80 g/mol. The group providing a similar effect as a halogen atom may be, for example, a methyl group, trihalomethyl (e.g., trifluoromethyl) group, pseudohalide (e.g., trifluoromethanesulfonate, cyano, or cyanate) or deuterium (D) atom. The group providing a similar effect as a halogen atom may be present in the absence of or in addition to a 5-halouracil base in the miR-15a nucleotide sequence. Moreover, the group providing a similar effect as a halogen atom may be located in the native (or seed) portion and/or in an appended portion of the miR-15a nucleotide sequence.

In some embodiments, one or more (or all) of the above types of groups providing a similar effect as a halogen atom are excluded from miR-15a nucleotide sequence. When all such alternative groups are excluded, only one or more halogen atoms are present as substituents in the 5-position of one or more uracil groups in the miR-15a nucleotide sequence.

In another exemplary embodiment, the present disclosure is directed to nucleic acid compositions that include a miR-140 nucleotide sequence that has been modified. In some embodiments, the miR-140 nucleotide sequence has been modified by replacing at least one of the U bases with a 5-halouracil.

The term "miR-140", as used herein, is meant to be synonymous with the terms "microRNA-140" or "miRNA-140" and refers to an oligonucleotide having the following nucleotide sequence: CAGUGGUUUUACCCUAUG-GUAG [SEQ ID NO. 8], where it is understood that A=adenine, C=cytosine, U=uracil, and G=guanine bases. The foregoing nucleotide sequence is herein referred to as a miR-140 unmodified (i.e., "native") sequence unless otherwise specified. In other embodiments, MiR-140 may also be referred as hsa-miR-140 with accession number MI0000456 for the stem loop containing double stranded microRNA; hsa-miR-140-5p for the mature miR 5' to 3' strand as set forth in accession number MIMAT0000431 or NT_010498; and hsa-miR-140-3p for the 3' to 5' complementary strand of a duplex miR-140 molecule as set forth by accession number MIMAT0004597. MiR-140 is well known and has been studied in detail, e.g., Zhai, H. et al., *Oncotarget*. (2015) 6: 19735-46. As stated above for exemplary mimics miR-129 and miR-15a, methods for creating a miR-140 mimic are known by those of ordinary skill in the art. Unless otherwise stated, all such modified miR-140 forms are herein considered to be within the scope of the term "miR-140 mimic", as used herein.

Generally, a modified miR-140 nucleic acid (i.e., miR-140 mimic) contains no more than one, two, three, four, or five additional nucleotides covalently appended to the miR-140 native sequence, wherein the additional bases are independently selected from C, U, G, and C, or the additional bases may be exclusively U. Typically, the miR-140 mimic is used in single-strand form, but double-stranded versions are also considered herein.

In some embodiments, at least one of the U bases in the miR-140 sequence, whether in the native and/or in an appended portion, is a 5-halouracil. The 5-halouracil can be, for example, 5-fluorouracil, 5-chlorouracil, 5-bromouracil, or 5-iodouracil.

In one set of embodiments, precisely one of the U bases in the miR-140 mimic sequence is a 5-halouracil. In a second set of embodiments, precisely or at least two U bases in the miR-140 sequence are 5-halouracils. In another set of embodiments, precisely or at least three U bases in the miR-140 oligonucleotide sequence are 5-halouracils. In other embodiments, precisely or at least four U bases in the miR-140 sequence are 5-halouracils. In some embodiments, precisely or at least five U bases in the miR-140 mimic sequence are 5-halouracils. In a yet other embodiments, precisely or at least six U bases in the miR-140 mimic sequence are 5-halouracils. In specific embodiments, all of the U bases in the miR-140 sequence, whether in the native and/or in an appended portion, are 5-halouracils.

In an exemplary embodiment, the nucleic acid composition of the present disclosure has a modified miR-140 nucleotide sequence of $CAGU^FGGUUUUACCCU^FAUG-GU^FAG$ [SEQ ID NO. 9], wherein $U^F$ is a halouracil, specifically 5-fluorouracil.

In another embodiment, the nucleic acid composition of the present disclosure has a modified miR-140 nucleotide sequence of $UAGCAGCACAU^FAAU^FGGU^FU^FU^FU^FG$ [SEQ ID NO. 16], wherein $U^F$ is a halouracil, specifically 5-fluorouracil.

The U bases that are replaced with 5-halouracils in a miR-140 mimic sequence may be located in an unmodified part of the miR-140 sequence, as provided above, or may be located in one or more uracil bases that are appended to the native miR-140 sequence, as provided above.

In other embodiments, a seed portion of the native miR-140 nucleotide sequence, remains unmodified with a 5-halouracil while one or more (or all) of the remaining U bases in the remainder of the miR-140 nucleotide sequence (non-seed portion) are replaced with a 5-halouracil.

In another exemplary embodiment, the present disclosure is directed to nucleic acid compositions that include a miR-192 nucleotide sequence that has been modified. In some embodiments, the miR-192 nucleotide sequence has been modified by replacing at least one of the U bases with a 5-halouracil.

The term "miR-192", as used herein, is meant to be synonymous with the terms "microRNA-192", "miRNA-192" "microRNA-215", "miR-215" or "miRNA-215" and refers to an oligonucleotide having the following nucleotide sequence: CUGACCUAUGAAUUGACAGCC [SEQ ID NO. 10], where it is understood that A=adenine, C=cytosine, U=uracil, and G=guanine bases. The foregoing nucleotide sequence is herein referred to as a miR-192 unmodified (i.e., "native") sequence unless otherwise specified. In some embodiments, miR-192 may be referred to in the field as hsa-miR-192 or hsa-miR-215 with accession numbers MI0000234, or MI0000291 for the stem loop containing double stranded microRNA; hsa-miR-192-5p or hsa-miR-215-5p for the mature miR 5' to 3' strand as set forth in accession number MIMAT0000222 and MIMAT0000272, respectively; and hsa-miR-192-3p or hsa-miR-215-3p for the 3' to 5' complementary strand of a duplex molecule as set forth by accession number MIMAT0004543 and MIMAT0026476, respectively. MiR-192 is well known and has been studied in detail, e.g., Song, B. et al., *Clin. Cancer Res.* (2008), 14: 8080-8086, and Song, B. et al., *Mol. Cancer.* (2010), 9:96 pp. 1476-4598. As stated above for exemplary mimics miR-129, miR-140 and miR-15a, methods for creating a miR-192 mimics are known by those of ordinary skill in the art. Unless otherwise stated, all such modified miR-192 nucleic acid forms are herein considered to be within the scope of the term "miR-192 mimic", as used herein.

Generally, a modified miR-192 (i.e., miR-192 mimic) contains no more than one, two, three, four, or five additional nucleotides covalently appended to the miR-192 native sequence, wherein the additional bases are independently selected from C, U, G, and C, or the additional bases may be exclusively U. Typically, the miR-192 mimic is used in single-strand form, but double-stranded versions are also considered herein.

In some embodiments, at least one of the U bases in the miR-192 or miR-215 sequence, whether in the native and/or in an appended portion, is a 5-halouracil. The 5-halouracil can be, for example, 5-fluorouracil, 5-chlorouracil, 5-bromouracil, or 5-iodouracil.

In another set of embodiments, precisely one of the U bases in the miR-192 mimic sequence is a 5-halouracil. In a second set of embodiments, precisely or at least two U bases in the miR-192 sequence are 5-halouracils. In another set of embodiments, precisely or at least three U bases in the miR-192 oligonucleotide sequence are 5-halouracils. In other embodiments, precisely or at least four U bases in the miR-192 sequence are 5-halouracils. In specific embodiments, all of the U bases in the miR-192 sequence, whether in the native and/or in an appended portion, are 5-halouracils.

In an exemplary embodiment, the nucleic acid composition of the present disclosure has a modified miR-192 nucleotide sequence of CU$^F$GACCU$^F$AU$^F$GAAU$^F$U$^F$GACAGCC [SEQ ID NO. 11], wherein U$^F$ is a halouracil, specifically 5-fluorouracil.

The U bases that are replaced with 5-halouracils in the miR-192 mimic sequence may be located in an unmodified part of the miR-192 sequence, as provided above, or may be located in one or more uracil bases that are appended to the native miR-192 sequence, as provided above.

In other embodiments, a seed portion of the native miR-192 nucleotide sequence remains unmodified with a 5-halouracil while one or more (or all) of the remaining U bases in the remainder of the miR-192 nucleotide sequence (non-seed portion) are replaced with a 5-halouracil or combination thereof.

In another exemplary embodiment, the present disclosure is directed to nucleic acid compositions that include a miR-502 nucleotide sequence that has been modified. In some embodiments, the miR-502 nucleotide sequence has been modified by replacing at least one of the U bases with a 5-halouracil.

The term "miR-502", as used herein, is meant to be synonymous with the terms "microRNA-502" or "miRNA-502" and refers to an oligonucleotide having the following nucleotide sequence: AUCCUUGCUAUCUGGGUGCUA [SEQ ID NO. 12], where it is understood that A=adenine, C=cytosine, U=uracil, and G=guanine bases. The foregoing nucleotide sequence is herein referred to as a miR-502 unmodified (i.e., "native") sequence unless otherwise specified. In other embodiments, MiR-502 may also be referred to in the field as hsa-miR-502 with accession number MI0003186 for the stem loop containing double stranded microRNA; hsa-miR-502-5p for the mature miR 5' to 3' strand as set forth in accession number MIMAT0002873; and hsa-miR-502-3p for the 3' to 5' complementary strand of a duplex miR-502 molecule as set forth by accession number MIMAT0004775. MiR-502 is well known and has been studied in detail, e.g., Zhai, H, et al., *Oncogene.* (2013), 32:12 pp. 1570-1579. As stated above for exemplary mimics miR-129, miR-140, miR-192 and miR-15a, methods for creating a miR-502 mimics are known by those of ordinary skill in the art. Unless otherwise stated, all such modified miR-502 nucleic acid forms are herein considered to be within the scope of the term "miR-502 mimic", as used herein.

Generally, a modified miR-502 (i.e., miR-502 mimic) contains no more than one, two, three, four, or five additional nucleotides covalently appended to the miR-502 native sequence, wherein the additional bases are independently selected from C, U, G, and C, or the additional bases may be exclusively U. Typically, the miR-502 mimic is used in single-strand form, but double-stranded versions are also considered herein.

In some embodiments, at least one of the U bases in the miR-502 sequence, whether in the native and/or in an appended portion, is a 5-halouracil. The 5-halouracil can be, for example, 5-fluorouracil, 5-chlorouracil, 5-bromouracil, or 5-iodouracil.

In another set of embodiments, precisely one of the U bases in the miR-502 mimic sequence is a 5-halouracil. In a second set of embodiments, precisely or at least two U bases in the miR-502 sequence are 5-halouracils. In another set of embodiments, precisely or at least three U bases in the miR-502 oligonucleotide sequence are 5-halouracils. In other embodiments, precisely or at least four U bases in the miR-502 sequence are 5-halouracils. In other embodiments, precisely or at least five U bases in the miR-502 sequence are 5-halouracils. In other embodiments, precisely or at least six U bases in the miR-502 sequence are 5-halouracils. In other embodiments, precisely or at least seven U bases in the miR-502 sequence are 5-halouracils. In specific embodiments, all of the U bases in the miR-502 sequence, whether in the native and/or in an appended portion, are 5-halouracils.

In an exemplary embodiment, the nucleic acid composition of the present disclosure has a modified miR-502 nucleotide sequence of AU$^F$CCU$^F$U$^F$GCUAU$^F$CU$^F$GG-GU$^F$GCU$^F$A [SEQ ID NO. 13], wherein U$^F$ is a halouracil, specifically 5-fluorouracil.

The U bases that are replaced by 5-halouracils in the miR-502 mimic sequence may be located in an unmodified part of the miR-502 sequence, as provided above, or may be located in one or more uracil bases that are appended to the native miR-502 sequence, as provided above.

In other embodiments, a seed portion of the native miR-502 nucleotide sequence remains unmodified with a 5-halouracil while one or more (or all) of the remaining U bases in the remainder of the miR-502 nucleotide sequence (non-seed portion) are replaced by a 5-halouracil or combination thereof.

In another exemplary embodiment, the present disclosure is directed to nucleic acid compositions that include a miR-506 nucleotide sequence that has been modified. In some embodiments, the miR-506 nucleotide sequence has been modified by replacing at least one of the U bases with a 5-halouracil.

The term "miR-506", as used herein, is meant to be synonymous with the terms "microRNA-506" or "miRNA-506" and refers to an oligonucleotide having the following nucleotide sequence: UAUUCAGGAAGGUGUUAC-UUAA [SEQ ID NO. 14], where it is understood that A=adenine, C=cytosine, U=uracil, and G=guanine bases. The foregoing nucleotide sequence is herein referred to as a miR-506 unmodified (i.e., "native") sequence unless otherwise specified. In other embodiments, miR-506 may also be referred to in the field as hsa-miR-506 with accession number MI0003193 for the stem loop containing double stranded microRNA; hsa-miR-506-5p for the mature miR 5' to 3' strand as set forth in accession number MIMAT0022701; and hsa-miR-506-3p for the 3' to 5' complementary strand of a duplex miR-506 molecule as set forth by accession number MIMAT0002878. MiR-506 is well known and has been studied in detail, e.g., Li, J, et al., *Oncotarget*. (2016), 7:38 pp. 62778-62788, and Li, J. et al., Oncogene. (2016) 35 pp. 5501-5514. As stated above for exemplary mimics miR-129, miR-140, miR-502, miR-192 and miR-15a, methods for creating a miR-506 mimics are known by those of ordinary skill in the art. Unless otherwise stated, all such modified miR-506 nucleic acid forms are herein considered to be within the scope of the term "miR-506 mimic", as used herein.

Generally, a modified miR-506 (i.e., miR-506 mimic) contains no more than one, two, three, four, or five additional nucleotides covalently appended to the miR-506 native sequence, wherein the additional bases are independently selected from C, U, G, and C, or the additional bases may be exclusively U. Typically, the miR-506 mimic is used in single-strand form, but double-stranded versions are also considered herein.

In some embodiments, at least one of the U bases in the miR-506 sequence, whether in the native and/or in an appended portion, is a 5-halouracil. The 5-halouracil can be, for example, 5-fluorouracil, 5-chlorouracil, 5-bromouracil, or 5-iodouracil.

In another set of embodiments, precisely one of the U bases in the miR-506 mimic sequence is a 5-halouracil. In a second set of embodiments, precisely or at least two U bases in the miR-506 sequence are 5-halouracils. In another set of embodiments, precisely or at least three U bases in the miR-506 oligonucleotide sequence are 5-halouracils. In other embodiments, precisely or at least four U bases in the miR-506 sequence are 5-halouracils. In other embodiments, precisely or at least five U bases in the miR-506 sequence are 5-halouracils. In other embodiments, precisely or at least six U bases in the miR-506 sequence are 5-halouracils. In other embodiments, precisely or at least seven U bases in the miR-506 sequence are 5-halouracils. In specific embodiments, all of the U bases in the miR-506 sequence, whether in the native and/or in an appended portion, are 5-halouracils.

In an exemplary embodiment, the nucleic acid composition of the present disclosure has a modified miR-506 nucleotide sequence of U$^F$AU$^F$U$^F$CAGGAAGGU$^F$GU$^F$U$^F$ACU$^F$U$^F$AA [SEQ ID NO. 15], wherein U$^F$ is a halouracil, specifically 5-fluorouracil.

The U bases that are replaced with 5-halouracils in the miR-506 mimic sequence may be located in an unmodified part of the miR-506 sequence, as provided above, or may be located in one or more uracil bases that are appended to the native miR-506 sequence, as provided above.

In other embodiments, a seed portion of the native miR-506 nucleotide sequence remains unmodified with a 5-halouracil while one or more (or all) of the remaining U bases in the remainder of the miR-506 nucleotide sequence (non-seed portion) are replaced with a 5-halouracil or combination thereof.

In another exemplary embodiment, the present disclosure is directed to nucleic acid compositions that include a miR-34 nucleotide sequence that has been modified. In some embodiments, the miR-34 nucleotide sequence has been modified by replacing at least one of the U bases with a 5-halouracil.

The term "miR-34", as used herein, is meant to be synonymous with the terms "microRNA-34", "miR-34a" or "miRNA-34" and refers to an oligonucleotide having the following nucleotide sequence: UGGCAGUGUC-UUAGCUGGUUGU [SEQ ID NO. 17]. The foregoing nucleotide sequence is herein referred to as the miR-34 unmodified (i.e., "native") sequence unless otherwise specified. In other embodiments, miR-34 may also be referred to in the field as hsa-miR-34 with accession number MI0000268 for the stem loop containing double stranded microRNA; hsa-miR-34a-5p for the mature miR 5' to 3' strand as set forth in accession number MIMAT0000255; and hsa-miR-34a-3p for the 3' to 5' complementary strand of a duplex miR-129 molecule as set forth by accession number MIMAT0004557. MiR-34 is well known and has been studied in detail. See, e.g., Lui, W O, et al., *Cancer Res.* 67 pp. 6031-6043 (2007). As stated above for exemplary mimics miR-129, miR-140, miR-502, miR-506 miR-192 and miR-15a, methods for creating a modified miR-34 polynucleotides are known by those of ordinary skill in the art. Unless otherwise stated, all such modified miR-34 nucleic acid forms are herein considered to be within the scope of the term "miR-34 mimic" or "modified miR-34", as used herein.

Generally, a modified miR-34 (i.e., miR-34 mimic) contains no more than one, two, three, four, or five additional nucleotides covalently appended to the miR-34 native sequence, wherein the additional bases are independently selected from C, U, G, and C, or the additional bases may be exclusively U. Typically, the miR-34 mimic is used in single-strand form, but double-stranded versions are also considered herein.

In some embodiments, at least one of the U bases in the miR-34 sequence, whether in the native and/or in an appended portion, is a 5-halouracil. The 5-halouracil can be, for example, 5-fluorouracil, 5-chlorouracil, 5-bromouracil, or 5-iodouracil.

In other embodiments, precisely one of the U bases in the miR-34 mimic sequence is a 5-halouracil. In a second set of embodiments, precisely or at least two U bases in the miR-34 sequence are 5-halouracils. In another set of embodiments, precisely or at least three U bases in the miR-34 oligonucleotide sequence are 5-halouracils. In other embodiments, precisely or at least four U bases in the miR-34 sequence are 5-halouracils. In other embodiments, precisely or at least five U bases in the miR-34 sequence are 5-halouracils. In other embodiments, precisely or at least six U bases in the miR-34 sequence are 5-halouracils. In other embodiments, precisely or at least seven U bases in the miR-34 sequence are 5-halouracils. In yet other embodiments, precisely or at least eight U bases in the miR-34 sequence are 5-halouracils. In specific embodiments, all of the U bases in the miR-34 sequence, whether in the native and/or in an appended portion, are 5-halouracils.

In an exemplary embodiment, the nucleic acid composition of the present disclosure has a modified miR-34 nucleotide sequence of $U^F GGCAGU^F GU^F CU^F U^F AGCU^F GGU^F U^F GU^F$ [SEQ ID NO. 18], wherein $U^F$ is a halouracil, specifically 5-fluorouracil.

The U bases that are replaced with 5-halouracils in the modified miR-34 sequence may be located in an unmodified part of the miR-34 sequence, as provided above, or may be located in one or more uracil bases that are appended to the native miR-34 sequence, as provided above.

In other embodiments, a seed portion of the native miR-34 nucleotide sequence remains unmodified with a 5-halouracil while one or more (or all) of the remaining U bases in the remainder of the miR-34 nucleotide sequence (non-seed portion) are replaced with a 5-halouracil or combination thereof.

In another exemplary embodiment, the present disclosure is directed to nucleic acid compositions that include a miR-200a nucleotide sequence that has been modified. In some embodiments, the miR-200a nucleotide sequence has been modified by replacing at least one of the U bases with a 5-halouracil.

The term "miR-200a", as used herein, is meant to be synonymous with the terms "microRNA-200a" or "miRNA-200a" and refers to an oligonucleotide having the following nucleotide sequence: UAACACUGUCUG-GUAACGAUGU [SEQ ID NO. 19]. The foregoing nucleotide sequence is herein referred to as the miR-200a unmodified (i.e., "native") sequence unless otherwise specified. In other embodiments, MiR-200a may also be referred to in the field as hsa-miR-200a with accession number MI0000737 for the stem loop containing double stranded microRNA: hsa-miR-200a-5p for the mature miR 5' to 3' strand as set forth in accession number MIMAT0001620; and hsa-miR-200a-3p for the 3' to 5' complementary strand of a duplex miR-200a molecule as set forth by accession number MIMAT000682. MiR-200a is well known and has been studied in detail. See, e.g., Lagos-Quintana M, et al., *RNA*. 9: pp. 175-179 (2003). As stated above, methods for creating modified miR-200a polynucleotides are known by those of ordinary skill in the art. Unless otherwise stated, all such modified miR-200a nucleic acid forms are herein considered to be within the scope of the term "miR-200a mimic" or "modified miR-200a", as used herein.

Generally, a modified miR-200a (i.e., miR-200a mimic) contains no more than one, two, three, four, or five additional nucleotides covalently appended to the miR-200a native sequence, wherein the additional bases are independently selected from C, U, G, and C, or the additional bases may be exclusively U. Typically, the miR-200a mimic is used in single-strand form, but double-stranded versions are also considered herein.

In some embodiments, at least one of the U bases in the miR-200a sequence, whether in the native and/or in an appended portion, is a 5-halouracil. The 5-halouracil can be, for example, 5-fluorouracil, 5-chlorouracil, 5-bromouracil, or 5-iodouracil.

In other embodiments, precisely one of the U bases in the miR-200a mimic sequence is a 5-halouracil. In a second set of embodiments, precisely or at least two U bases in the miR-200a sequence are 5-halouracils. In another set of embodiments, precisely or at least three U bases in the miR-200a oligonucleotide sequence are 5-halouracils. In other embodiments, precisely or at least four U bases in the miR-200a sequence are 5-halouracils. In other embodiments, precisely or at least five U bases in the miR-200a sequence are 5-halouracils. In other embodiments, precisely or at least six U bases in the miR-200a sequence are 5-halouracils. In a specific embodiment, all of the U bases in the miR-200a sequence, whether in the native and/or in an appended portion, are 5-halouracils.

In an exemplary embodiment, the nucleic acid composition of the present disclosure has a modified miR-200a nucleotide sequence of $U^F AACACU^F GU^F CU^F GGU^F AACGAU^F GU^F$ [SEQ ID NO. 20], wherein $U^F$ is a halouracil, specifically 5-fluorouracil.

The U bases that are replaced with 5-halouracils in the modified miR-200a sequence may be located in an unmodified part of the miR-200a sequence, as provided above, or may be located in one or more uracil bases that are appended to the native miR-200a sequence, as provided above.

In other embodiments, a seed portion of the native miR-200a nucleotide sequence remains unmodified with a 5-halouracil while one or more (or all) of the remaining U bases in the remainder of the miR-200a nucleotide sequence (non-seed portion) are replaced with a 5-halouracil or combination thereof.

In another exemplary embodiment, the present disclosure is directed to nucleic acid compositions that include a miR-200b nucleotide sequence that has been modified. In some embodiments, the miR-200b nucleotide sequence has been modified by replacing at least one of the U bases with a 5-halouracil.

The term "miR-200b", as used herein, is meant to be synonymous with the terms "microRNA-200b" or "miRNA-200b" and refers to an oligonucleotide having the following nucleotide sequence: UAAUACUGCCUG-GUAAUGAUGA [SEQ ID NO. 21]. The foregoing nucleotide sequence is herein referred to as the miR-200b unmodified (i.e., "native") sequence unless otherwise specified. In other embodiments, miR-200b may also be referred to in the field as hsa-miR-200b with accession number MI0000342 for the stem loop containing double stranded microRNA; hsa-miR-200b-5p for the mature miR 5' to 3' strand as set forth in accession number MIMAT00004571; and hsa-miR-200b-3p for the 3' to 5' complementary strand of a duplex miR-200b molecule as set forth by accession number MIMAT0000318. MiR-200b is well known and has been studied in detail. See, e.g., Altuvia Y, et al., *Nucleic Acids*

Res. 33 pp. 2697-2706 (2005). As above, methods for creating modified miR-200b polynucleotides are known by those of ordinary skill in the art. Unless otherwise stated, all such modified miR-200b nucleic acid forms are herein considered to be within the scope of the term "miR-200b mimic" or "modified miR-200b", as used herein.

Generally, a modified miR-200b (i.e., miR-200b mimic) contains no more than one, two, three, four, or five additional nucleotides covalently appended to the miR-200b native sequence, wherein the additional bases are independently selected from C, U, G, and C, or the additional bases may be exclusively U. Typically, the miR-200b mimic is used in single-strand form, but double-stranded versions are also considered herein.

In some embodiments, at least one of the U bases in the miR-200b sequence, whether in the native and/or in an appended portion, is a 5-halouracil. The 5-halouracil can be, for example, 5-fluorouracil, 5-chlorouracil, 5-bromouracil, or 5-iodouracil.

In other embodiments, precisely one of the U bases in the miR-200b mimic sequence is a 5-halouracil. In a second set of embodiments, precisely or at least two U bases in the miR-200b sequence are 5-halouracils. In another set of embodiments, precisely or at least three U bases in the miR-200b oligonucleotide sequence are 5-halouracils. In other embodiments, precisely or at least four U bases in the miR-200b sequence are 5-halouracils. In other embodiments, precisely or at least five U bases in the miR-200b sequence are 5-halouracils. In other embodiments, precisely or at least six U bases in the miR-200b sequence are 5-halouracils. In a specific embodiment, all of the U bases in the miR-200b sequence, whether in the native and/or in an appended portion, are 5-halouracils.

In an exemplary embodiment, the nucleic acid composition of the present disclosure has a modified miR-200b nucleotide sequence of $U^F AAU^F ACU^F GCCU^F GGU^F AAU^F GAU^F GA$ [SEQ ID NO. 22], wherein $U^F$ is a halouracil, specifically 5-fluorouracil.

The U bases that are replaced with 5-halouracils in the modified miR-200b sequence may be located in an unmodified part of the miR-200b sequence, as provided above, or may be located in one or more uracil bases that are appended to the native miR-200b sequence, as provided above.

In other embodiments, a seed portion of the native miR-200b nucleotide sequence remains unmodified with a 5-halouracil while one or more (or all) of the remaining U bases in the remainder of the miR-200b nucleotide sequence (non-seed portion) are replaced with a 5-halouracil or combination thereof.

In another exemplary embodiment, the present disclosure is directed to nucleic acid compositions that include a miR-200c nucleotide sequence that has been modified. In some embodiments, the miR-200c nucleotide sequence has been modified by replacing at least one of the U bases with a 5-halouracil.

The term "miR-200c", as used herein, is meant to be synonymous with the terms "microRNA-200c" or "miRNA-200c" and refers to an oligonucleotide having the following nucleotide sequence: UAAUACUGCCGG-GUAAUGAUGGA [SEQ ID NO. 23]. The foregoing nucleotide sequence is herein referred to as the miR-200c unmodified (i.e., "native") sequence unless otherwise specified. In other embodiments, miR-200c may also be referred to in the field as hsa-miR-200c with accession number MI0000650 for the stem loop containing double stranded microRNA: hsa-miR-200c-5p for the mature miR 5' to 3' strand as set forth in accession number MIMAT00004657; and hsa-miR-200c-3p for the 3' to 5' complementary strand of a duplex miR-200c molecule as set forth by accession number MIMAT0000617. MiR-200c is well known and has been studied in detail. See, e.g., Landgraf P, et al., Cell. 129 pp. 1401-1414 (2007). As stated above, methods for creating modified miR-200c polynucleotides are known by those of ordinary skill in the art. Unless otherwise stated, all such modified miR-200c nucleic acid forms are herein considered to be within the scope of the term "miR-200c mimic" or "modified miR-200c", as used herein.

Generally, a modified miR-200c (i.e., miR-200c mimic) contains no more than one, two, three, four, or five additional nucleotides covalently appended to the miR-200c native sequence, wherein the additional bases are independently selected from C, U, G, and C, or the additional bases may be exclusively U. Typically, the miR-200c mimic is used in single-strand form, but double-stranded versions are also considered herein.

In some embodiments, at least one of the U bases in the miR-200c sequence, whether in the native and/or in an appended portion, is a 5-halouracil. The 5-halouracil can be, for example, 5-fluorouracil, 5-chlorouracil, 5-bromouracil, or 5-iodouracil.

In other embodiments, precisely one of the U bases in the miR-200c mimic sequence is a 5-halouracil. In a second set of embodiments, precisely or at least two U bases in the miR-200c sequence are 5-halouracils. In another set of embodiments, precisely or at least three U bases in the miR-200c oligonucleotide sequence are 5-halouracils. In other embodiments, precisely or at least four U bases in the miR-200c sequence are 5-halouracils. In other embodiments, precisely or at least five U bases in the miR-200c sequence are 5-halouracils. In a specific embodiment, all of the U bases in the miR-200c sequence, whether in the native and/or in an appended portion, are 5-halouracils.

In an exemplary embodiment, the nucleic acid composition of the present disclosure has a modified miR-200c nucleotide sequence of $U^F AAU^F ACU^F GCCGGGU^F AAU^F GAU^F GGA$ [SEQ ID NO. 24], wherein U is a halouracil, specifically 5-fluorouracil.

The U bases that are replaced with 5-halouracils in the modified miR-200c sequence may be located in an unmodified part of the miR-200c sequence, as provided above, or may be located in one or more uracil bases that are appended to the native miR-200c sequence, as provided above.

In other embodiments, a seed portion of the native miR-200c nucleotide sequence remains unmodified with a 5-halouracil while one or more (or all) of the remaining U bases in the remainder of the miR-200c nucleotide sequence (non-seed portion) are replaced with a 5-halouracil or combination thereof.

In another exemplary embodiment, the present disclosure is directed to nucleic acid compositions that include a miR-145 nucleotide sequence that has been modified. In some embodiments, the miR-145 nucleotide sequence has been modified by replacing at least one of the U bases with a 5-halouracil.

The term "miR-145", as used herein, is meant to be synonymous with the terms "microRNA-145" or "miRNA-145" and refers to an oligonucleotide having the following nucleotide sequence: GUCCAGUUUUCCCAG-GAAUCCCU [SEQ ID NO. 25], where it is understood that A=adenine, C=cytosine, U=uracil, and G=guanine bases. The foregoing nucleotide sequence is herein referred to as a miR-145 unmodified (i.e., "native") sequence unless otherwise specified. In some embodiments, miR-145 may be referred to in as hsa-miR-145 with accession number MI0000461 for the stem loop containing double stranded microRNA; hsa-miR-145-5p for the mature miR 5' to 3' strand as set forth in accession number MIMAT0000437; and hsa-miR-145-3p for the 3' to 5' complementary strand of a duplex miR-145 molecule as set forth by accession number MIMAT0004601. MiR-145 is well known and has been studied in detail. See, e.g., Landgraf P, et al., *Cell.* 129 pp. 1401-1414 (2007). As stated above for exemplary mimics miR-129, miR-140, miR-192, 200a, 200b, 200c, miR-34 and miR-15a, methods for creating a miR-145 mimics are known by those of ordinary skill in the art. Unless otherwise stated, all such modified miR-145 nucleic acid forms are herein considered to be within the scope of the term "miR-145 mimic", as used herein.

Generally, a modified miR-145 (i.e., miR-145 mimic) contains no more than one, two, three, four, or five additional nucleotides covalently appended to the miR-145 native sequence, wherein the additional bases are independently selected from C, U, G, and C, or the additional bases may be exclusively U. Typically, the miR-145 mimic is used in single-strand form, but double-stranded versions are also considered herein.

In some embodiments, at least one of the U bases in the miR-145 sequence, whether in the native and/or in an appended portion, is a 5-halouracil. The 5-halouracil can be, for example, 5-fluorouracil, 5-chlorouracil, 5-bromouracil, or 5-iodouracil.

In another set of embodiments, precisely one of the U bases in the miR-145 mimic sequence is a 5-halouracil. In a second set of embodiments, precisely or at least two U bases in the miR-145 sequence are 5-halouracils. In another set of embodiments, precisely or at least three U bases in the miR-145 oligonucleotide sequence are 5-halouracils. In other embodiments, precisely or at least four U bases in the miR-145 sequence are 5-halouracils. In other embodiments, precisely or at least five U bases in the miR-145 sequence are 5-halouracils. In other embodiments, precisely or at least six U bases in the miR-145 sequence are 5-halouracils. In specific embodiments, all of the U bases in the miR-145 sequence, whether in the native and/or in an appended portion, are 5-halouracils.

In an exemplary embodiment, the nucleic acid composition of the present disclosure has a modified miR-145 nucleotide sequence of GU$^F$CCAGU$^F$U$^F$U$^F$U$^F$CCCAG-GAAU$^F$CCCU$^F$ [SEQ ID NO. 26], wherein U is a halouracil, specifically 5-fluorouracil.

The U bases that are replaced by 5-halouracils in the miR-145 mimic sequence may be located in an unmodified part of the miR-145 sequence, as provided above, or may be located in one or more uracil bases that are appended to the native miR-145 sequence, as provided above.

In other embodiments, a seed portion of the native miR-145 nucleotide sequence remains unmodified with a 5-halouracil while one or more (or all) of the remaining U bases in the remainder of the miR-145 nucleotide sequence (non-seed portion) are replaced by a 5-halouracil or combination thereof.

In another exemplary embodiment, the present disclosure is directed to nucleic acid compositions that include a miR-194 nucleotide sequence that has been modified. In some embodiments, the miR-194 nucleotide sequence has been modified by replacing at least one of the U bases with a 5-halouracil.

The term "miR-194", as used herein, is meant to be synonymous with the terms "microRNA-194" or "miRNA-194" and refers to an oligonucleotide having the following nucleotide sequence: UGUAACAGCAACUCCAU-GUGGA [SEQ ID NO. 27]. The foregoing nucleotide sequence is herein referred to as a miR-194 unmodified (i.e., "native") sequence unless otherwise specified. In some embodiments, miR-194 may be referred to in the field as hsa-miR-194 with accession number MI0000488 or MI0000732 for the stem loop containing double stranded microRNA; hsa-miR-94-5p for the mature miR 5' to 3' strand as set forth in accession number MIMAT0000460; and hsa-miR-194-3p for the 3' to 5' complementary strand of a duplex molecule as set forth by accession number MIMAT0004671. MiR-194 is well known and has been studied in detail. See, e.g., Lagos-Quintana M, et al., *RNA.* 9: pp. 175-179 (2003). As is the case for the above, modified microRNAs, methods for creating a miR-194 mimics are known by those of ordinary skill in the art. Unless otherwise stated, all such modified miR-194 nucleic acid forms are herein considered to be within the scope of the term "miR-194 mimic", as used herein.

Generally, a modified miR-194 (i.e., miR-194 mimic) contains no more than one, two, three, four, or five additional nucleotides covalently appended to the miR-194 native sequence, wherein the additional bases are independently selected from C, U, G, and C, or the additional bases may be exclusively U. Typically, the miR-194 mimic is used in single-strand form, but double-stranded versions are also considered herein.

In some embodiments, at least one of the U bases in the miR-194 sequence, whether in the native and/or in an appended portion, is a 5-halouracil. The 5-halouracil can be, for example, 5-fluorouracil, 5-chlorouracil, 5-bromouracil, or 5-iodouracil.

In another set of embodiments, precisely one of the U bases in the miR-194 mimic sequence is a 5-halouracil. In a second set of embodiments, precisely or at least two U bases in the miR-194 sequence are 5-halouracils. In another set of embodiments, precisely or at least three U bases in the miR-194 oligonucleotide sequence are 5-halouracils. In other embodiments, precisely or at least four U bases in the miR-194 sequence are 5-halouracils. In specific embodiments, all of the U bases in the miR-194 sequence, whether in the native and/or in an appended portion, are 5-halouracils.

In an exemplary embodiment, the nucleic acid composition of the present disclosure has a modified miR-194 nucleotide sequence of U$^F$GU$^F$AACAGCAACU$^F$C-CAU$^F$GU$^F$GGA [SEQ ID NO. 28], wherein U$^F$ is a halouracil, specifically 5-fluorouracil.

The U bases that are replaced by 5-halouracils in the miR-194 mimic sequence may be located in an unmodified part of the miR-194 sequence, as provided above, or may be located in one or more uracil bases that are appended to the native miR-194 sequence, as provided above.

In other embodiments, a seed portion of the native miR-194 nucleotide sequence remains unmodified with a 5-halouracil while one or more (or all) of the remaining U bases in the remainder of the miR-194 nucleotide sequence (non-seed portion) are replaced by a 5-halouracil or combination thereof.

In another exemplary embodiment, the present disclosure is directed to nucleic acid compositions that include a miR-let-7 nucleotide sequence that has been modified. In some embodiments, the miR-let-7 nucleotide sequence has been modified by replacing at least one of the U bases with a 5-halouracil.

The term "miR-let-7", as used herein, is meant to be synonymous with the terms "microRNA-let-7" or "miRNA-let-7" and refers to an oligonucleotide having the following nucleotide sequence: UGAGGUAGUAGGUU-GUAUAGUU [SEQ ID NO. 29]. The foregoing nucleotide sequence is herein referred to as a miR-let-7 unmodified (i.e., "native") sequence unless otherwise specified. In other embodiments, miR-let-7 may also be referred to in the field as hsa-miR-let-7a-1 with accession number MI0000060 for the stem loop containing double stranded microRNA; hsa-miR-let-7a-5p for the mature miR 5' to 3' strand as set forth in accession number MIMAT0000062; and hsa-miR-let-7a-3p for the 3' to 5' complementary strand of a duplex miR-129 molecule as set forth by accession number MIMAT0004481. MiR-let-7 is well known and has been studied in detail, e.g., Kasashima K, et al., *Biochem Biophys Res Commun.* 322 pp. 403-410 (2004). As stated above for exemplary modified microRNAs described herein, methods for creating a miR-let-7 mimics are known by those of ordinary skill in the art. Unless otherwise stated, all such modified miR-let-7 nucleic acid forms are herein considered to be within the scope of the term "miR-let-7 mimic", as used herein.

Generally, a modified miR-let-7 (i.e., miR-let-7 mimic) contains no more than one, two, three, four, or five additional nucleotides covalently appended to the miR-let-7 native sequence, wherein the additional bases are independently selected from C, U, G, and C, or the additional bases may be exclusively U. Typically, the miR-let-7 mimic is used in single-strand form, but double-stranded versions are also considered herein.

In some embodiments, at least one of the U bases in the miR-let-7 sequence, whether in the native and/or in an appended portion, is a 5-halouracil. The 5-halouracil can be, for example, 5-fluorouracil, 5-chlorouracil, 5-bromouracil, or 5-iodouracil.

In another set of embodiments, precisely one of the U bases in the miR-let-7 mimic sequence is a 5-halouracil. In a second set of embodiments, precisely or at least two U bases in the miR-let-7 sequence are 5-halouracils. In another set of embodiments, precisely or at least three U bases in the miR-let-7 oligonucleotide sequence are 5-halouracils. In other embodiments, precisely or at least four U bases in the miR-let-7 sequence are 5-halouracils. In other embodiments, precisely or at least five U bases in the miR-let-7 sequence are 5-halouracils. In other embodiments, precisely or at least six U bases in the miR-let-7 sequence are 5-halouracils. In other embodiments, precisely or at least seven U bases in the miR-let-7 sequence are 5-halouracils. In specific embodiments, all of the U bases in the miR-let-7 sequence, whether in the native and/or in an appended portion, are 5-halouracils.

In an exemplary embodiment, the nucleic acid composition of the present disclosure has a modified miR-let-7 nucleotide sequence of $U^FGAGGU^FAGU^FAGGU^FU^FGU^FAU^FAGU^FU^F$ [SEQ ID NO. 30], wherein $U^F$ is a halouracil, specifically 5-fluorouracil.

The U bases that are replaced by 5-halouracils in the miR-let-7 mimic sequence may be located in an unmodified part of the miR-let-7 sequence, as provided above, or may be located in one or more uracil bases that are appended to the native miR-let-7 sequence, as provided above.

In other embodiments, a seed portion of the native miR-let-7 nucleotide sequence remains unmodified with a 5-halouracil while one or more (or all) of the remaining U bases in the remainder of the miR-let-7 nucleotide sequence (non-seed portion) are replaced by a 5-halouracil or combination thereof.

The modified microRNA nucleic acid compositions described herein can be synthesized using any of the well known methods for synthesizing nucleic acids. In particular embodiments, the nucleic acid compositions are produced by automated oligonucleotide synthesis, such as any of the well-known processes using phosphoramidite chemistry. To introduce one or more 5-halouracil bases in a modified miR sequence (e.g., miR-15a sequence, miR-140 sequence, miR-192 sequence, miR-502 sequence, miR-506 sequence, miR-34 sequence, miR-200a sequence, miR-200b sequence, miR-200c sequence, miR-145 sequence, miR-194 sequence, or the miR-let-7 sequence), a 5-halouracil nucleoside phosphoramidite can be included as a precursor base, along with the phosphoramidite derivatives of nucleosides containing natural bases (e.g., A, U, G, and C) to be included in the nucleic acid sequence.

In some embodiments, the nucleic acid compositions of the present disclosure may be produced biosynthetically, such as by using in vitro RNA transcription from plasmid, PCR fragment, or synthetic DNA templates, or by using recombinant (in vivo) RNA expression methods. See, e.g., C. M. Dunham et al., *Nature Methods*, (2007) 4(7), pp. 547-548. The modified microRNA sequences of the present disclosure (e.g., miR-15a sequence, miR-140 sequence, miR-192 sequence, miR-502 sequence, miR-506 sequence, miR-34 sequence, miR-200a sequence, miR-200b sequence, miR-200c sequence, miR-145 sequence, miR-194 sequence, or the miR-let-7 nucleotide sequence) may be further chemically modified such as by functionalizing with polyethylene glycol (PEG) or a hydrocarbon or a targeting agent, particularly a cancer cell targeting agent, such as folate, by techniques well known in the art. To include such groups, a reactive group (e.g., amino, aldehyde, thiol, or carboxylate group) that can be used to append a desired functional group may first be included in the oligonucleotide sequence. Although such reactive or functional groups may be incorporated onto the as-produced nucleic acid sequence, reactive or functional groups can be more facilely included by using an automated oligonucleotide synthesis in which non-nucleoside phosphoramidites containing reactive groups or reactive precursor groups are included.

Modified Nucleic Acid Formulations

The present disclosure reveals that the modified microRNAs each exhibit a potent efficacy as an anti-cancer therapeutic. Notably, each of the modified microRNA nucleic acid compositions tested reduce cancer cell proliferation, tumor growth and development in a dose dependent manner by inducing cell-cycle arrest in all six cancer types examined.

As such, the present disclosure is also directed to formulations of the modified microRNA nucleic acid compositions described herein. For example, the present nucleic acid compositions can be formulated for pharmaceutical uses. In certain embodiments, a formulation is a pharmaceutical composition containing a nucleic acid composition described herein and a pharmaceutically acceptable carrier. In other embodiments, a formulation of the present disclosure comprises a modified miR-129 nucleic acid, a modified miR-15a nucleic acid, a modified miR-140 nucleic acid, a modified miR-192 nucleic acid, a modified miR-502, a modified miR-506 nucleic acid, a modified miR-34 nucleic acid, a modified miR-200a nucleic acid, a modified miR-200b, a modified miR-200c nucleic acid, a modified miR-194 nucleic acid, a modified miR-let-7 nucleic acid, or a combination thereof and a pharmaceutically acceptable carrier.

More specifically, one or more of the modified microRNA nucleic acids set forth in the following nucleotide sequences can be formulated for pharmaceutical application and use; $CU^FU^FU^FU^FU^FGCGGU^FCU^FGGGCU^FU^FGC$ [SEQ ID NO. 4], CUUUUUGCGGU$^F$CU$^F$GGGCU$^F$U$^F$GC [SEQ ID NO. 5], U$^F$AGCAGCACAU$^F$AAU$^F$GGU$^F$U$^F$U$^F$GU$^F$G [SEQ ID NO. 6], UAGCAGCACAU$^F$AAU$^F$GGU$^F$U$^F$U$^F$GU$^F$G [SEQ ID NO. 7], CAGU$^F$GGUUUUA CCCU$^F$AUGGU$^F$AG [SEQ ID NO. 9], CU$^F$ GACCU$^F$AU$^F$GAAU$^F$U$^F$GACAGCC [SEQ ID NO. 11], AU$^F$CCU$^F$U$^F$GCUAU$^F$CU$^F$GGGU$^F$GCU$^F$A [SEQ ID NO. 13], U$^F$AU$^F$U$^F$CAGGAAGGU$^F$GU$^F$U$^F$ACU$^F$U$^F$AA [SEQ ID NO. 15], CAGU$^F$GGU$^F$U$^F$U$^F$U$^F$ACCCU$^F$AU$^F$GGU$^F$AG [SEQ ID NO. 16], U$^F$GGCAGU$^F$GU$^F$CU$^F$U$^F$AGCU$^F$GGU$^F$U$^F$GU$^F$ [SEQ ID NO. 18], U$^F$AACA-CU$^F$GU$^F$CU$^F$GGU$^F$AACGAU$^F$GU$^F$ [SEQ ID NO. 20], U$^F$AAU$^F$ACU$^F$GCCU$^F$GGU$^F$AAU$^F$GAU$^F$GA [SEQ ID NO. 22], U$^F$AAU$^F$ACU$^F$GCCGGGU$^F$AAU$^F$GAU$^F$GGA [SEQ ID NO. 24], GU$^F$CCAGU$^F$U$^F$U$^F$U$^F$CCCAG-GAAU$^F$CCCU$^F$ [SEQ ID NO. 26], U$^F$GU$^F$AACAGCAA-CU$^F$CCAU$^F$GU$^F$GGA [SEQ ID NO. 28], U$^F$GAGGU$^F$-AGU$^F$AGGU$^F$U$^F$GU$^F$AU$^F$AGU$^F$U [SEQ ID NO. 30].

The term "pharmaceutically acceptable carrier" is used herein as synonymous with a pharmaceutically acceptable diluent, vehicle, or excipient. Depending on the type of pharmaceutical composition and intended mode of administration, the nucleic acid composition may be dissolved or suspended (e.g., as an emulsion) in the pharmaceutically acceptable carrier. The pharmaceutically acceptable carrier can be any of those liquid or solid compounds, materials, compositions, and/or dosage forms which are, within the scope of sound medical judgment, suitable for use in contact with tissues of a subject. The carrier should be "acceptable" in the sense of being not injurious to the subject it is being provided to and is compatible with the other ingredients of the formulation, i.e., does not alter their biological or chemical function.

Some, non-limiting examples, of materials which can serve as pharmaceutically acceptable carriers include: sugars, such as lactose, glucose and sucrose; starches, such as corn starch and potato starch; cellulose and its derivatives, such as sodium carboxymethyl cellulose, ethyl cellulose and cellulose acetate; gelatin; talc; waxes; oils, such as peanut oil, cottonseed oil, safflower oil, sesame oil, olive oil, corn oil and soybean oil; glycols, such as ethylene glycol and propylene glycol; polyols, such as glycerin, sorbitol, mannitol and polyethylene glycol; esters, such as ethyl oleate and ethyl laurate; agar; buffering agents; water; isotonic saline; pH buffered solutions; and other non-toxic compatible substances employed in pharmaceutical formulations. The pharmaceutically acceptable carrier may also include a manufacturing aid (e.g., lubricant, talc magnesium, calcium or zinc stearate, or stearic acid), a solvent, or encapsulating material. If desired, certain sweetening and/or flavoring and/or coloring agents may be added. Other suitable excipients can be found in standard pharmaceutical texts, e.g. in "Remington's Pharmaceutical Sciences", The Science and Practice of Pharmacy, 19$^{th}$ Ed. Mack Publishing Company, Easton, Pa., (1995).

In some embodiments, the pharmaceutically acceptable carrier may include diluents that increase the bulk of a solid pharmaceutical composition and make the pharmaceutical dosage form easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

The nucleic acid compositions of the present disclosure may be formulated into compositions and dosage forms according to methods known in the art. In certain embodiments, the formulated compositions may be specially formulated for administration in solid or liquid form, including those adapted for the following: (1) oral administration, for example, tablets, capsules, powders, granules, pastes for application to the tongue, aqueous or non-aqueous solutions or suspensions, drenches, or syrups; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

In some embodiments, the formulations of the present disclosure include a solid pharmaceutical agent that is compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in a subject's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Therefore, in certain embodiments, glidants can be added to formulations to improve the flowability of a non-compacted solid agent and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

A formulated pharmaceutical composition for tableting or capsule filling can be prepared by wet granulation. In wet granulation, some or all of the active ingredients and excipients in powder form are blended and then further mixed in the presence of a liquid, typically water that causes the powders to clump into granules. The granulate is screened and/or milled, dried and then screened and/or milled to the desired particle size. The granulate may then be tableted, or other excipients may be added prior to tableting, such as a glidant and/or a lubricant. A tableting composition may be prepared conventionally by dry blending. For example, the blended composition of the actives and excipients may be compacted into a slug or a sheet and then comminuted into compacted granules. The compacted granules may subsequently be compressed into a tablet.

In other embodiments, as an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting. A capsule filling may include any of the aforementioned blends and granulates that were described with reference to tableting; however, they are not subjected to a final tableting step In liquid pharmaceutical compositions of the present disclosure, the agent and any other solid excipients are dissolved or suspended in a liquid carrier such as water, water-for-injection, vegetable oil, alcohol, polyethylene glycol, propylene glycol or glycerin. Liquid pharmaceutical compositions may contain emulsifying agents to disperse uniformly throughout the composition an active ingredient or other excipient that is not soluble in the liquid carrier. The liquid formulation may be used as an injectable, enteric, or emollient type of formulation. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

In some embodiments, liquid pharmaceutical compositions of the present disclosure may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum. In other embodiments, the liquid composition of the present disclosure may also contain a buffer, such as gluconic acid, lactic acid, citric acid or acetic acid, sodium gluconate, sodium lactate, sodium citrate, or sodium acetate.

Sweetening agents, such as sorbitol, saccharin, sodium saccharin, sucrose, aspartame, fructose, mannitol and invert sugar, may be added to certain formulations of the present disclosure to improve the taste. Flavoring agents and flavor enhancers may make the dosage form more palatable to the patient. Common flavoring agents and flavor enhancers for pharmaceutical products that may be included in the composition of the present disclosure include maltol, vanillin, ethyl vanillin, menthol, citric acid, fumaric acid, ethyl maltol and tartaric acid.

Preservatives and chelating agents, such as alcohol, sodium benzoate, butylated hydroxy toluene, butylated hydroxyanisole and ethylenediamine tetraacetic acid, may be added at levels safe for ingestion to improve storage stability. Solid and liquid compositions may also be dyed using any pharmaceutically acceptable colorant to improve their appearance and/or facilitate patient identification of the product and unit dosage level.

A dosage formulation of the present disclosure may be a capsule containing the composition, for example, a powdered or granulated solid composition of the disclosure, within either a hard or soft shell. The shell may be made from gelatin and optionally contain a plasticizer such as glycerin and sorbitol, and an opacifying agent or colorant.

Methods for Treating Cancer

As stated above, the modified microRNA nucleic acid compositions of the present disclosure and formulations thereof show unexpected and exceptional anticancer activity when compared to that exhibited by exogenous expression of a corresponding unmodified native microRNA and/or a known cancer therapy (chemotherapy), such as 5-FU. Therefore, another aspect of the present disclosure provides a method for treating cancer in a mammal by administering to the mammal an effective amount of one or more of the modified microRNA nucleic acid compositions of the present disclosure, or formulations thereof.

Figure 8A:
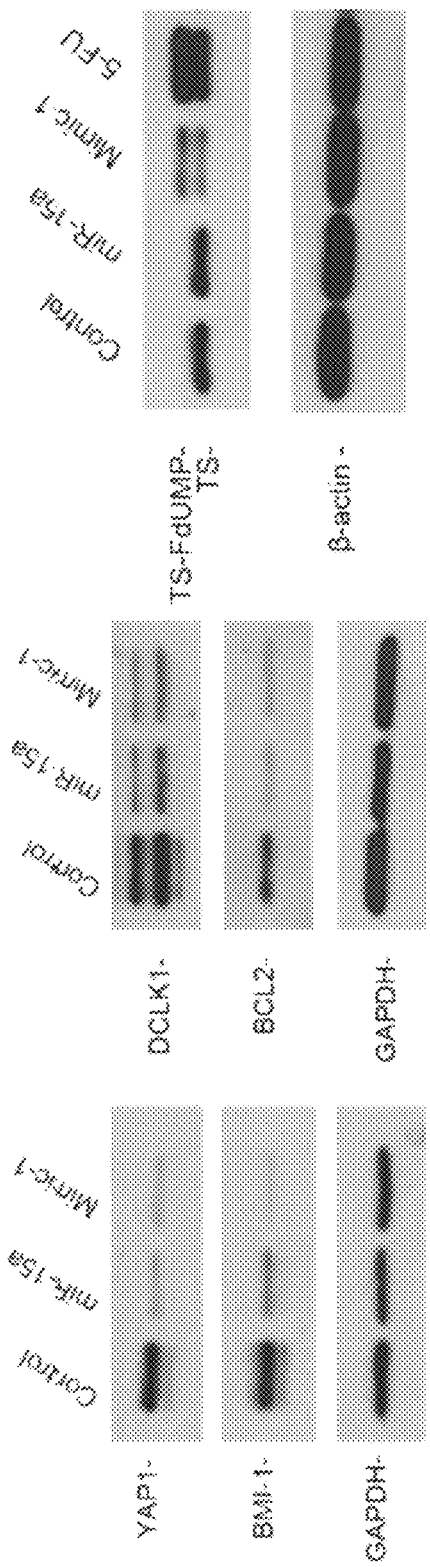
FIGS. 8A-8B. Anti cancer activity of a second exemplary modified microRNA of the present disclosure. (A) Representative western blots comparing the ability of exogenously expressed unmodified miR-15a (miR-15a) and a modified miR-15a nucleic acid composition (mimic-1) to modulate protein expression in colon cancer cells. Modified miR-15a, as set forth in SEQ ID NO: 6 (mimic-1) retains the ability to regulate miR-15a targets (YAP1, BMI-1, DCLK1 and ECL2) and break downs TS-FdUMP in colorectal cancer cells. (B) Modified miR-15a (mimic-1) showed enhanced ability to inhibit colon cancer cell proliferation in three different colorectal cancer cell lines (HCT116, RKO, SW620) compared to exogenously expressed unmodified miR-15a (miR-15a).

As shown in FIGS. 2A and 8A, exemplary modified microRNA nucleic acids of the present disclosure, i.e., modified miR-15a and modified MiR-129 suppress BCL2 expression and activity in the cancer cells of a subject, which results in an increased amount of available pro-apoptotic proteins which ultimately leads to increased cancer cell death. miR-129, for example, regulates apoptosis by directly targeting BCL2 as well as by impacting other critical cell death-related proteins. Further, FIG. 2A shows that miR-129 reduces the expression, and thus activity of E2F3, a transcription factor protein that regulates cell cycle progression and reduces the expression or activity of thymidylate synthase (TS) protein levels, which results in increased cellular proliferation and increased efficacy of chemotherapeutic agents.

Figure 3:
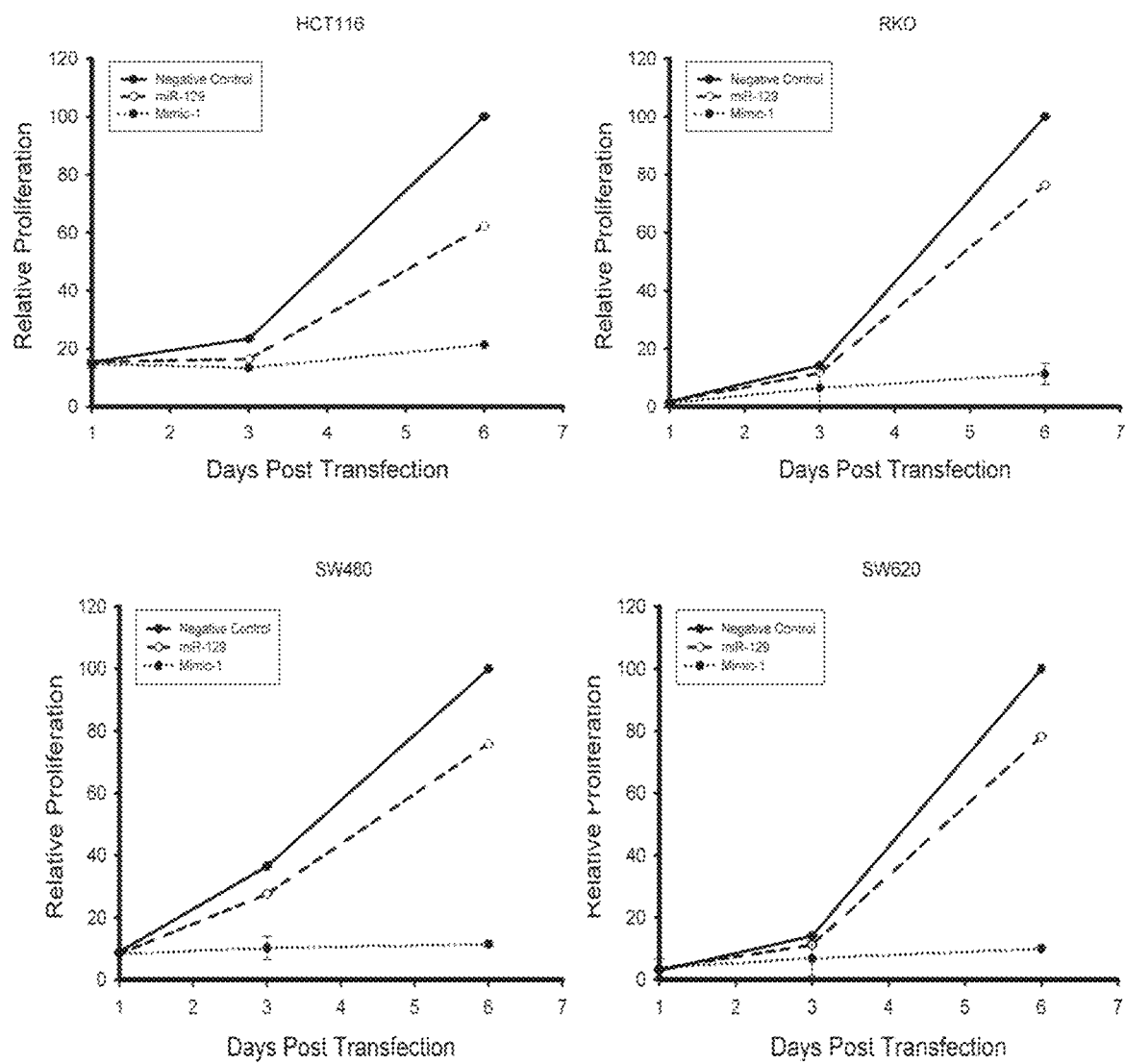
FIG. 3. Graphs showing inhibition of colon cancer cell proliferation in 4 different colon cancer cell lines (HCT116, RKO, SW480 and SW620) by an exemplary modified microRNA (mimic). An exemplary modified miR-129 nucleic acid having all U bases replaced by 5-flurouracil (-●-), as compared to a non-specific (Negative control, ●) control and exogenously expressed native miR-129 (○).

Furthermore and as shown in FIGS. 12A-12D, 13A-13B and 14A-14, all of the exemplary modified microRNA's modulate cancer cell proliferation and induce cancer cell apoptosis. More specifically, modified miR-15a has been shown to reduce cancer cell proliferation across the following experimental models, pancreatic cancer cells (FIGS. 12A-12B and 14A), lung cancer (FIGS. 12D and 14D), colorectal cancer (FIG. 8B), gastric cancer (FIG. 14B), breast cancer (FIG. 14C), and blood cancer, i.e., leukemia (FIG. 14E). Furthermore, modified miR-129 has been shown to reduce cancer cell proliferation across the following experimental models, pancreatic cancer cells (FIG. 14A), lung cancer (FIGS. 12C and 14D), colorectal cancer (FIG. 3), gastric cancer (FIG. 14B), breast cancer (FIG. 14C), and blood cancer, i.e., leukemia (FIG. 14E). Modified miR-192 and modified miR-140 have also shown an ability to reduce cancer cell proliferation across the following experimental models, pancreatic cancer cells (FIG. 14A), lung cancer (FIG. 14D), colorectal cancer (FIGS. 13A-13B), gastric cancer (FIG. 14B), breast cancer (FIG. 14C), and blood cancer, i.e., leukemia (FIG. 14E). Moreover, each modified microRNAs of the present disclosure (i.e., modified miR-129, miR-15a, miR-192, miR-215, miR-140, miR-502, miR-506, miR-34, miR-200a, miR-200b, miR-200c, miR-145, miR-194 and miR-let-7) inhibits cancer cell proliferation in all of the following experimental cancer models: pancreatic cancer (FIG. 14A), gastric cancer (FIG. 14B), breast cancer (FIG. 14C), lung cancer (FIG. 14D), and blood cancer (FIG. 14E).

Figure 7:
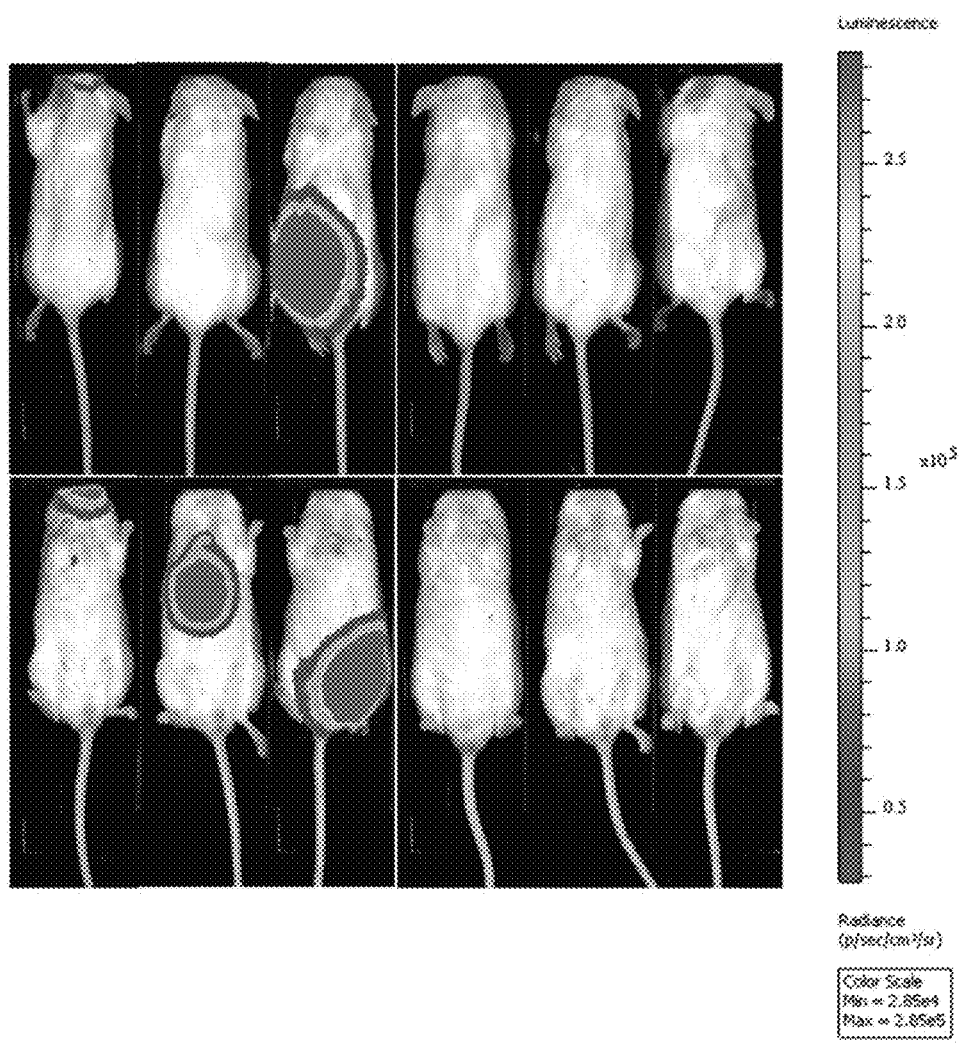
FIG. 7. In vivo systemic treatment with exemplary modified microRNA nucleic acid compositions inhibits colon cancer metastasis without toxic side effects. A colon cancer metastasis mouse model was established via tail vein injection of metastatic human colon cancer cells. Two weeks after establishing metastasis, 40 μg of a modified miR-129 nucleic acid composition, as set forth in SEQ ID NO: 4 was delivered by intravenous injection with a treatment frequency of one injection every other day for two weeks. The exemplary modified miR-129 nucleic acid (mimic) was able to inhibit colon cancer metastasis (right panels) while negative control miRNA (left panels) had no effect. Mice treated with modified miR-129 nucleic acid did not exhibit any toxicity.
Figure 11:
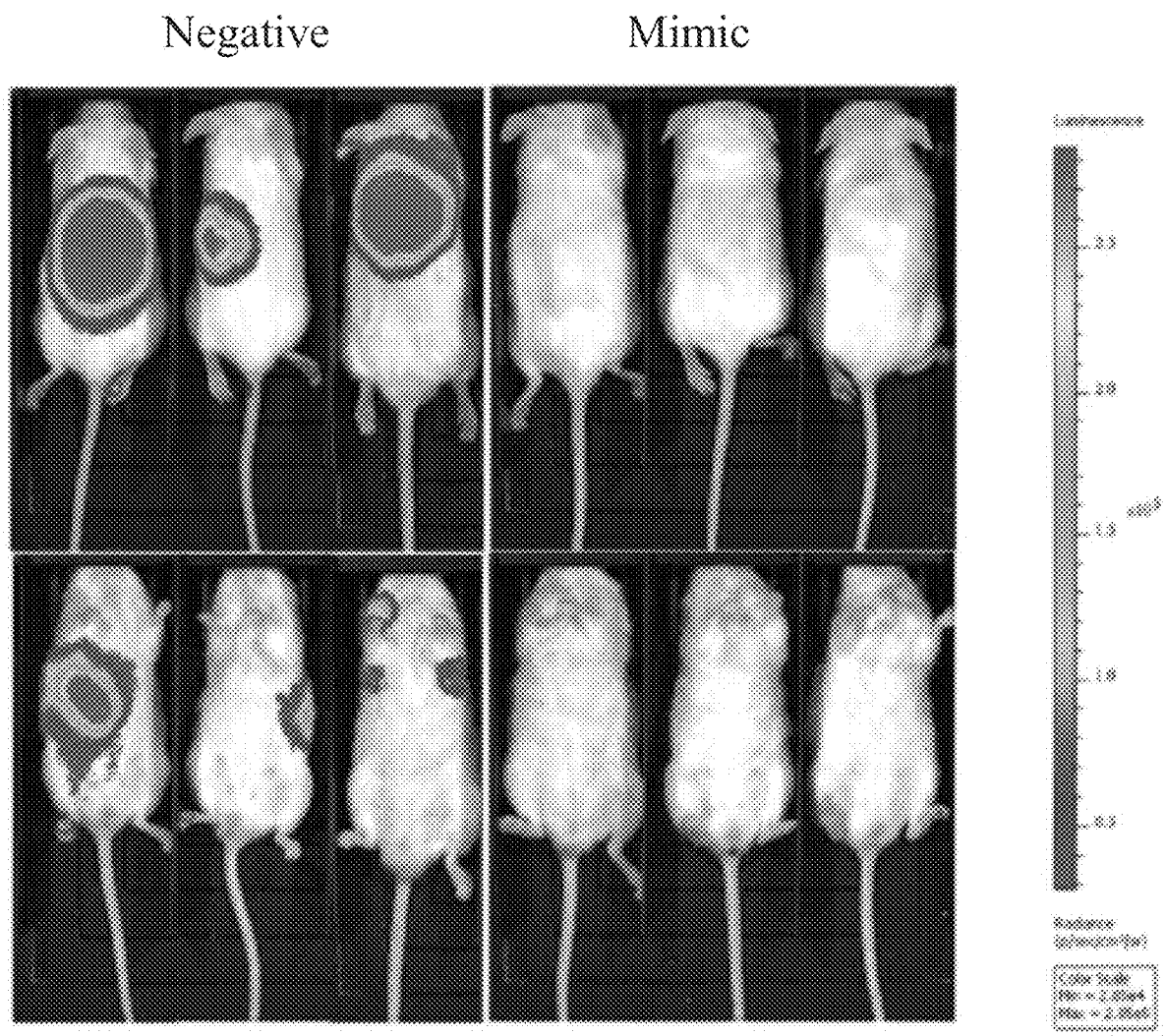
FIG. 11. Other exemplary modified microRNAs exhibit efficacy as an anti-cancer agent in vivo. A colon cancer metastasis mouse model was established via tail vein injection of metastatic human colon cancer cells. Two weeks after establishing the metastasis, 40 μg of a modified miR-15a nucleic acid composition as set forth in SEQ ID NO: 6 was delivered by intravenous injection with treatment frequency of one injection every other day for two weeks. The exemplary modified miR-15a nucleic acid (mimic) was able to inhibit colon cancer metastasis while negative control miRNA (negative) had no effect. Mice treated with modified miR-15a nucleic acid did not exhibit any toxicity.
Figure 12A:
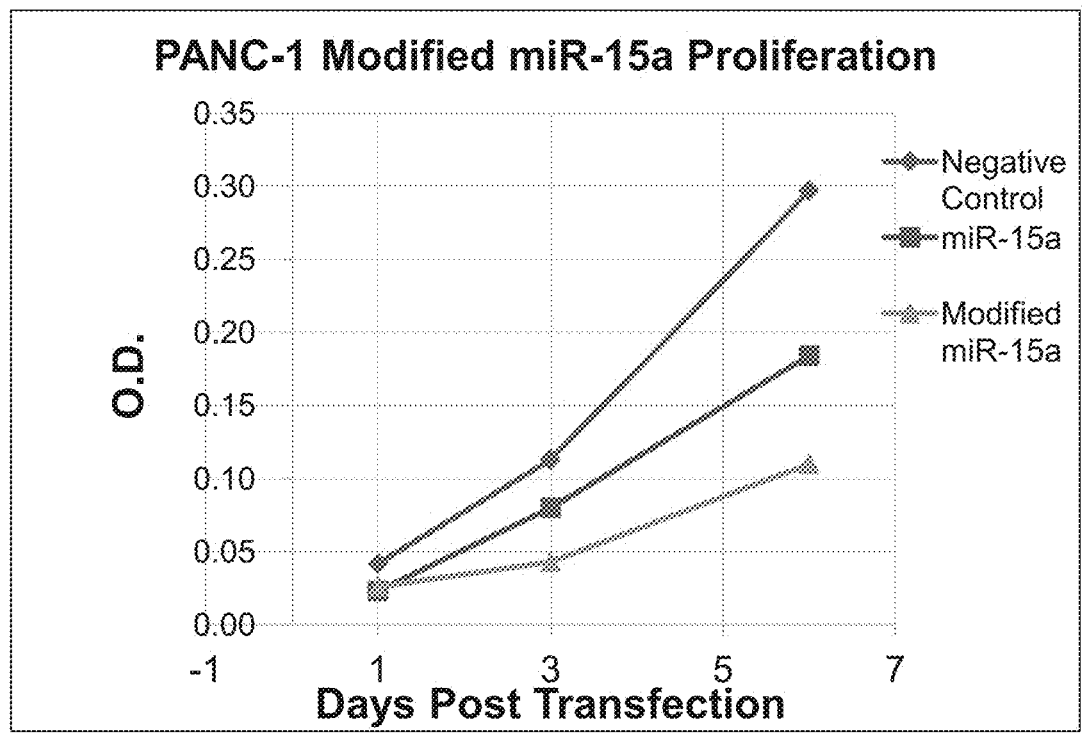
FIGS. 12A-12D. Exemplary modified miR-15a and miR-129 mimics of the present disclosure exhibit enhanced ability to inhibit human breast cancer (A549; C,D) and pancreatic cancer (Panc-1(A); AsPC-1(B)) cell proliferation compared to unmodified miR-15a (miR-15a) or unmodified miR-129 (miR-129) or cells treated with negative controls.
Figure 12B:
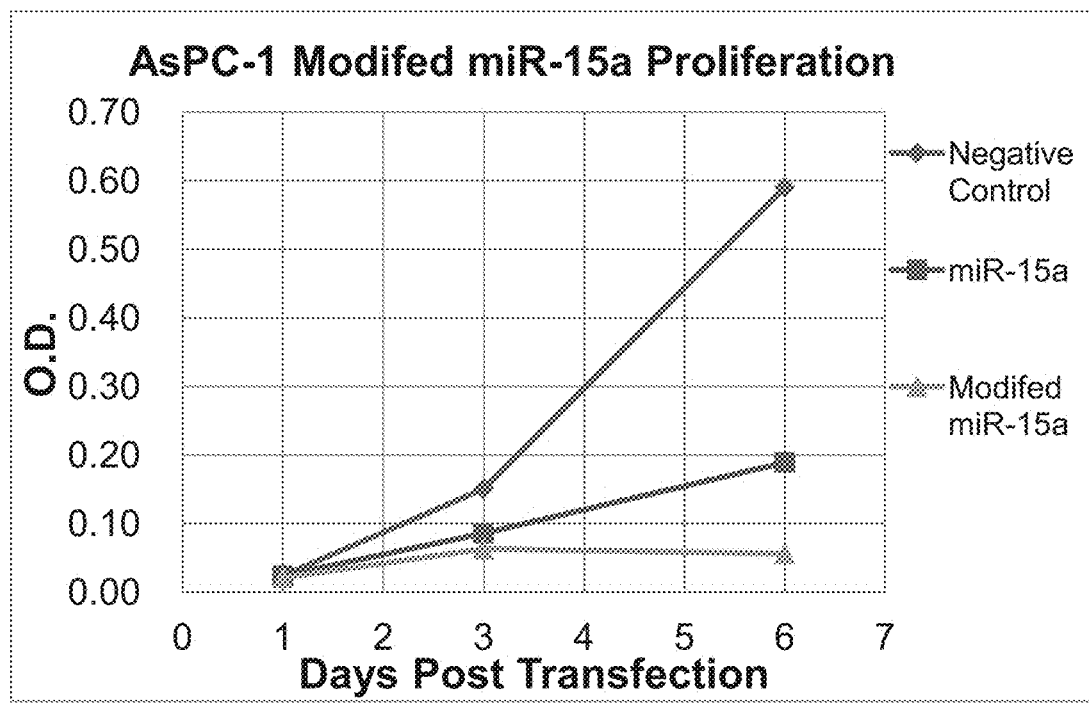
Figure 12C:
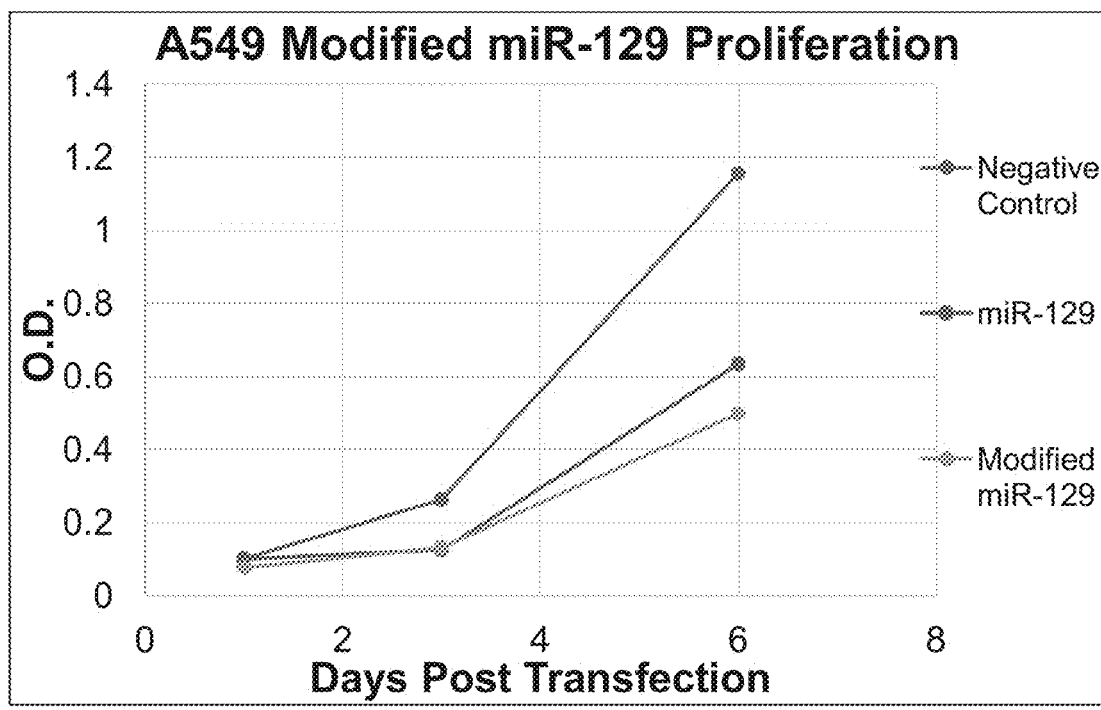
Figure 12D:
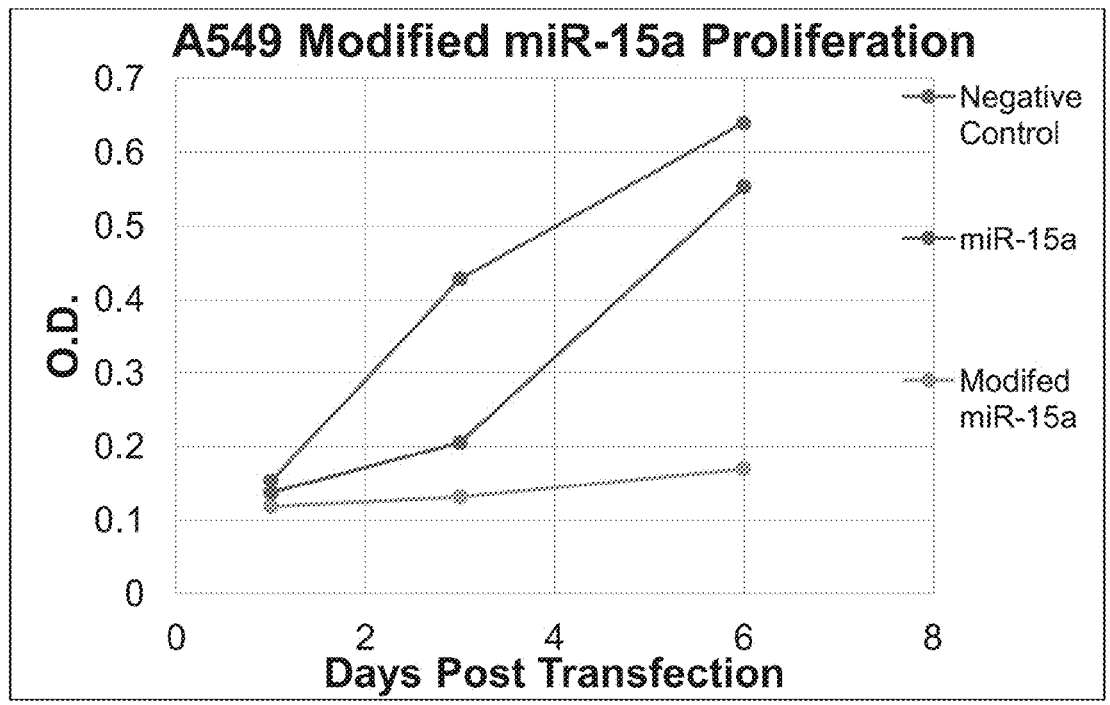

In addition, the present modified miR compositions were tested and found to be therapeutically effective in vivo. For example, FIGS. 7 and 11 show that intravenous treatment with two exemplary modified microRNA's of the present disclosure (e.g., modified miR-129 and modified miR-15a) effectively treat cancer (e.g., colorectal cancer) by inhibiting tumor growth and development in vivo.

Therefore, the disclosed methods for treating cancer include administering one or more modified nucleic acid compositions of the present disclosure (e.g., a modified microRNA, such as modified miR-129 nucleic acid, a modified miR-15a nucleic acid, a modified miR-140 nucleic acid, a modified miR-192 nucleic acid, a modified miR-502, a modified miR-506 nucleic acid, a modified miR-34 nucleic acid, a modified miR200a nucleic acid, a modified miR-200b nucleic acid, a modified miR-200c nucleic acid, a modified miR-145 nucleic acid, a modified miR-194 nucleic acid, a modified miR-let-7 nucleic acid or a combination thereof) to a subject. In certain embodiments, the nucleic acid composition can be administered as a formulation that includes a nucleic acid composition and one or more pharmaceutical carriers.

In specific embodiments, the nucleic acid compositions of the present disclosure can be administered in the absence of a delivery vehicle or pharmaceutical carrier (i.e., naked). See, for example, FIGS. 17A-17B.

The term "subject" as used herein refers to any mammal. The mammal can be any mammal, although the methods herein are more typically directed to humans. The phrase "subject in need thereof" as used herein is included within the term subject and refers to any mammalian subject in need of a treatment, particularly cancer or has a medically determined elevated risk of a cancerous or pre-cancerous condition. In specific embodiments, the subject includes a human cancer patient.

In some embodiments, the human subject has colorectal cancer or has a medically determined elevated risk of getting colorectal cancer.

In other embodiments, the subject has pancreatic cancer, or has a medically determined elevated risk of getting pancreatic cancer such as, for example, being diagnosed with chronic pancreatitis.

In certain embodiments, a subject of the present disclosure has breast cancer, or has a medically determined elevated risk of getting breast cancer. In specific embodiments, the breast cancer is triple negative breast cancer, ductal carcinoma or lobal carcinoma.

In some embodiments, the subject has blood cancer or has a medically determined elevated risk of getting blood cancer. In a specific embodiment, the blood cancer is a leukemia. In one embodiment, the leukemia is acute lymphocytic leukemia.

In other embodiments, the subject has gastric cancer, or has a medically determined elevated risk of getting gastric cancer. In one embodiment, the gastric cancer being treated is stomach cancer.

The terms "treatment" "treat" and "treating" are synonymous with the term "to administer an effective amount". These terms shall mean the medical management of a subject with the intent to cure, ameliorate, stabilize, reduce one or more symptoms of or prevent a disease, pathological condition, or disorder such as cancer. These terms, are used interchangeably and include the active treatment, that is, treatment directed specifically toward the improvement of a disease, pathological condition, or disorder, and also include causal treatment, that is, treatment directed toward removal of the cause of the associated disease, pathological condition, or disorder. In addition, treating includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, ameliorization, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount. In a specific embodiment, treatment of a disease, such as a cancer includes inhibiting proliferation of cancer cells. In some embodiments, the treatment of a cancer can be determined by detecting a reduction in the amount of proliferating cancer cells in a subject, a reduction in tumor growth or tumor size.

In certain embodiments, the nucleic acid compositions of the present disclosure are used to treat cancer.

The term "cancer", as used herein, includes any disease caused by uncontrolled division and growth of abnormal cells, including, for example, the malignant and metastatic growth of tumors. The term "cancer" also includes precancerous conditions or conditions characterized by an elevated risk of a cancerous or pre-cancerous condition. The cancer or pre-cancer (neoplastic condition) can be located in any part of the body, including the internal organs and skin. As is well known, cancer spreads through a subject by invading the normal, non-cancerous tissue surrounding the tumor, via the lymph nodes and vessels, and by blood after the tumor invades the veins, capillaries and arteries of a subject. When cancer cells break away from the primary tumor ("metastasize"), secondary tumors arise throughout an afflicted subject forming metastatic lesions.

Some non-limiting examples of applicable cancer cells for treatment using the present methods include the colon, rectum (including anus), stomach, esophageal, kidney, prostate, skin, lungs, breast, pancreas, brain, blood, and liver. The cancer or neoplasm can also include the presence of one or more carcinomas, sarcomas, lymphomas, blastomas, or teratomas (germ cell tumors). In some embodiments, the cancer may also be a form of leukemia.

In particular embodiments, the nucleic acid compositions described herein are used to treat colorectal (i.e., colon or rectal), pancreatic, breast, gastric, lung or blood cancer in any of their stages, as further described below.

For example, there are four stages of colorectal cancer, which are generally characterized by the degree of metastasis. In Stage 0 or carcinoma in situ, abnormal potentially cancerous cells are found in the mucosa (innermost layer) of the colon wall. In Stage I, cancerous cells have formed in the mucosa of the colon wall and have spread to the submucosa (layer of tissue under the mucosa) and may have spread to the muscle layer of the colon wall. Stage II is composed of three subclasses: Stage IIA, wherein the cancerous tissue has spread through the muscle layer of the colon wall to the serosa (outermost layer) of the colon wall, Stage IIB, wherein the tumor has spread through the serosa of the colon wall but has not spread to nearby organs; and Stage IIC, wherein the cancer has spread through the serosa of the colon wall and invaded nearby organs. Stage III is also divided into three subclasses: Stage IIIA, wherein the cancer may have spread through the mucosa of the colon wall to the submucosa and muscle layer, and has spread to one to three nearby lymph nodes or tissues near the lymph nodes; or the cancer has spread through the mucosa to the submucosa and four to six nearby lymph nodes; Stage IIIB, wherein the tumor has spread through the muscle layer of the colon wall to the serosa or has spread through the serosa but not to nearby organs and the cancer has spread to one to three nearby lymph nodes or to tissues near the lymph nodes, or has spread to the muscle layer or to the serosa, and to four to six nearby lymph nodes; or has spread through the mucosa to the submucosa and may have spread to the muscle layer and has spread to seven or more nearby lymph nodes. In Stage IIIC colorectal cancer, the tumor has spread through the serosa of the colon wall but not to nearby organs and the cancer has spread to four to six nearby lymph nodes; or the cancer has spread through the muscle layer to the serosa or has spread through the serosa but not to nearby organs and the cancer has spread to seven or more nearby lymph nodes, or the cancer has spread through the serosa to nearby organs and to one or more nearby lymph nodes or to tissues near the lymph nodes. Finally, Stage IV colon cancer is divided into two subclasses: Stage IVA, wherein the cancer has spread through the colon wall and into nearby organs and one organ that is not near the colon or to a distant lymph node; and Stage IVB, wherein the cancer has spread through the colon wall and into nearby organs and more than one organ that is not near the colon or into the lining of the abdominal wall.

Yet another example of tumor staging includes the Dukes classification system for colorectal cancer. Here, the stages are identified as Stage A, wherein the tumor is confined to the intestinal wall; Stage B, wherein the tumor exhibits invasion through the bowel but has not invaded the lymph nodes; Stage C, wherein cancerous cells or tissue is found within the lymph nodes of a subject; and Stage D, wherein the tumor exhibits widespread metastases into several organs of the subject.

The Astler Coller classification system may alternatively be used. Here, Stage A colorectal cancer is identified as cancer that is only present in the mucosa of the intestine; Stage B1 whereby the tumor extends into muscularis propria but does not penetrate through it and the tumor has not metastasized into the lymph nodes, Stage B2 colorectal cancer is denoted by a tumor that penetrates through muscularis propria and the tumor has not metastasized into the lymph nodes; Stage C1 is characterized by a tumor that extends into muscularis propria, but does not penetrate through it and the tumor has metastasized into the lymph nodes; Stage C2 colorectal cancer is classified as a tumor that penetrates through the muscularis propria where the tumor has metastasized into the lymph nodes; and Stage D describes a tumor that has metastasized throughout the organism or subject.

In some embodiments, the treatment methods of the present disclosure are more particularly directed to cancer subjects exhibiting reduced levels of miR-129 expression, miR-15a expression, miR-506 expression, miR-502, miR-140 or a combination thereof. In this respect, it is known that miR-15a is down-regulated in cancers. See, for example, R I Aqeilan, et al., *Cell Death and Differentiation* (2010) 17, pp. 215-220. Further, it is known that cancerous cells having reduced levels of miR-129 expression are resistant to 5-fluorouracil, as described, e.g., in U.S. Application Pub. No. 2016/0090636, the contents of which are incorporated by reference in their entirety. Additionally, it is known that pancreatic cancer cells exhibit reduced levels of miR-506. See, e.g., Li, J, et al. Oncogene. 35 pp. 5501-5514.

Figures 14A, 14B:
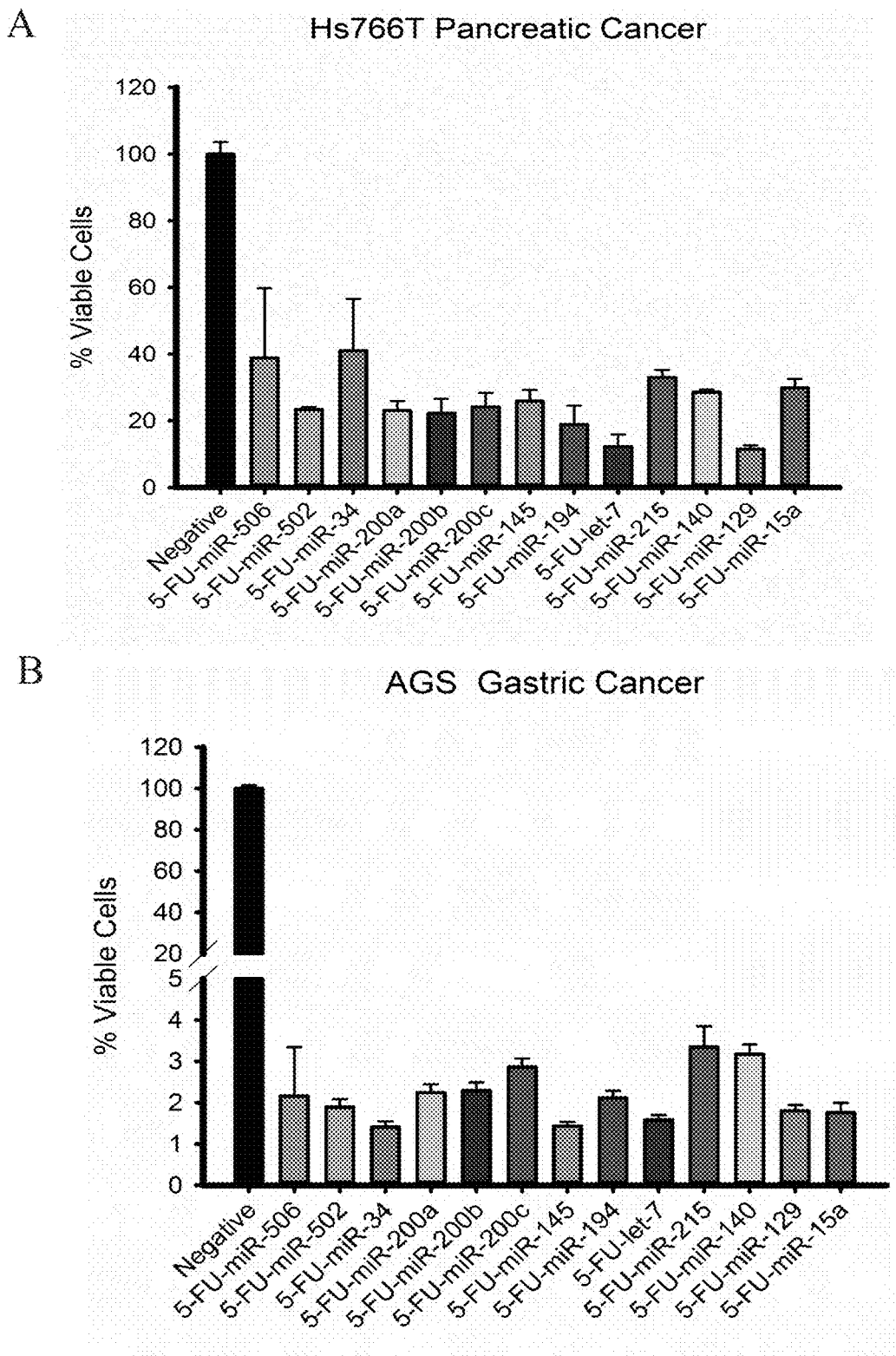
FIGS. 14A-14E. All exemplary modified microRNAs of the present disclosure exhibit an enhanced ability to inhibit several types of cancer. Cancer cell proliferation was inhibited by exogenous expression of each of the following 5-FU-modified microRNA nucleic acids when compared to negative controls (negative), miR-15a [SEQ ID NO: 6], miR-129 [SEQ ID NO: 4], miR-506 [SEQ ID NO: 15], miR-502 [SEQ ID NO: 13], miR-34 [SEQ ID NO: 18], miR-200a [SEQ ID NO: 20], miR-200b [SEQ ID NO: 22], miR-200c [SEQ ID NO: 24], miR-145 [SEQ ID NO: 26], miR-194 [SEQ ID NO: 28], miR-let-7 [SEQ ID NO: 30], miR-215 [SEQ ID NO: 11] and miR-140 [SEQ ID NO: 16] for each of cancer type tested. (A) Human pancreatic cancer cell proliferation is inhibited by expression of each modified microRNA tested in Hs766T pancreatic cancer cells. (B) Gastric cancer cell proliferation is inhibited by expression of each modified microRNA tested in AGS stomach cancer cells. (C) Human breast cancer cell proliferation is inhibited by expression of each modified microRNA tested in SKBR3 breast cancer cells. (D) Lung cancer cell proliferation is inhibited by expression of each modified microRNA tested in A549 lung cancer cells. (E) Leukemia cancer cell proliferation is inhibited by expression of each modified microRNA as tested in an acute lymphocytic leukemia cell line (REH). Taken together, the data reveals that the modified microRNA compositions of the present disclosure display an increased ability to inhibit all types of cancer cell proliferation when compared to negative controls.
Figure 15A:
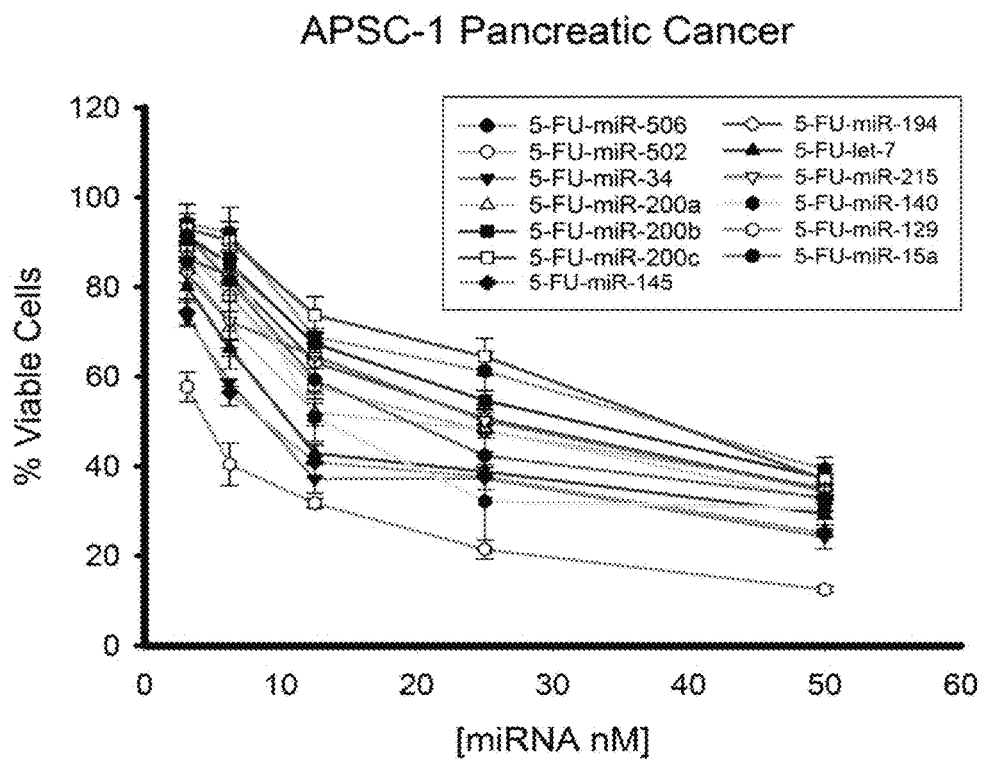
FIGS. 15A-15C. All exemplary modified microRNAs of the present disclosure exhibit displayed the ability to inhibit cancer cell growth in a dose dependent manner. Cancer cell proliferation was inhibited by exogenous expression of each of the following 5-FU-modified microRNA nucleic acids when compared to negative controls (negative), miR-15a [SEQ ID NO: 6], miR-129 [SEQ ID NO: 4], miR-506 [SEQ ID NO: 15], miR-502 [SEQ ID NO: 13], miR-34 [SEQ ID NO: 18], miR-200a [SEQ ID NO: 20], miR-200b [SEQ ID NO: 22], miR-200c [SEQ ID NO: 24], miR-145 [SEQ ID NO: 26], miR-194 [SEQ ID NO: 28], miR-let-7 [SEQ ID NO: 30], miR-215 [SEQ ID NO: 11] and miR-140 [SEQ ID NO: 16] for each of cancer type tested. (A, B) Human pancreatic cancer cell proliferation is inhibited in a dose dependent manner by each modified microRNA tested in two different human pancreatic cancer cell lines (A, APSC-1; B, PANC-1). (C) Leukemia cancer cell proliferation is inhibited in a dose dependent manner by each modified microRNA tested in an acute lymphocytic leukemia cell line (REH). Taken together, the data reveals that the modified microRNA compositions of the present disclosure display an ability to inhibit multiple types of cancer cell growth and proliferation in a dose dependent manner.
Figure 15B:
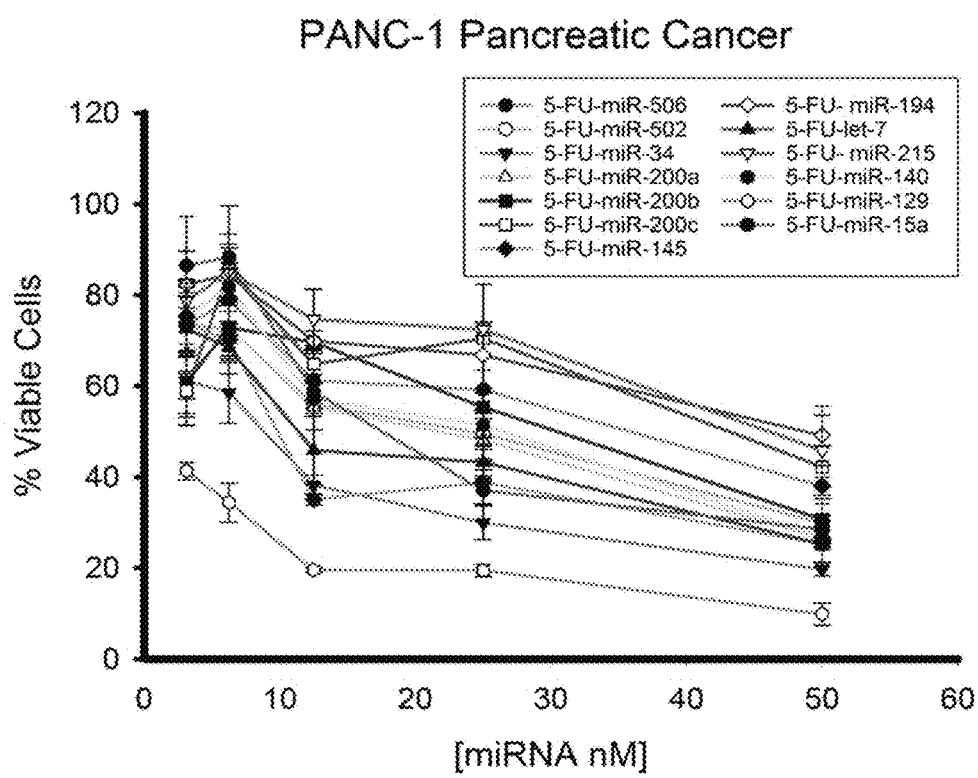

In yet another example, the microRNA mimics of the present disclosure are used to treat pancreatic cancer. As shown in FIGS. 14A and 15A-15B, each of modified miR-129, miR-15a, miR-192, miR-215, miR-140, miR-502, miR-506, miR-34, miR-200a, miR-200b, miR-200c, miR-145, miR-194, and miR-let-7 can be used to treat pancreatic cancer. Pancreatic cancer arises from precursor lesions called pancreatic intraepithelial neoplasia, or PanINs. These lesions are typically located in the small ducts of the exocrine pancreas, and depending on the extent of cytologic atypia may be classified as low-grade dysplasia, moderate dysplasia or high-grade dysplasia lesions. Such lesions typically show that activating mutations in the KRAS gene present, along with certain inactivating mutations in CDKN2A, TP53 and SMAD4. Collectively, these genetic mutations lead to the formation of an infiltrating cancer. Pancreatic cancer is staged based on size of the primary tumor and whether it has grown outside of the pancreas into surrounding organs; whether the tumor has spread to the nearby lymph nodes, and whether it has metastasized to other organs of the body (e.g., liver, lungs, abdomen). This information is then combined and used to provide the specific stage, i.e., 0, 1A, 1B, 2A, 2B, 3 and 4. For stage zero (0), the pancreatic tumor is confined to the top layers of pancreatic duct cells and has not invaded deeper tissues. The primary tumor has not spread outside of the pancreas such as in pancreatic carcinoma in situ or pancreatic intraepithelial neoplasia III. A stage 1A pancreatic tumor is typically confined to the pancreas and is 2 cm across or smaller. Further a stage 1A pancreatic tumor has not spread to nearby lymph nodes or distant sites. A stage 1B pancreatic tumor confined to the pancreas and is larger than 2 cm across. A stage 1B pancreatic tumor has not spread to nearby lymph nodes or distant sites. Stage 2A pancreatic tumors exhibit a tumor growing outside the pancreas but not into major blood vessels or nerves, but the cancer has not spread to nearby lymph nodes or distant sites. A subject exhibiting stage 2B pancreatic cancer presents a tumor is either confined to the pancreas or growing outside the pancreas but not into major blood vessels or nerves, but has spread to nearby lymph nodes. A subject exhibiting stage 3 pancreatic cancer presents a tumor that is growing outside the pancreas into major blood vessels or nerves, but has spread to distant sites. Stage 4 pancreatic cancer has metastasized to distant cites, lymph nodes and organs.

Figure 14C:
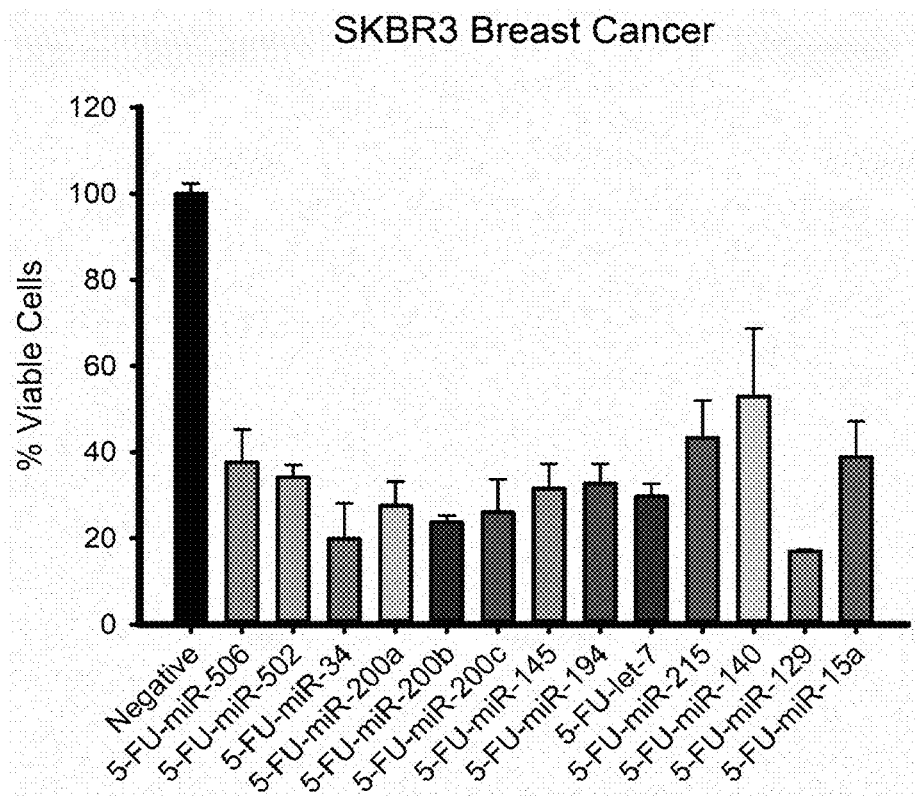
Figure 14D:
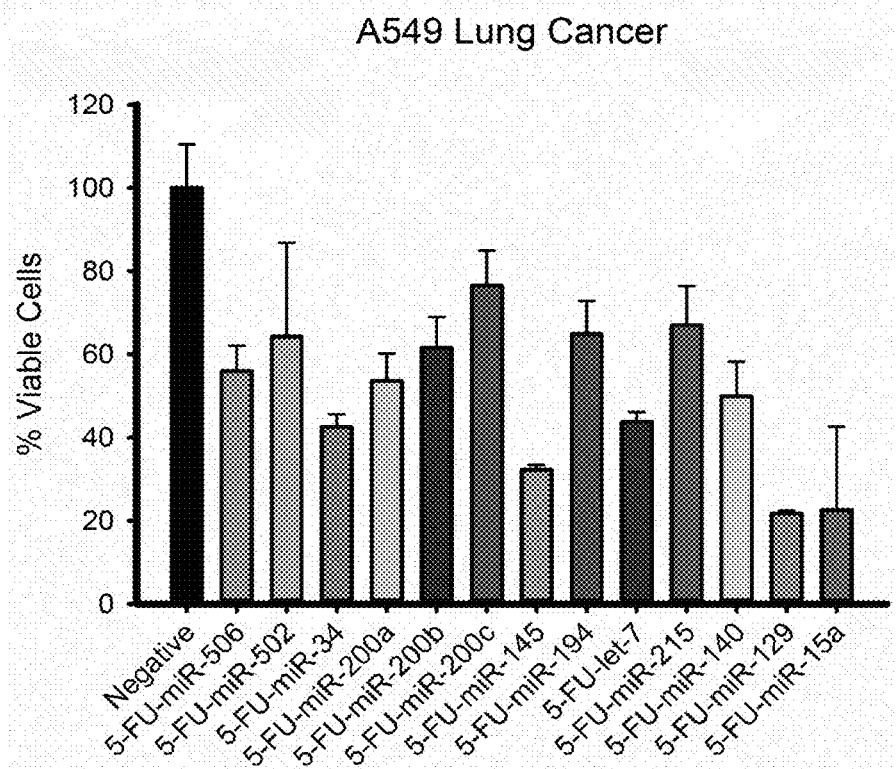

In another example, the modified microRNA nucleic acid compositions of the present disclosure are used to treat lung cancer. For example, as shown in FIG. 14D each of modified miR-129, miR-15a, miR-192, miR-215, miR-140, miR-502, miR-506, miR-34, miR-200a, miR-200b, miR-200c, miR-145, miR-194, and miR-let-7 can be used to treat lung cancer. Therefore, the present methods include the treatment of non-small cell lung cancers, such as squamous cell carcinoma, adenocarcinoma, and large cell carcinoma. Lung cancer often arises from malignancies in the bronchi of the lungs and spreads to other parts of the body, such as lymph nodes. For example, in the case of small cell lung cancer, a cancerous lesion is often found in once lung then spreads to the second lung, the fluid surrounding the lungs (pleura) or neighboring organs. Lung cancer is staged based on size of the primary tumor and whether it has grown outside of the lung into lymph nodes and whether it has metastasized to other organs of the body (e.g., bones, liver, breast, brain). This information is then combined and used to provide the specific stage, i.e., 0, 1, 2, 3 and 4. For stage zero (0), i.e., carcinoma in situ, the cancer is small in size and has not spread into deeper lung tissues or outside the lungs. Stage 1 lung cancer shows cancerous cells present in the underlying lung tissues, but the lymph nodes remain unaffected. Stage 2 lung cancer reveals that the cancer has spread to nearby lymph nodes or into the chest wall. Stage 3 lung cancer is classified by a continuous spread from the lungs to the lymph nodes or to nearby structures and organs, such as the heart, trachea and esophagus. Stage 4 lung cancer exhibits metastasized cancer throughout the body, which may affect the liver, bones or brain.

Figure 16A:
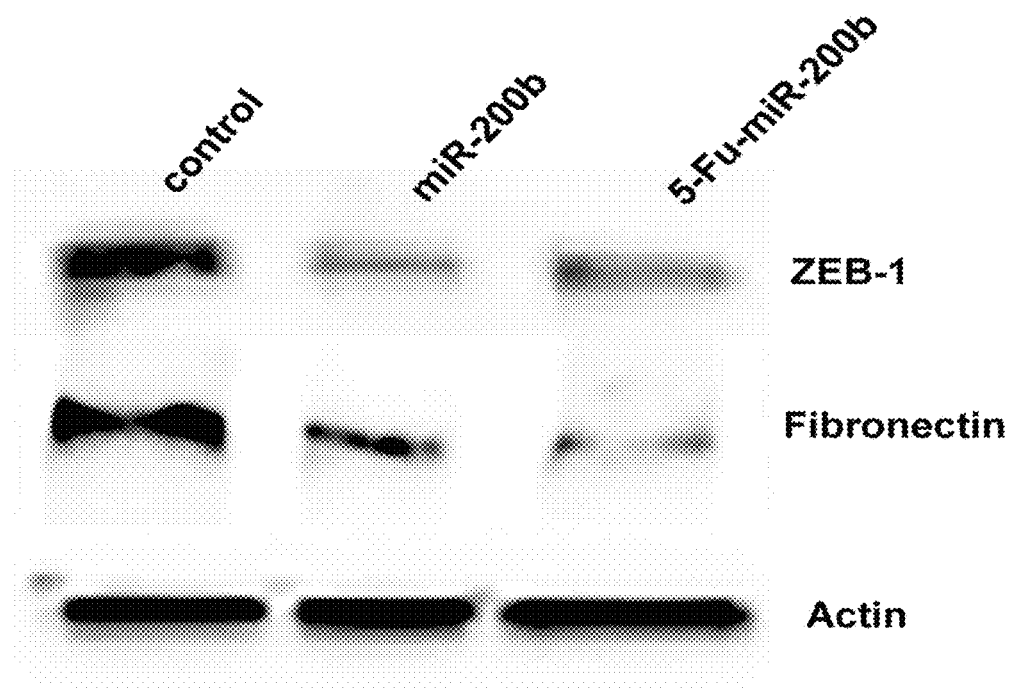
Figure 16B:
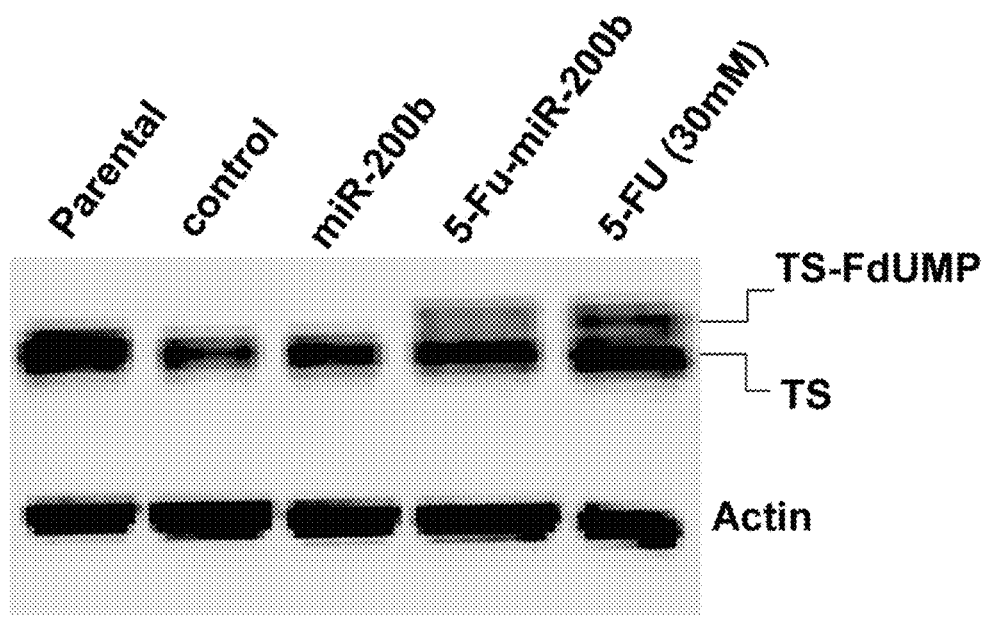

In yet another example, the microRNA mimics of the present disclosure are used to treat breast cancer. As shown in FIGS. 14C and 16C, each of modified miR-129, miR-15a, miR-192, miR-215, miR-140, miR-502, miR-506, miR-34, miR-200a, miR-200b, miR-200c, miR-145, miR-194, and miR-let-7 can be used to treat breast cancer. There are several primary forms of breast cancer. For example, ductal carcinoma begins in the cells of the ducts. In contrast, lobular carcinoma, which is often found in both breasts, originates in the lobes or lobules. As such, the present methods include the treatment of both ductal and lobular breast cancers. More specifically, breast cancers may develop from the presence of one or more genetic mutations, such as HER2 or BRACA. As shown in FIGS. 16A-16C, the present methods are useful in the treatment of such breast cancers. Therefore, in a specific embodiment the present methods can be used to treat triple negative breast cancer.

In yet another example, the microRNA mimics of the present disclosure are used to treat gastric cancer. As shown in FIG. 14B, each of modified miR-129, miR-15a, miR-192, miR-215, miR-140, miR-502, miR-506, miR-34, miR-200a, miR-200b, miR-200c, miR-145, miR-194, and miR-let-7 can be used to treat gastric cancer. Gastric cancers typically present in two forms, intestinal adenocarcinomas, which are well differentiated or diffuse adenocarcinomas, which are poorly differentiated and do not form glandular structures. As such, the present methods include the treatment of both stomach cancer and gastric adenocarcinoma.

Figure 14E:
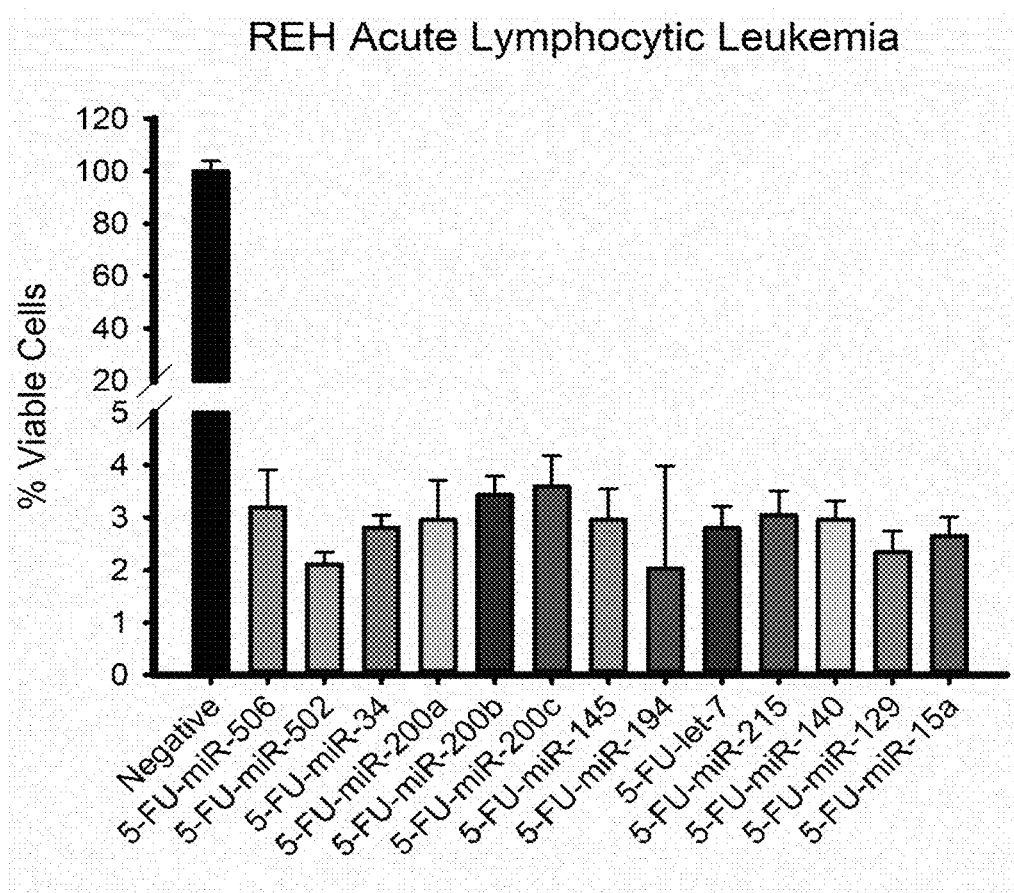
Figure 15C:
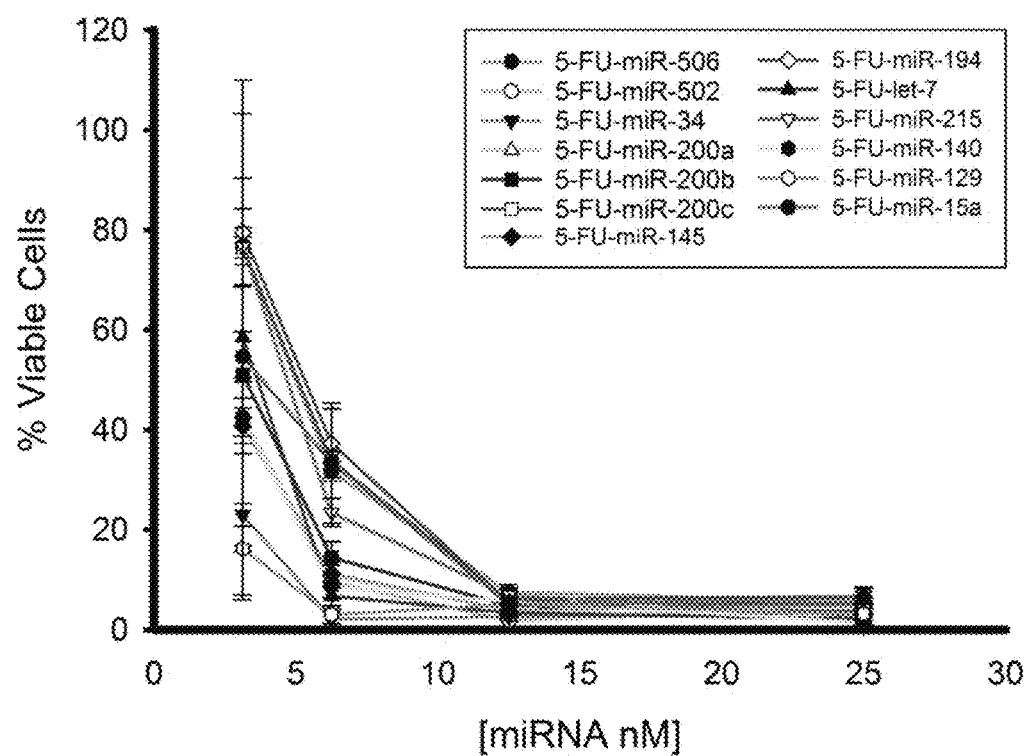

In yet another example, the microRNA mimics of the present disclosure are used to treat blood cancers. As shown in FIGS. 14E and 15C, each of modified miR-129, miR-15a, miR-192, miR-215, miR-140, miR-502, miR-506, miR-34, miR-200a, miR-200b, miR-200c, miR-145, miR-194, and miR-let-7 can be used to treat blood cancer. There are several types of leukemia including, but not limited to, acute lymphoblastic leukemia (ALL), acute mylogenous leukemia (AML), acute lymphocytic leukemia (ACL), chronic lymphocytic leukemia (CLL) and chronic mylogenous leukemia (CML). As shown in FIGS. 14E and 15C the present methods are useful in the treatment of leukemia. As such, the present methods include the treatment of ALL, ACL, AML, CLL and CML. In a specific embodiment, the present methods can be used to treat acute lymphocytic leukemia (ACL).

According to the present disclosure, methods of treating cancer include administration of one or more nucleic acid compositions of the present by any of the routes commonly known in the art. This includes, for example, (1) oral administration; (2) parenteral administration, for example, by subcutaneous, intramuscular or intravenous injection; (3) topical administration; or (4) intravaginal or intrarectal administration; (5) sublingual or buccal administration; (6) ocular administration; (7) transdermal administration; (8) nasal administration; and (9) administration directly to the organ or cells in need thereof.

In specific embodiments, the modified microRNA compositions of the present disclosure are administered to a subject by injection. In one embodiment, a therapeutically effective amount of a modified microRNA composition is injected intravenously. In another embodiment, a therapeutically effective amount of a modified microRNA composition is injected intraperitoneally The amount (dosage) of nucleic acid compositions of the present disclosure being administered depends on several factors, including the type and stage of the cancer, presence or absence of an auxiliary or adjuvant drug, and the subject's weight, age, health, and tolerance for the agent. Depending on these various factors, the dosage may be, for example, about 2 mg/kg of body weight, about 5 mg/kg of body weight, about 10 mg/kg of body weight, about 15 mg/kg of body weight, about 20 mg/kg of body weight, about 25 mg/kg of body weight, about 30 mg/kg of body weight, about 40 mg/kg of body weight, about 50 mg/kg of body weight, about 60 mg/kg of body weight, about 70 mg/kg of body weight, about 80 mg/kg of body weight, about 90 mg/kg of body weight, about 100 mg/kg of body weight, about 125 mg/kg of body weight, about 150 mg/kg of body weight, about 175 mg/kg of body weight, about 200 mg/kg of body weight, about 250 mg/kg of body weight, about 300 mg/kg of body weight, about 350 mg/kg of body weight, about 400 mg/kg of body weight, about 500 mg/kg of body weight, about 600 mg/kg of body weight, about 700 mg/kg of body weight, about 800 mg/kg of body weight, about 900 mg/kg of body weight, or about 1000 mg/kg of body weight, wherein the term "about" is generally understood to be within ±10%, 5%, 2%, or 1% of the indicated value. The dosage may also be within a range bounded by any two of the foregoing values. Routine experimentation may be used to determine the appropriate dosage regimen for each patient by monitoring the compound's effect on the cancerous or pre-cancerous condition, or effect on microRNA expression level or activity (e.g., miR-15a, miR-200a, miR-200b, miR-200c, miR-145, miR-194, miR-34, miR-let-7, miR-129, miR-140, miR-192, miR-502, miR-506), or effect on a target thereof, such as BCL2 level or activity, or effect on TS level or activity, or effect on E2F3 level or the disease pathology, all of which can be frequently and easily monitored according to methods known in the art. Depending on the various factors discussed above, any of the above exemplary doses of nucleic acid can be administered once, twice, or multiple times per day.

The ability of the nucleic acid compositions described herein, and optionally, any additional chemotherapeutic agent for use with the current methods can be determined using pharmacological models well known in the art, such as cytotoxic assays, apoptosis staining assays, xenograft assays, and binding assays.

The nucleic acid compositions described herein may or may not also be co-administered with one or more chemotherapeutic agents, which may be auxiliary or adjuvant drugs different from a nucleic composition described herein.

As used herein, "chemotherapy" or the phrase a "chemotherapeutic agent" is an agent useful in the treatment of cancer. Chemotherapeutic agents useful in conjunction with the methods described herein include, for example, any agent that modulates BCL2, E2F3 or TS, either directly or indirectly. Examples of chemotherapeutic agents include:

anti-metabolites such as methotrexate and fluoropyrimidine-based pyrimidine antagonist, 5-fluorouracil (5-FU) (Carac® cream, Efudex®, Fluoroplex®, Adrucil®) and S-1; antifolates, including polyglutamatable antifolate compounds; raltitrexed (Tomudex®), GW1843 and pemetrexed (Alimta®) and non-polyglutamatable antifolate compounds; nolatrexed (Thymitaq®), plevitrexed, BGC945; folic acid analogs such as denopterin, methotrexate, pteropterin, trimetrexate; and purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine. In a specific embodiment of the current disclosure, the chemotherapeutic agent is a compound capable of inhibiting the expression or activity of genes, or gene products involved in signaling pathways implicated in aberrant cell proliferation or apoptosis, such as, for example, YAP1, BMI1, DCLK1, BCL2, thymidylate synthase or E2F3; and pharmaceutically acceptable salts, acids or derivatives of any of the above.

In other embodiments, the chemotherapy can be any of the following cancer drugs, such as one or more of methotrexate, doxorubicin, cyclophosphamide, cis-platin, oxaliplatin, bleomycine, vinblastine, gemcitabine, vincristine, epirubicin, folinic acid, paclitaxel, and docetaxel. The chemotherapeutic agent may be administered before, during, or after commencing therapy with the nucleic acid composition.

In some embodiments, the chemotherapeutic agent is an anti-cancer drug, or a tissue sensitizer or other promoter for an anti-cancer drug. In some embodiments, the co-drug may be another nucleic acid, or another miRNA, such as a microRNA mimic of the present disclosure, gemctiabine or free 5-FU.

In a specific embodiment, the other nucleic acid is a short hairpin RNA (shRNA), siRNA, or nucleic acid complementary to a portion of the BCL2 3'UTR.

In some embodiments, the chemotherapeutic agent is a co-drug.

E2F transcription factor 3, E2F3 (RefSeq NG_029591.1, NM_001243076.2, NP_001230005.1) is a transcription factor that binds DNA and interacts with effector proteins, including but not limited to, retinoblastoma protein to regulate the expression of genes involved in cell cycle regulation. Therefore, any drug that inhibits the expression of E2F3 may be considered herein as a co-drug.

B-cell lymphoma 2 (BCL2), (RefSeq NG_009361.1, NM_000633, NP_000624) including isoform a (NM_000633.2, NP_000624.2) and β NM_000657.2, NP_000648.2 thereof, are encoded by the Bcl-2 gene, which is a member of the BCL2 family of regulator proteins that regulate mitochondria regulated cell death via the intrinsic apoptosis pathway. BCL2 is an integral outer mitochondrial membrane protein that blocks the apoptotic death of cell cells by binding BAD and BAK proteins. Non-limiting examples of BCL2 inhibitors include antisense oligonucleotides, such as Oblimersen (Genasense; Genta Inc.,), BH3 mimetic small molecule inhibitors including, ABT-737 (Abbott Laboratories, Inc.), ABT-199 (Abbott Laboratories, Inc.), and Obatoclax (Cephalon Inc.). Any drug that inhibits the expression of BCL2 may be considered herein as a co-drug.

Thymidylate synthase (RefSeq: NG_028255.1, NM_001071.2, NP_001062.1) is a ubiquitous enzyme, which catalyses the essential methylation of dUMP to generate dTMP, one of the four bases which make up DNA. The reaction requires CH H$_4$-folate as a cofactor, both as a methyl group donor, and uniquely, as a reductant. The constant requirement for CH H$_4$-folate means that thymidylate synthase activity is strongly linked to the activity of the two enzymes responsible for replenishing the cellular folate pool: dihydrofolate reductase and serine transhydroxymethylase. Thymidylate synthase is a homodimer of 30-35 kDa subunits. The active site binds both the folate cofactor and the dUMP substrate simultaneously, with the dUMP covalently bonded to the enzyme via a nucleophilic cysteine residue (See, Carreras et al, Annu. Rev. Biochem., (1995) 64:721-762). The thymidylate synthase reaction is a crucial part of the pyrimidine biosynthesis pathway which generates dCTP and dTTP for incorporation into DNA. This reaction is required for DNA replication and cell growth. Thymidylate synthase activity is therefore required by all rapidly dividing cells such as cancer cells. Due to its association with DNA synthesis, and therefore, cellular replication, thymidylate synthase has been the target for anti-cancer drugs for many years. Non-limiting examples of thymidylate synthase inhibitors include folate and dUMP analogs, such as 5-fluorouracil (5-FU). Any drug that inhibits the expression of thymidylate synthase may be considered herein as a co-drug.

If desired, the administration of the nucleic acid composition described herein may be combined with one or more non-drug therapies, such as, for example, radiotherapy, and/or surgery. As well known in the art, radiation therapy and/or administration of the chemotherapeutic agent (in this case, the nucleic acid composition described herein, and optionally, any additional chemotherapeutic agent) may be given before surgery to, for example, shrink a tumor or stop the spread of the cancer before the surgery. As also well known in the art, radiation therapy and/or administration of the chemotherapeutic agent may be given after surgery to destroy any remaining cancer.

Examples have been set forth below for the purpose of illustration and to describe certain specific embodiments of the invention. However, the scope of this invention is not to be in any way limited by the examples set forth herein.

EXAMPLES

Example 1. Materials and Methods

Modified microRNAs:

the 5-FU modified miRs were synthesized by an automated oligonucleotide synthesis process and purified by HPLC. The two strands were annealed to make the mature modified 5-FU-miRs of the present disclosure. More specifically, a process referred to as "2'-ACE RNA synthesis" was used. The 2'-ACE RNA synthesis is based on a protecting group scheme in which a silylether is employed to protect the 5'-hydroxyl group in combination with an acid-labile orthoester protecting group on the 2'-hydroxy (2'-ACE). This combination of protecting groups is then used with standard phosphoramidite solid-phase synthesis technology. See, for example, S. A. Scaringe, F. E. Wincott, and M. H. Caruthers, *J. Am. Chem. Soc.,* 120 (45), 11820-11821 (1998); International PCT Application WO/1996/041809; M. D. Matteucci, M. H. Caruthers, *J. Am. Chem. Soc.,* 103, 3185-3191 (1981); S. L. Beaucage, M. H. Caruthers, *Tetrahedron Lett.* 22, 1859-1862 (1981), the entire contents of each of which are expressly incorporated herein.

The exemplary modified miR-15a nucleic acid, modified miR-140 nucleic acid, modified miR-192 nucleic acid, modified miR-502, modified miR-506 nucleic acid modified miR-34 nucleic acid, modified miR-194 nucleic acid, modified miR-200a, modified miR-200b, modified miR-200c nucleic acid, modified miR-145 nucleic acid, modified miR-let-7 nucleic acid or any other modified microRNAs that replace uracil with a 5-halouracil can be synthesized in the same manner as set forth herein.

Some exemplary structures of the protected and functionalized ribonucleoside phosphoramidites currently in use are shown below:

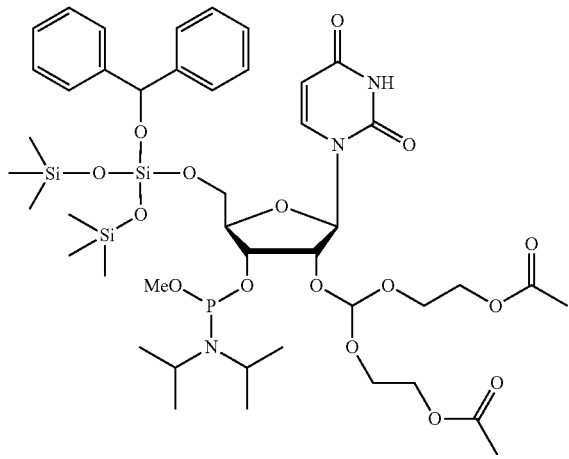

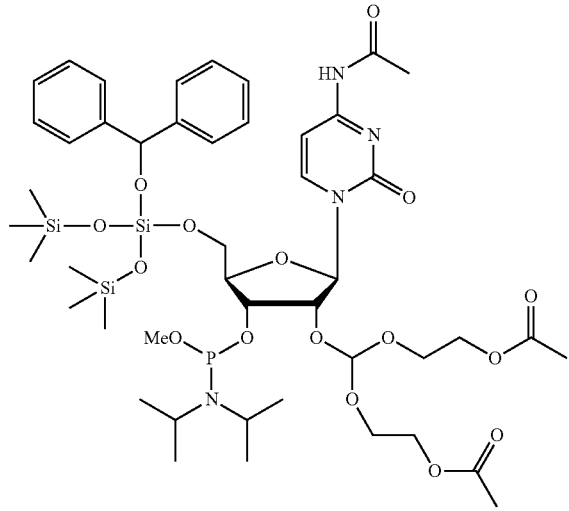

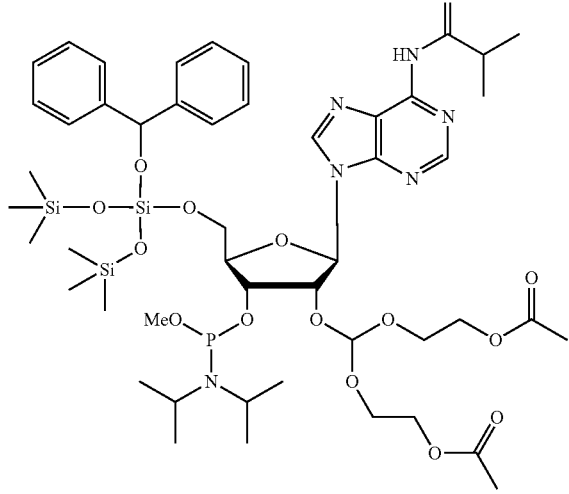

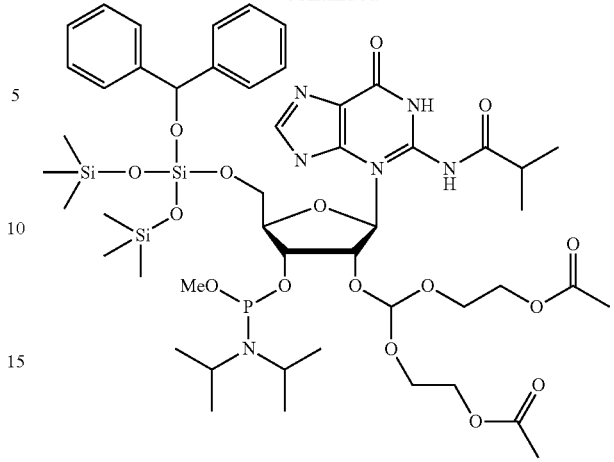

-continued

Cell Culture.

The human colon cancer cell lines HCT116, RKO, SW480, SW620, and the normal colon cell line CCD 841 CoN, pancreatic cancer cell lines ASPC-1, HS766T, Panc-1, AGS gastric cancer cell line, SKBR3 and MDA-MB-231 breast cancer cells, REH acute lymphocytic cell lines, and lung cancer cell line A549, were obtained from the American Type Culture Collection (ATCC) and maintained in various types of media. For example, McCoy's 5A medium (SKBR3, HCT-116), DMEM (RKO, HS766T, SW480, SW620) and MEM (CCD 841 CoN), RPMI-1640 (REH and APSC-1) and F-12K media (AGS, A549). Media was supplemented with 10% fetal bovine serum (Thermo Fischer).

For transfections, $1\times10^5$ cells were plated in six-well plates and transfected with 100 nM of control non-specific miRNA (Thermo Fischer), a modified microRNA, or exogenous native microRNA after 24 hours using Oligofectamine (Thermo Fischer) following the manufacturer's protocols. For reagent free transfection, cells were plated in 6 well plates at $(1\times10^5)$ cells per well. Twenty-four hours later 100 pmol miRNA (Control, miR-15a, Mimic-1) were diluted in Optimem (Thermo Fischer) and added to the plate. Media was changed after 24 hours. Media was supplemented with 10% fetal bovine serum (Thermo Fischer). Briefly, cells were cultured in growth media (DMEM/F12 supplemented with B27, 10 ng/mL bFGF, and 20 ng/mL EGF (Life Technologies) in ultra-low attachment flasks) for up to 6 days. The spheroid cells were maintained by collection through gentle centrifugation, dissociation to single cells and replating.

Western Immunoblot Analysis:

Forty-eight hours after transfection, equal amounts of protein (15 μg) extracted from cells lysed in RIPA buffer with protease inhibitor (Sigma) and were separated on 10%-12% sodium dodecyl sulfate-polyacrylamide gels using standard procedures. The primary antibodies used for the analysis were rabbit anti-YAP1 monoclonal antibody (1:10000) (Cell Signaling Technologies), anti-DLCK1 (1:500) (Abcam), anti-BCL2 (1:500) (NeoMarkers), ant-BMI-1 (1:10000) (Cell Signaling Technologies), mouse anti-human TS antibody (1:500), anti-a-tubulin (1:50000) (Santa Cruz Biotech Inc.), anti-GAPDH (1:100000) (Santa Cruz Biotech Inc.), ant-E2F3 (1:500) (Santa Cruz Biotech Inc.). Horseradish peroxidase-conjugated antibodies against mouse or rabbit (1:5000, Santa Cruz Biotech Inc.) were used as the secondary antibodies. Protein bands were visualized with autoradiography film using SuperSignal West Pico Chemiluminescent Substrate (Thermo Fischer). Western blot density was quantified using Image J software.

Cell Proliferation Assay:

Twenty-four hours after transfection, cells were seeded in 96-well plates at a density of 2000 cells per well. The cell proliferation assay was performed on days 1 to 5 by incubating 10 µl WST-1 (Roche Applied Science, Mannheim, Germany) in the culture medium for 1 h and reading the absorbance at 450 and 630 nm. The cell proliferation rate was calculated by subtracting the absorbance at 450 nm from the absorbance at 630 nm. Experiments for the cell proliferation assay were performed at least three times. The O.D. was calculated by subtracting the absorbance at 630 nm from that at 450 nm. Proliferation experiments were performed three times.

Anchorage-independent proliferation was studied to determine cancer cell colony forming ability. Cancer cells were trypsinized and counted and a total of $1 \times 10^5$ cells per well were transfected in 6-well plates with 25 nM modified microRNA or native miRs or a negative control miRNA with oligofectamine, and 6 hours after transfection, cells were recounted. A total of 20,000 cells in 0.35% agar (Bacto Agar; Becton Dickinson) were layered on top of 1 mL of a solidified 0.6% agar layer in a 35-mm dish. Growth media with B27, 10 ng/mL bFGF, and 20 ng/mL EGF were included in both layers. After 2 weeks of incubation, colonies more than 50 mm in diameter were counted.

Cell Cycle Analysis:

Twenty-four hours after transfection, cells were harvested and resuspended at 0.5 to $1 \times 10^6$ cells/mL in modified Krishan's buffer supplemented with 0.02 mg/mL RNase H and 0.05 mg/mL propidium iodide. Stained cells were detected by flow cytometry and results were analyzed with Modfit LT™ software. The experiments for cell cycle analysis were performed at least three times.

Apoptosis Assay.

To distinguish between early and late apoptosis, a fluorescein isothiocyanate (FITC)-Annexin assay was done (Becton Dickinson). HCT116, RKO, SW480 and SW620 cells were plated into 6 well plates ($1 \times 10^5$) cells per well, after 24h, cells were transfected with 25 nM modified miRNAs using Oligofectamine. Forty-eight hours after transfection, cells were harvested, stained with propidium iodide and anti-annexin-V antibody (Annexin V-FITC Apoptosis Detection kit, Invitrogen, CA, USA) following the manufacturer's protocol, and stained cells were detected by flow cytometry.

5-FU Treatment and Cytotoxicity Assay:

Twenty-four hours after transfection, cancer cells were plated in 96-well plates at $2 \times 10^3$ cells per well in triplicates in 100 µL of medium. After 24 hours, fresh medium containing 2 µM 5-FU alone, 50 nM native microRNA, 50 nM modified microRNA (e.g., modified miR-129), or a combination of 2 mM 5-FU with 50 nM a modified microRNA of the present disclosure e.g., modified miR-129, were added, and cells were cultured for an additional 72 hours. Cell viability was measured using the WST-1 assay.

Lentivirus Production:

Briefly, $1.5 \times 10^6$ 293T cells were plated in a 10-cm dish with 10 mL of DMEM+10% FBS. Two days later, pEZX-MR03, a lentiviral plasmid, expressing miR-129 or hsa-miR-15a, was transfected with Lenti-Pac HIV expression packaging kit following the manufacturer's protocol. Forty-eight hours later, the virus was harvested and concentrated with Lenti-Pac lentivirus concentration solution. Then the titer of the virus (approximately 1011 virus particles/ml) was determined with Lenti-Pac™ HIV qRT-PCR titration kit. In addition, serial dilution of the virus (0.1 µL, 0.5 µL, 2 µL, 10 µL, 50 µL) was used to transduce $5 \times 10^4$ HCT116 CSC to determine the transduction efficiency. The lowest concentration (2 µL) to achieve 100% positive expression was used to infect the cells for mouse in vivo treatment experiments.

Real-Time qRT-PCR Analysis of Nucleic Acid Expression.

The expression levels of microRNAs in cancer cells were quantified. Briefly, the primers specific to the microRNA of interest and an internal control RNU44 gene were purchased from Ambion. cDNA synthesis was performed by the High Capacity cDNA Synthesis Kit (Applied Biosystems) with miRNA-specific primers. Real-time qRT-PCR was carried out on an Applied Biosystems 7500 Real-Time PCR machine with miRNA-specific primers by TaqMan Gene Expression Assay (Applied Biosystems). Expression level of the exemplary miRs of the present disclosure was calculated by the $\Delta\Delta CT$ method based on the internal control RNU44, normalized to the control group and plotted as relative quantification.

Human Cancer Stem Cell Profiler:

RNAs were extracted from cancer cells transfected with either exemplary microRNAs of the present disclosure or negative miRNA using TRIzol reagent (Thermo Fischer) in accordance with the manufacturer's protocol. RNAs were transcribed to first-strand cDNA using the RT2 First Strand Kit (Qiagen). Next, the cDNA is mixed with RT2 SYBR Green Mastermix (Qiagen), and this mixture is aliquoted into the wells of the Human Cancer Stem Cells RT2 Profiler PCR Array (Qiagen). Applied Biosystems 7500 Real-Time PCR machine was used for qRT-PCR (Applied Biosystems), and relative expression values were determined using the $\Delta\Delta CT$ method.

Mouse Subcutaneous Tumor Implantation Model:

Two days before injection, HCT116 cancer stem cells were plated at $5 \times 10^5$/well in a 6-well ultra low attachment plate. 20 µL of the virus or 100 pmole exemplary modified miR-129 or modified miR-15a were used to transduce or transfect cells. Forty-eight hours later, cells were collected and resuspended at $10^6$/ml in DMEM/F12 knockout media with 30% matrigel. Ten-twelve week-old NOD/SCID mice (Jackson Laboratories. Bar Harbor, Mass., USA) were used for tumor implantation. The mice were anesthetized by isoflurane inhalation. 100 µL of cell suspension was injected subcutaneously into both sides of the lower back area. The tumor size was measured using a caliper, and tumor volume was calculated using the formula $V = length \times width^2 / 2$.

For in vivo miRNA delivery experiments, colon cancer cells were created that expressed the lenti-luc reporter gene by infecting parental HCT116 cells with a recombinant lentivirus. Luciferase-expressing HCT116 cells ($2.0 \times 10^6$ cells per mouse) were suspended in 0.1 mL of PBS solution and was injected through tail vein of each mouse. Two weeks after injection of colon cancer cells, mice were treated via tail vein injection with 40 µg of negative control or modified miR(s) packaged with in vivo-jetPEI (Polyplus Transfection). Mice were treated every other day for 2 weeks (8 times). Following treatment, mice were screened using IVIS Spectrum In vivo Imaging System (IVIS) (PerkinElmer).

RNA Isolation:

For mouse xenografts, sectioned tissues were deparaffinized, hydrated, and digested with proteinase K, respectively. Subsequently, total RNA was isolated using the TRIzol® reagent. Total RNA was also isolated from clinical specimens by the TRIzol®-based approach.

Statistical Analysis

All experiments were repeated at least three times. All statistical analyses were performed with SigmaPlot software. The statistical significance between two groups was determined using Student's t-test (paired t-test for clinical samples, and unpaired t-test for all other samples). For comparison of more than two groups, one-way ANOVA followed by a Bonferroni-Dunn test was used. Data were expressed as mean±standard error of the mean (SEM). The statistical significance is either described in figure legends, or indicated with asterisks (*). *=P<0.05; =P<0.01; *=P<0.001.

Figure 17A:
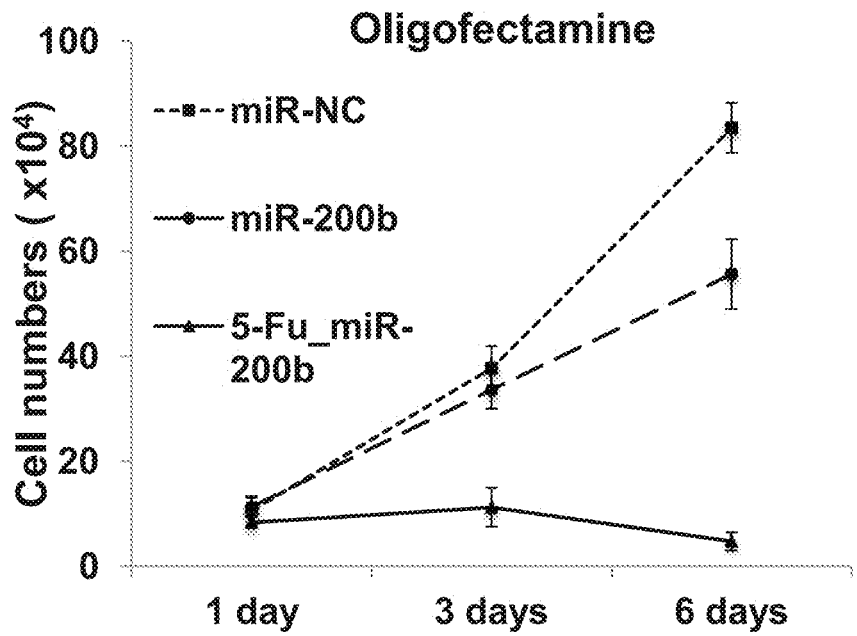
FIGS. 17A-17B. Modified microRNA molecules can be delivered to cancer cells without exogenous delivery vehicles. (A) MDA-MB-231 cells were transfected with non-specific microRNA control nucleic acids (miR-NC), native miR-200b, or modified miR-200b (5-FU-miR-200b) in the presence of oligofectamine or (B) contacted by NC (negative control), native miR-200b, or modified miR-200b (5-FU-miR-200b) without delivery vehicle (i.e., no oligofectamine). Modified miR-200b effectively reduced cell proliferation of breast cancer cells with or without delivery vehicle when compared to negative controls and native miR-200b. In contrast, exogenous miR-200b did not inhibit cell growth in the absence of a delivery vehicle.
Figure 17B:
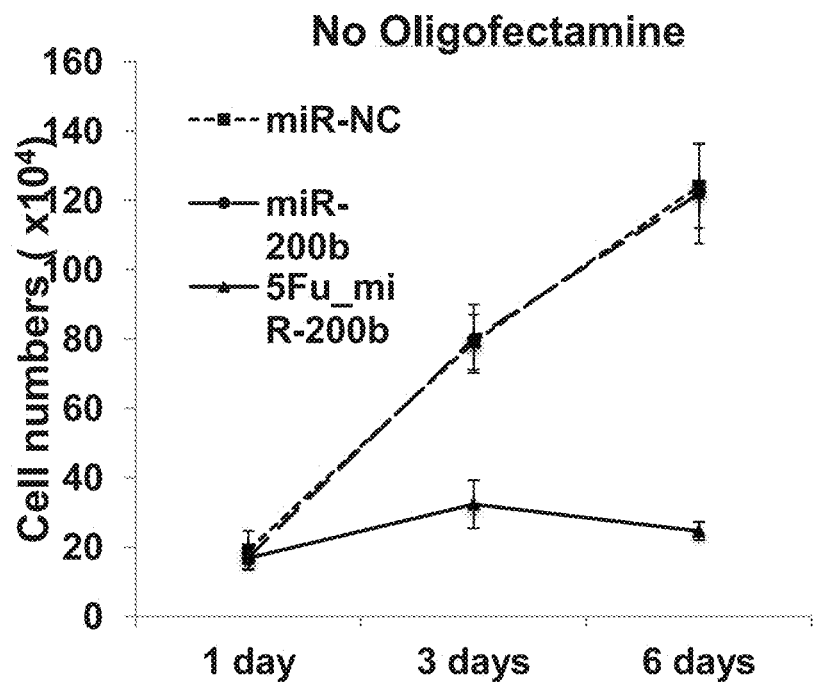

Example 2: Modified microRNAs of the Present Disclosure have Anti-Cancer Activity As shown in FIGS. 3, 8B, 12A-D 13A-B, 14A-E and 15A-C, the modified miRNAs (modified miR: 129, 15a, 192 (215), 140, 502, 34, 194, 200a, 200b, 200c, 145, let-7 and 506) are effective in inhibiting colon cancer, blood cancer, breast cancer, gastric cancer, pancreatic cancer, and lung cancer cell proliferation when compared to one or controls (i.e, non-specific microRNA, non-modified miRNA precursor, or vehicle alone). In addition, the modified miRNAs can be delivered into cancer cells without the transfection reagent (as shown in FIGS. 17A-17B). Notably, the results show that cancer cell proliferation across several different colorectal cancer cell lines, pancreatic cancer cell lines, breast cancer cell lines, lung cancer cell lines, a gastric cancer cell line and a leukemia cell line is inhibited significantly when compared to cancer cells treated with control microRNAs or vehicle alone.

Example 3: Modified miR-129 Nucleic Acids have Anti-Cancer Activity

In the following experiments, 5-FU was incorporated into miR-129. In one experiment, all U bases in miR-129 were replaced with 5-FU, as shown in the structure provided in FIG. 1A, where "$U^F$" represents 5-fluorouracil or other 5-halouracil. In another experiment, all U bases, except the seed region of the miR-129, were replaced with 5-FU, as shown in the structure provided in FIG. 1B.

Figure 2B:
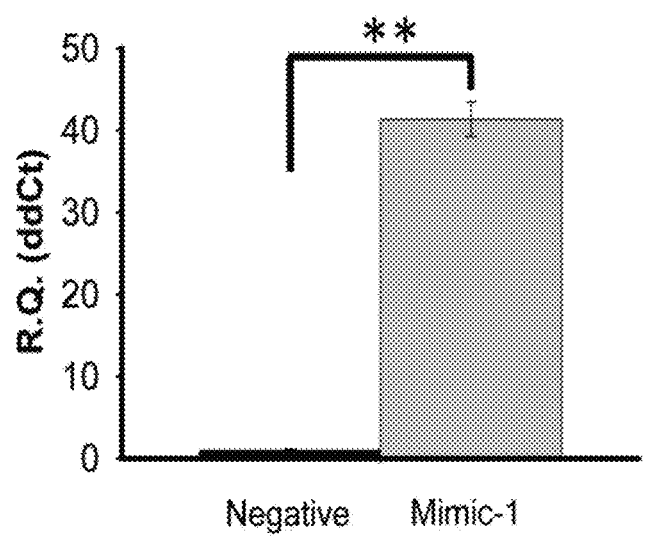
Figure 2C:
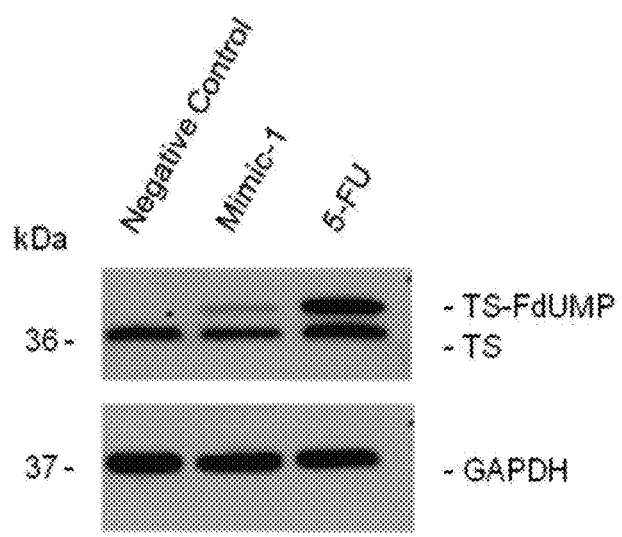

Analysis of Target Specificity:

The results of Western immunoblot experiments in colon cancer HCT-116 cells demonstrate that the exemplary modified miR-129 polynucleotides of the present disclosure were able to retain their target specificity to TS, BCL2 and E2F3 via. The results are shown in FIGS. 2A and 2B, which shows the results for the modified miR-129 nucleic acid having all U bases were replaced with 5-FU, as obtained by two separate operators as set forth in SEQ ID. NO: 4. Of further significance, the exemplary miR-129 mimics were found to be more potent than unmodified (control) miR-129 in reducing the expression levels of TS, BCL2 and E2F3.

Function Enhancement of Modified microRNAs of the Present Disclosure.

The impact of an exemplary modified miR-129 on colon cancer cell proliferation was compared to that of native miR-129. The results show that, at 50 nM concentration, 5-FU-miR-129 can suppress HCT-116 tumor cell growth completely. Moreover, as shown by the results in FIG. 3, 5-FU-miR-129 is much more potent than the native miR-129, thereby providing a significantly higher inhibitory effect. Such inhibition is specific, as the scramble control miR has no effect on cell proliferation.

Figure 4:
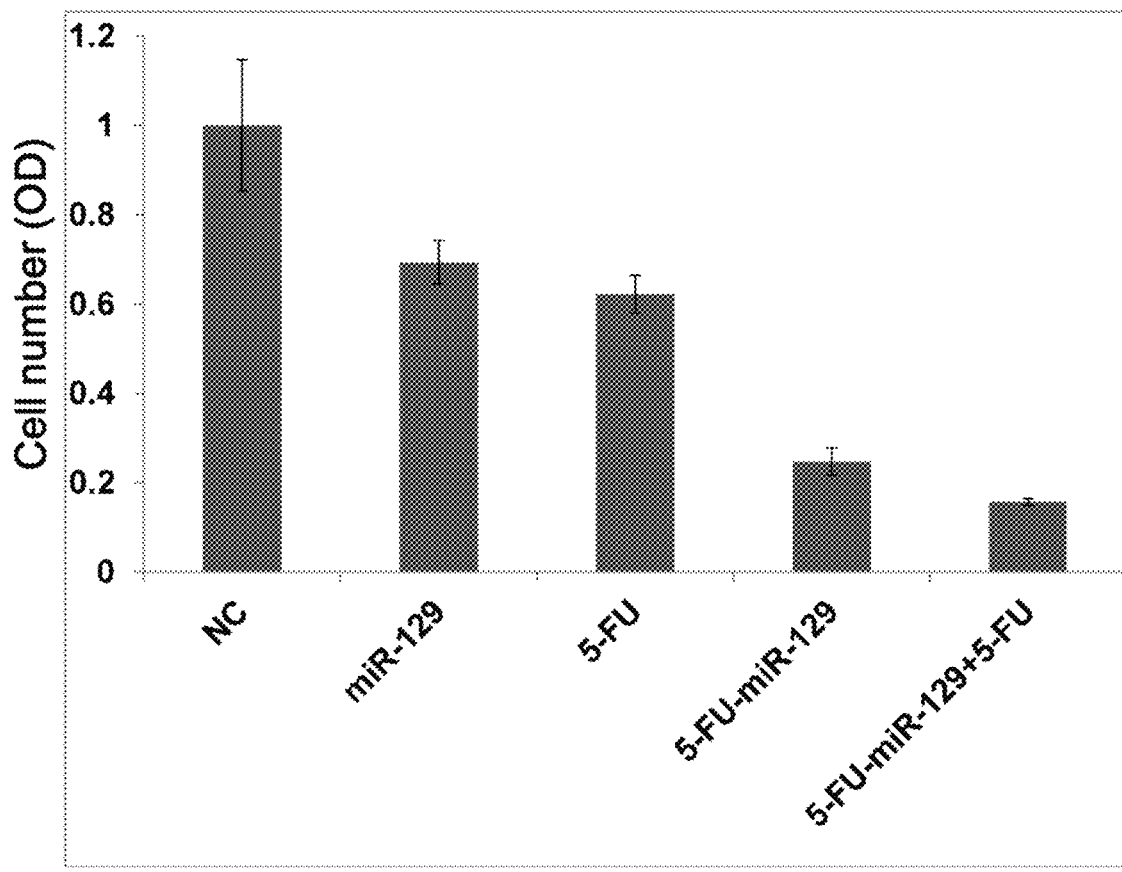
FIG. 4. Combination therapy with 5-FU and modified microRNA compositions of the present disclosure effectively inhibit cancer cell proliferation. Graphical comparison of colon cancer cell proliferation for cancer cells treated with a negative control (NC), exogenously expressed native miR-129 (miR-129), 5-FU, an exemplary modified miR-129 nucleic acid of the present disclosure (5-FU-miR-129), and a combination of 5-FU and the exemplary miR-129 nucleic acid of the present disclosure (5-FU-miR-129+5-FU).

Next, the potencies of modified miR-129 and 5-FU on cell proliferation were compared using HCT-116 colon cancer cells. As shown by the results provided in FIG. 4, 50 nM (40-fold less than 5-FU) of modified miR-129 is unexpectedly much more potent than 2 µM 5-FU in inhibiting tumor cell proliferation.

Exemplary Modified microRNAs of the Present Disclosure Induce Apoptosis in Colon Cancer Cells.

Figure 5A:
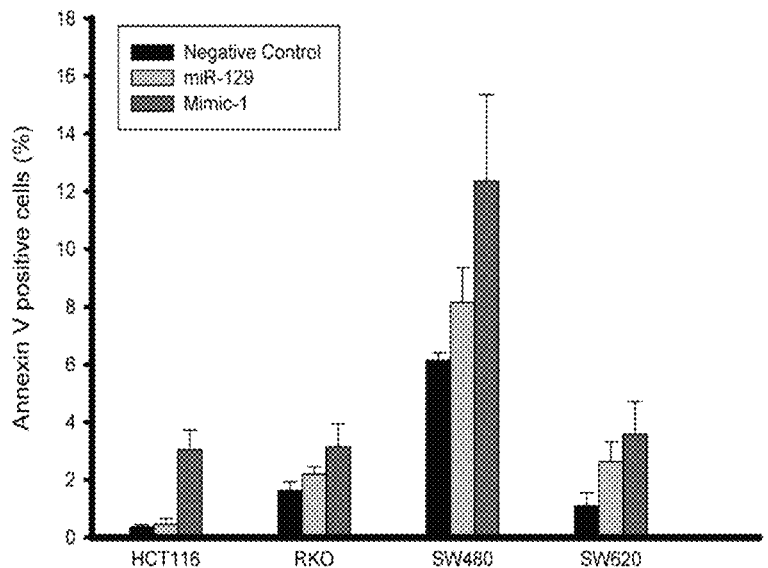
FIGS. 5A-5B. Exemplary modified microRNAs induce apoptosis in colon cancer cells and cause cell cycle arrest. (A) Cell death was quantified by FITC-Annexin V apoptosis assay to show that modified miR-129 nucleic acid compositions of the present disclosure induce cancer cell apoptosis at significantly higher levels than negative controls, or ectopically expressed native miR-129 in several different colorectal cancer cell lines. (B) Flow cytometry was conducted to reveal that modified miR-129 nucleic acid compositions (Mimic-1) of the present disclosure increase G1 cell cycle arrest at significantly higher levels than negative controls, or ectopically expressed native miR-129.

With BCL2 being an important target of miR-129, the impact of a modified miR of the present disclosure on apoptosis was investigated. Specifically, cell death was quantified using an apoptosis assay in HCT116, RKO, SW480, and SW620 colon cancer cells transfected with negative control miRNA, native miR-129 or an exemplary miR-129 mimic of SEQ ID NO: 4. Results show that the miR-129 mimic was able to induce apoptosis by 2 to 30-fold in all 4 colon cancer cell lines via a fluorescence-activated cell sorting (FACS)-based FITC-Annexin assay compared to the native miR-129 and negative control miRNA (FIG. 5A).

miR-129 Mimic Trigger G1/S Cell Cycle Checkpoint Control.

Figure 5B:
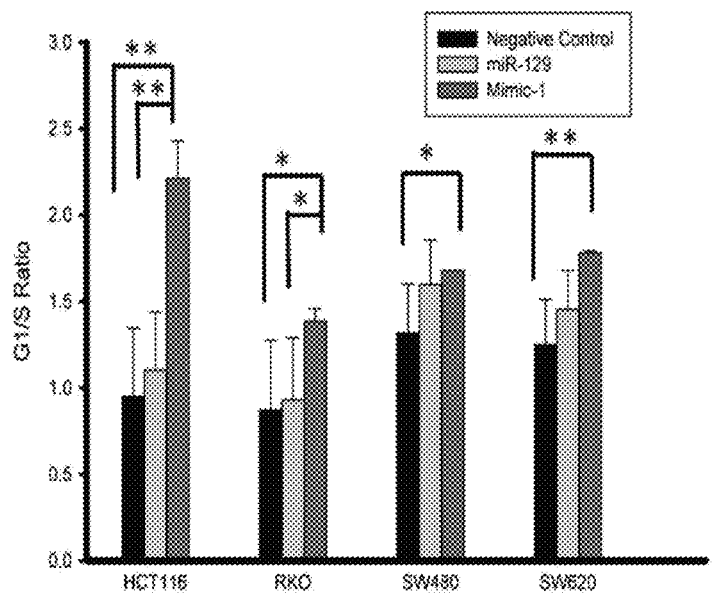

Cell cycle analysis was performed using flow cytometry in HCT-116 cells treated with scramble control, miR-129 precursor, and an exemplary miR-129 mimic. As shown in FIG. 5B, cell cycle analysis revealed that the miR-129 mimic impacts colon cancer cell growth by inducing G1 arrest, and such impact is much more potent (more than two-fold) than native miR-129.

miR-129 Mimics Eliminated Chemotherapy Resistant Colon Cancer Stem Cells.

To determine the impact of certain exemplary modified microRNAs of the present disclosure (i.e., miR-129 mimics) on 5-FU resistant colon cancer stem cells, HCT116 derived colon cancer stem cells were treated with various concentrations of Mimic-1 or 5-FU. The data shown in FIG. 6 reveal that exemplary microRNA mimics of the present disclosure are able to eliminate 5-FU resistant colon cancer stem cells by over 80% at 100 nM concentration, while a lethal dose of 5-FU at 100 µM has minimal effect on tumor stem cell viability.

Figure 6:
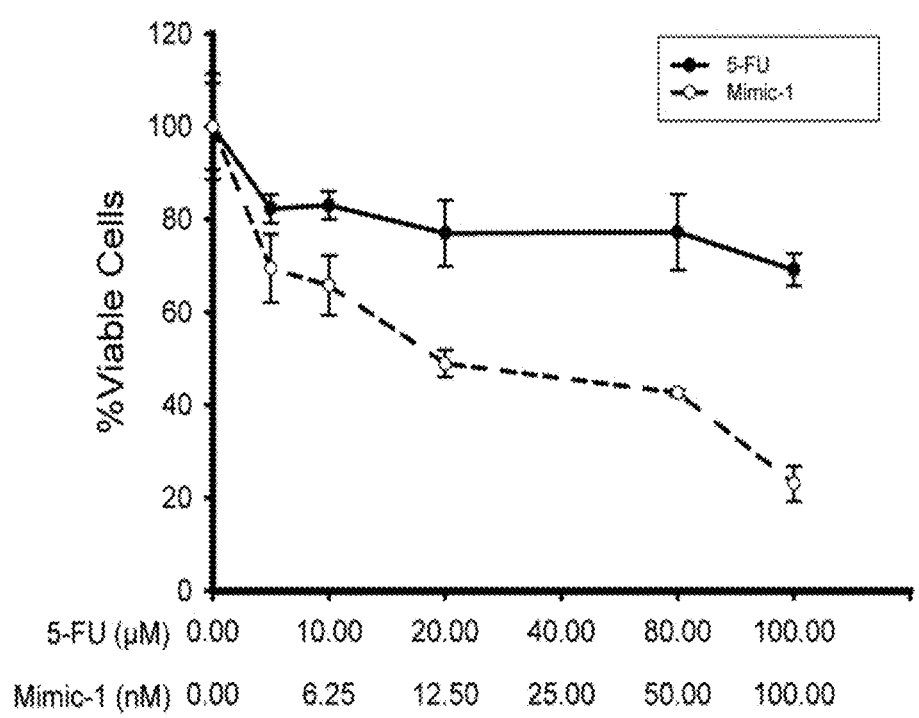
FIG. 6. Modified microRNA nucleic acid compositions of the present disclosure eliminate chemotherapy resistant cancer stem cells. HCT116 derived colon cancer stem cells were treated with increasing concentrations of exemplary modified miR-129 nucleic acids of the present disclosure (○) or 5-FU (●). Results show that modified miR-129 nucleic acids killed 5-FU resistance cancer stem cells in a dose dependent manner.

Taken together, these results show that exemplary modified microRNA polynucleotides of the present disclosure were able to inhibit cell proliferation of HCT116 colon cancer stem cells (FIG. 6). Such inhibitory effect by modified miR-129 was much more potent than native miR-129, as proliferation was nearly completely blocked with 25 nM miR-129 on day 6 (FIG. 6). We also demonstrated the impact of treatment of cells with modified miR-129 on anchorage independent cell growth using a soft agar assay. The modified miR-129 treated colon cancer stem cells and formed no visible spheres compared to cells treated with the native miR-129 or control miRNA (similar to those seen in FIG. 10).

miR-129 Mimics Inhibit Colon Cancer Metastasis In Vivo.

The therapeutic impact of modifiying miR-129 nucleic acids was evaluated using a colon cancer metastasis model. Two weeks after establishing metastasis, 40 µg of a miR-129 nucleic acid of SEQ ID NO; 4 was delivered by intravenous injection with treatment frequency of one injection every other day for two weeks.

The results shown in FIG. 7 reveal that modified microRNA-129 inhibits colon cancer metastasis while negative control miRNA has no effect, while exhibiting no toxic side effects.

Example 4. Exemplary Modified miRs and the Anti-Cancer Activity Thereof

Exemplary Modified miR-15a Compositions have Anti-Cancer Activity.

As shown in FIG. 1C and FIG. 1D, exemplary modified miR-15a mimics in which all of the uracil bases (FIG. 1C) or only uracil bases that in the non-seed region (FIG. 1D) of the miR-15a nucleic acid sequence were replaced with a 5-halouracil (i.e., 5-flurouracil) were synthesized as set forth above.

Three days following transfection of the exemplary modified miR-15a set forth in FIG. 1C into HCT-116 colon cancer stem cells, protein was collected and Western Blotting was performed to confirm that the modified miR-15a nucleic acid compositions of the present disclosure maintained the ability to regulate key miR-15a targets. As shown in FIG. 8A, miR-15a targets YAP1, BMI1, DCLK1 and BCL2 exhibited protein levels that were reduced upon transfection by either the unmodified miR-15a (native-miR15a) or modified miR-15a compositions, indicating that the 5-halouracil modification did not inhibit the ability of miR-15a to regulate their targets in cells.

Modified miR-15a has Increased Therapeutic Efficacy In Vitro.

In order to determine whether the modified miR-15a compositions of the present disclosure demonstrated increased potency in colon cancer cell lines compared to unmodified miR-15a, HCT-116 colon cancer cells were transfected with a negative control (non-specific oligonucleotide), unmodified miR-15a or the exemplary modified miR-15a compositions set forth in FIG. 1C.

Figure 8B:
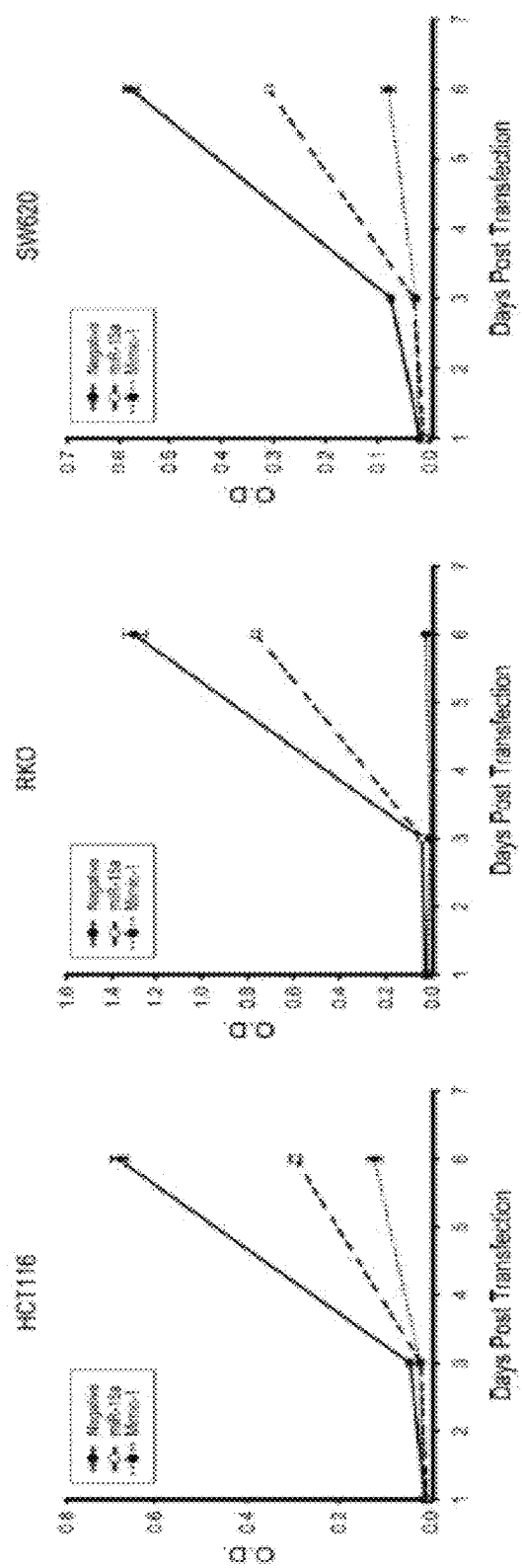

A WST-1 assay was used to assess cancer cell proliferation. As shown in FIG. 8B, six days after transfection, unmodified miR-15a had decreased cell proliferation by 53% compared to control. In the case of modified miR-15a, cell proliferation was decreased by 84%. Taken together, the experimental results show that modified miR-15a is more effective at decreasing cancer cell proliferation compared to the unmodified miR-15a.

Figure 9A:
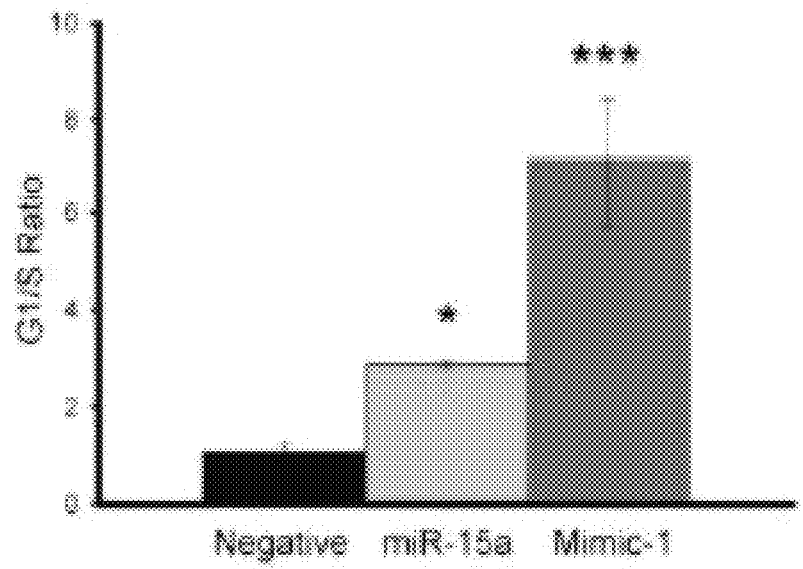
FIGS. 9A-9B. Modified microRNA nucleic acids induce cell cycle arrest at the G1/S phase in leukemia cells and colorectal cancer cells. (A) Graph showing cell cycle control for control (Negative), unmodified miR-15a (miR-15a) and an exemplary modified miR-15a nucleic acid composition as set forth in SEQ ID NO: 6 (mimic-1). Administration of modified miR-15a nucleic acid induced cell cycle arrest compared to unmodified miR-15a as shown by an increased G1/S ratio exhibited by colorectal cancer cells expressing modified miR-15a when compared to cells exogenously expressing native miR-15a and negative controls. (B) Additional exemplary modified microRNA nucleic acids (5-FU-miR-145 and 5-FU-miR-let-7) also induce cell cycle arrest at the G1/S phase compared to negative controls in blood cancer cells (i.e., REH leukemia cells) when the modified microRNAs are provided at a 50 nM concentration.

Modified miR-15a nucleic acids were also analyzed for their ability to inhibit cell cycle progression in cancer cells. FIG. 9A shows that unmodified miR-15a induced cell cycle arrest and lead to about 3-fold increase in the G1/S ratio. FIG. 9A also shows that the exemplary modified miR-15a compositions of the present disclosure were more effective in stopping cell cycle progression when compared to their native counterpart. For example, a 7-fold increase in the G1/S ratio was exhibited by cells expressing the exemplary modified miR-15a nucleic acids of the present disclosure when compared to the control. Therefore, modified miR-15a is more effective at inducing cell cycle arrest in colon cancer cells than unmodified miR-15a.

Figure 9B:
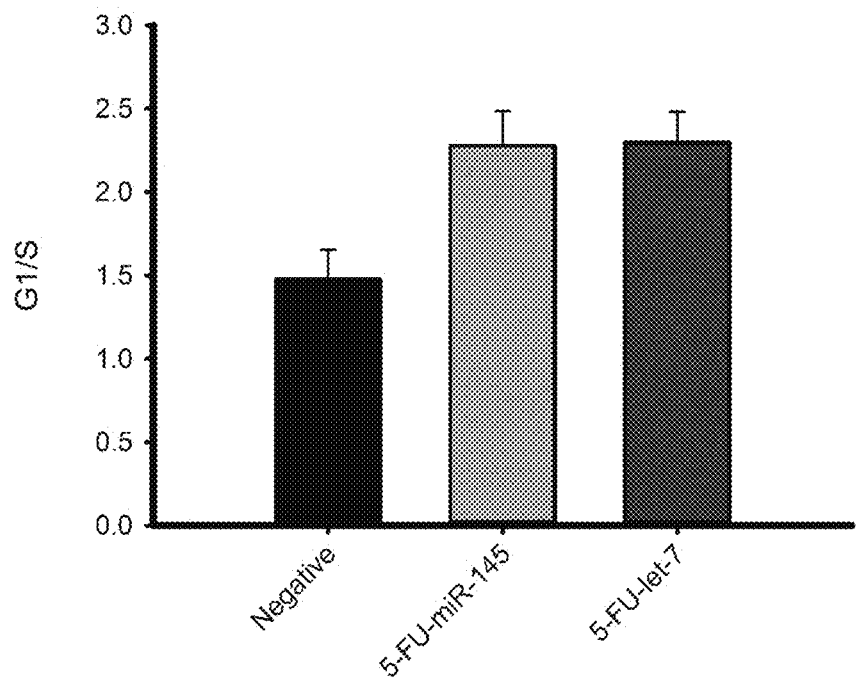

Similarly, modified miR-let-7 and modified miR-145 were more effective in stopping cell cycle progression than negative controls. See FIG. 9B. For example, a significant fold increase in the G1/S ratio was exhibited by cells expressing the exemplary modified miR-let-7 and modified miR-145 nucleic acids of the present disclosure when compared to the control.

As yet another example, modified miR-200b (5-FU-miR-200b) significantly increases the sub G1 and G1/S ratio of breast cancer cells in a population when compared to controls (i.e., native exogenous miR-200b or vehicle alone, NC). See FIG. 16C. This shows that exemplary miR-200b can also treat cancer by inhibiting cell cycle progression.

The effects of the exemplary modified miR-15a compositions on colony formation by colon cancer stem cells in Matrigel matrix were also examined. As shown in FIG. 10, while many colonies were generated by cells transfected with control miRNAs (FIG. 10, Negative), very few colonies were generated by cells transfected with unmodified miR-15a (FIG. 10, miR-15a). In contrast, in the case of cells transfected with modified miR-15a, no colonies were observed (FIG. 10, 5-FU-miR-15a). These results indicate that the exemplary modified miR-15a compositions of the present disclosure are indeed more potent inhibitors of tumorigenesis and colorectal cancer progression.

Modified miR-15a Inhibits Cancer Development and Progression In Vivo.

To further our understanding of miR-15a in colon CSCs, a mouse xenograft model was established that included colorectal cancer cells that have been either pre transfected with modified miR-15a or negative control miRNA. Eight weeks after injection, tumors were measured and harvested. A drastic reduction in tumor size for tumors established from CSCs expressing modified miR-15a mimic (>25×) (n=8), as shown in FIG. 11.

The data presented here supports the viability of a novel modification in which halouracils (e.g., 5-FU) is incorporated into a miRNA nucleic acid sequence to enhance the chemotherapeutic function of the native microRNA molecule with or without the use of other chemotherapeutic agents.

Modified microRNAs are Able to Inhibit Cancer Development in a Concentration Dependent Manner and without the Aid of a Delivery Vehicle.

As shown in FIGS. 6 and 15A-15C, the exemplary modified microRNAs tested were able to inhibit, colorectal cancer, gastric cancer, breast cancer, and lung cancer cell proliferation in a concentration dependent manner (i.e., at various concentrations 50 nM, 25 nM, 12.5 nM, 6.25 nM, and 3.125 nM). Providing further evidence that the modified microRNAs of the present disclosure can be used as an anti-cancer therapeutic for the treatment of many cancers.

Furthermore, to test whether or not the modified microRNAs of the present disclosure can be delivered directly to cells and taken up by the cancer cells without the use of transfer agents or vehicles (i.e., oligofectamine), MDA-MB-231 triple negative breast cancer cells were transfected with miR-NC (negative control), exogenous unmodified miR-200b, or 5-FU-miR-200b by using oligofectamine or without delivery vehicle. As shown in FIGS. 17A-17B, the effects of expression of the exemplary modified miRs tested on breast cancer cell proliferation were monitored by MTT assay for 6 days upon transfection or incubation. In the presence of oligofectamine, native miR-200b reduced the rate of cell proliferation of MDA-MB-231 cells in comparison to control microRNAs (miR-NC). While modified miR-200b (5-FU-miR-200b) dramatically reduced the cell growth from day 3. See FIG. 17A. Unexpectedly, modified miRs were able to block proliferation of MDA-MB-231 cells without oligofectamine treatment (without delivery vehicle) whereas control microRNAs and exogenous native microRNA (i.e. native miR-200b) had no effects on proliferation without oligofectamine, as shown in FIG. 17B.

Furthermore, with regard to the use of modified miR-200b to treat breast cancer, after administration of a modified miR-200b a reduction of fibronectin (miR-200b target gene) expression and interaction with TS was observed, when compared to both exogenous native miR-200b and negative control, as shown in FIGS. 16A and 16B. The results confirm that modified microRNAs such as modified miR-200b be delivered into cancer cells and inhibit cell proliferation by modulating target genes with or without delivery agents.

SEQUENCE LISTING

<160> NUMBER OF SEQ ID NOS: 30

<210> SEQ ID NO 1
<211> LENGTH: 21
<212> TYPE: DNA
<213> ORGANISM: Homo sapiens

<400> SEQUENCE: 1
cuuuuugcgg ucugggcuug c                                              21

<210> SEQ ID NO 2
<211> LENGTH: 22
<212> TYPE: DNA
<213> ORGANISM: Homo sapiens

<400> SEQUENCE: 2
uagcagcaca uaaugguuug ug                                             22

<210> SEQ ID NO 3
<211> LENGTH: 23
<212> TYPE: DNA
<213> ORGANISM: Artificial Sequence
<220> FEATURE:
<223> OTHER INFORMATION: modified microRNA129 with additional uracils on
      the 3' end of the nucleic acid sequence
<220> FEATURE:
<221> NAME/KEY: misc_feature
<222> LOCATION: (22)..(23)
<223> OTHER INFORMATION: uracil nucleotides

<400> SEQUENCE: 3
cuuuuugcgg ucugggcuug cuu                                            23

<210> SEQ ID NO 4
<211> LENGTH: 21
<212> TYPE: DNA
<213> ORGANISM: Artificial Sequence
<220> FEATURE:
<223> OTHER INFORMATION: an exemplary modified microRNA-129 nucleic acid
      with all uracils modified
<220> FEATURE:
<221> NAME/KEY: misc_feature
<222> LOCATION: (2)..(6)
<223> OTHER INFORMATION: halouracil nucleotides
<220> FEATURE:
<221> NAME/KEY: misc_feature
<222> LOCATION: (11)..(11)
<223> OTHER INFORMATION: halouracil nucleotides
<220> FEATURE:
<221> NAME/KEY: misc_feature
<222> LOCATION: (13)..(13)
<223> OTHER INFORMATION: halouracil nucleotides
<220> FEATURE:
<221> NAME/KEY: misc_feature
<222> LOCATION: (18)..(19)
<223> OTHER INFORMATION: halouracil nucleotides

<400> SEQUENCE: 4
cuuuuugcgg ucugggcuug c                                              21

<210> SEQ ID NO 5
<211> LENGTH: 21
<212> TYPE: DNA
<213> ORGANISM: Artificial Sequence
<220> FEATURE:
<223> OTHER INFORMATION: an exemplary modified microRNA-129 nucleic acid
      with all uracils in non-seed modified
<220> FEATURE:
<221> NAME/KEY: misc_feature
<222> LOCATION: (11)..(11)

```
<223> OTHER INFORMATION: halouracil nucleotides
<220> FEATURE:
<221> NAME/KEY: misc_feature
<222> LOCATION: (13)..(13)
<223> OTHER INFORMATION: halouracil nucleotides
<220> FEATURE:
<221> NAME/KEY: misc_feature
<222> LOCATION: (18)..(19)
<223> OTHER INFORMATION: halouracil nucleotides

<400> SEQUENCE: 5
cuuuuugcgg ucugggcuug c                                              21

<210> SEQ ID NO 6
<211> LENGTH: 22
<212> TYPE: DNA
<213> ORGANISM: Artificial Sequence
<220> FEATURE:
<223> OTHER INFORMATION: an exemplary modified microRNA-15a nucleic acid
      with all uracils modified
<220> FEATURE:
<221> NAME/KEY: misc_feature
<222> LOCATION: (1)..(1)
<223> OTHER INFORMATION: halouracil nucleotides
<220> FEATURE:
<221> NAME/KEY: misc_feature
<222> LOCATION: (11)..(11)
<223> OTHER INFORMATION: halouracil nucleotides
<220> FEATURE:
<221> NAME/KEY: misc_feature
<222> LOCATION: (14)..(14)
<223> OTHER INFORMATION: halouracil nucleotides
<220> FEATURE:
<221> NAME/KEY: misc_feature
<222> LOCATION: (17)..(19)
<223> OTHER INFORMATION: halouracil nucleotides
<220> FEATURE:
<221> NAME/KEY: misc_feature
<222> LOCATION: (21)..(21)
<223> OTHER INFORMATION: halouracil nucleotides

<400> SEQUENCE: 6
uagcagcaca uaaugguuug ug                                             22

<210> SEQ ID NO 7
<211> LENGTH: 22
<212> TYPE: DNA
<213> ORGANISM: Artificial Sequence
<220> FEATURE:
<223> OTHER INFORMATION: an exemplary modified microRNA-15a nucleic acid
      with all uracils in the non-seed portion of the nucleic acid
      sequence modified
<220> FEATURE:
<221> NAME/KEY: misc_feature
<222> LOCATION: (11)..(11)
<223> OTHER INFORMATION: halouracil nucleotides
<220> FEATURE:
<221> NAME/KEY: misc_feature
<222> LOCATION: (14)..(14)
<223> OTHER INFORMATION: halouracil nucleotides
<220> FEATURE:
<221> NAME/KEY: misc_feature
<222> LOCATION: (17)..(19)
<223> OTHER INFORMATION: halouracil nucleotides
<220> FEATURE:
<221> NAME/KEY: misc_feature
<222> LOCATION: (21)..(21)
<223> OTHER INFORMATION: halouracil nucleotides

<400> SEQUENCE: 7
uagcagcaca uaaugguuug ug                                             22

<210> SEQ ID NO 8
```

```
<211> LENGTH: 22
<212> TYPE: DNA
<213> ORGANISM: Homo sapiens

<400> SEQUENCE: 8
cagugguuuu acccuauggu ag                                              22

<210> SEQ ID NO 9
<211> LENGTH: 22
<212> TYPE: DNA
<213> ORGANISM: Artificial Sequence
<220> FEATURE:
<223> OTHER INFORMATION: an exemplary modified microRNA-140 nucleic acid
      with certain uracils modified
<220> FEATURE:
<221> NAME/KEY: misc_feature
<222> LOCATION: (4)..(4)
<223> OTHER INFORMATION: halouracil nucleotides
<220> FEATURE:
<221> NAME/KEY: misc_feature
<222> LOCATION: (15)..(15)
<223> OTHER INFORMATION: halouracil nucleotides
<220> FEATURE:
<221> NAME/KEY: misc_feature
<222> LOCATION: (20)..(20)
<223> OTHER INFORMATION: halouracil nucleotides

<400> SEQUENCE: 9
cagugguuuu acccuauggu ag                                              22

<210> SEQ ID NO 10
<211> LENGTH: 21
<212> TYPE: DNA
<213> ORGANISM: Homo sapiens

<400> SEQUENCE: 10
cugaccuaug aauugacagc c                                               21

<210> SEQ ID NO 11
<211> LENGTH: 21
<212> TYPE: DNA
<213> ORGANISM: Artificial Sequence
<220> FEATURE:
<223> OTHER INFORMATION: an exemplary modified microRNA-192 nucleic acid
      with certain uracils modified
<220> FEATURE:
<221> NAME/KEY: misc_feature
<222> LOCATION: (2)..(2)
<223> OTHER INFORMATION: halouracil nucleotides
<220> FEATURE:
<221> NAME/KEY: misc_feature
<222> LOCATION: (7)..(7)
<223> OTHER INFORMATION: halouracil nucleotides
<220> FEATURE:
<221> NAME/KEY: misc_feature
<222> LOCATION: (9)..(9)
<223> OTHER INFORMATION: halouracil nucleotides
<220> FEATURE:
<221> NAME/KEY: misc_feature
<222> LOCATION: (13)..(14)
<223> OTHER INFORMATION: halouracil nucleotides

<400> SEQUENCE: 11
cugaccuaug aauugacagc c                                               21

<210> SEQ ID NO 12
<211> LENGTH: 21
<212> TYPE: DNA
<213> ORGANISM: Homo sapiens

<400> SEQUENCE: 12
```
auccuugcua ucugggugcu a                                           21

<210> SEQ ID NO 13
<211> LENGTH: 21
<212> TYPE: DNA
<213> ORGANISM: Artificial Sequence
<220> FEATURE:
<223> OTHER INFORMATION: an exemplary modified microRNA-502 nucleic acid
      with certain uracils modified
<220> FEATURE:
<221> NAME/KEY: misc_feature
<222> LOCATION: (2)..(2)
<223> OTHER INFORMATION: halouracil nucleotides
<220> FEATURE:
<221> NAME/KEY: misc_feature
<222> LOCATION: (5)..(6)
<223> OTHER INFORMATION: halouracil nucleotides
<220> FEATURE:
<221> NAME/KEY: misc_feature
<222> LOCATION: (11)..(11)
<223> OTHER INFORMATION: halouracil nucleotides
<220> FEATURE:
<221> NAME/KEY: misc_feature
<222> LOCATION: (13)..(13)
<223> OTHER INFORMATION: halouracil nucleotides
<220> FEATURE:
<221> NAME/KEY: misc_feature
<222> LOCATION: (17)..(17)
<223> OTHER INFORMATION: halouracil nucleotides
<220> FEATURE:
<221> NAME/KEY: misc_feature
<222> LOCATION: (20)..(20)
<223> OTHER INFORMATION: halouracil nucleotides

<400> SEQUENCE: 13
auccuugcua ucugggugcu a                                           21

<210> SEQ ID NO 14
<211> LENGTH: 22
<212> TYPE: DNA
<213> ORGANISM: Homo sapiens

<400> SEQUENCE: 14
uauucaggaa gguguuacuu aa                                          22

<210> SEQ ID NO 15
<211> LENGTH: 22
<212> TYPE: DNA
<213> ORGANISM: Artificial Sequence
<220> FEATURE:
<223> OTHER INFORMATION: an exemplary modified microRNA-506 nucleic acid
      with certain uracils modified
<220> FEATURE:
<221> NAME/KEY: misc_feature
<222> LOCATION: (1)..(1)
<223> OTHER INFORMATION: halouracil nucleotides
<220> FEATURE:
<221> NAME/KEY: misc_feature
<222> LOCATION: (3)..(4)
<223> OTHER INFORMATION: halouracil nucleotides
<220> FEATURE:
<221> NAME/KEY: misc_feature
<222> LOCATION: (13)..(13)
<223> OTHER INFORMATION: halouracil nucleotides
<220> FEATURE:
<221> NAME/KEY: misc_feature
<222> LOCATION: (15)..(16)
<223> OTHER INFORMATION: halouracil nucleotides
<220> FEATURE:
<221> NAME/KEY: misc_feature
<222> LOCATION: (19)..(20)
<223> OTHER INFORMATION: halouracil nucleotides -continued

<400> SEQUENCE: 15
uauucaggaa gguguuacuu aa                                                    22

<210> SEQ ID NO 16
<211> LENGTH: 22
<212> TYPE: DNA
<213> ORGANISM: Artificial Sequence
<220> FEATURE:
<223> OTHER INFORMATION: an exemplary modified microRNA-140 nucleic acid
      with certain uracils modified
<220> FEATURE:
<221> NAME/KEY: misc_feature
<222> LOCATION: (4)..(4)
<223> OTHER INFORMATION: halouracil nucleotides
<220> FEATURE:
<221> NAME/KEY: misc_feature
<222> LOCATION: (7)..(10)
<223> OTHER INFORMATION: halouracil nucleotides
<220> FEATURE:
<221> NAME/KEY: misc_feature
<222> LOCATION: (15)..(15)
<223> OTHER INFORMATION: halouracil nucleotides
<220> FEATURE:
<221> NAME/KEY: misc_feature
<222> LOCATION: (17)..(17)
<223> OTHER INFORMATION: halouracil nucleotides
<220> FEATURE:
<221> NAME/KEY: misc_feature
<222> LOCATION: (20)..(20)
<223> OTHER INFORMATION: halouracil nucleotides

<400> SEQUENCE: 16
cagugguuuu acccuauggu ag                                                    22

<210> SEQ ID NO 17
<211> LENGTH: 22
<212> TYPE: DNA
<213> ORGANISM: Homo sapiens

<400> SEQUENCE: 17
uggcaguguc uuagcugguu gu                                                    22

<210> SEQ ID NO 18
<211> LENGTH: 22
<212> TYPE: DNA
<213> ORGANISM: Artificial Sequence
<220> FEATURE:
<223> OTHER INFORMATION: an exemplary modified microRNA-34 nucleic acid
      with modified uracils
<220> FEATURE:
<221> NAME/KEY: misc_feature
<222> LOCATION: (1)..(1)
<223> OTHER INFORMATION: halouracil nucleotides
<220> FEATURE:
<221> NAME/KEY: misc_feature
<222> LOCATION: (7)..(7)
<223> OTHER INFORMATION: halouracil nucleotides
<220> FEATURE:
<221> NAME/KEY: misc_feature
<222> LOCATION: (9)..(9)
<223> OTHER INFORMATION: halouracil nucleotides
<220> FEATURE:
<221> NAME/KEY: misc_feature
<222> LOCATION: (11)..(12)
<223> OTHER INFORMATION: halouracil nucleotides
<220> FEATURE:
<221> NAME/KEY: misc_feature
<222> LOCATION: (16)..(16)
<223> OTHER INFORMATION: halouracil nucleotides
<220> FEATURE:
<221> NAME/KEY: misc_feature
<222> LOCATION: (19)..(20)
<223> OTHER INFORMATION: halouracil nucleotides

```
<220> FEATURE:
<221> NAME/KEY: misc_feature
<222> LOCATION: (22)..(22)
<223> OTHER INFORMATION: halouracil nucleotides

<400> SEQUENCE: 18
uggcaguguc uuagcugguu gu                                              22

<210> SEQ ID NO 19
<211> LENGTH: 22
<212> TYPE: DNA
<213> ORGANISM: Homo sapiens

<400> SEQUENCE: 19
uaacacuguc ugguaacgau gu                                              22

<210> SEQ ID NO 20
<211> LENGTH: 22
<212> TYPE: DNA
<213> ORGANISM: Artificial Sequence
<220> FEATURE:
<223> OTHER INFORMATION: an exemplary modified microRNA-200a nucleic
      acid with modified uracils
<220> FEATURE:
<221> NAME/KEY: misc_feature
<222> LOCATION: (1)..(1)
<223> OTHER INFORMATION: halouracil nucleotides
<220> FEATURE:
<221> NAME/KEY: misc_feature
<222> LOCATION: (7)..(7)
<223> OTHER INFORMATION: halouracil nucleotides
<220> FEATURE:
<221> NAME/KEY: misc_feature
<222> LOCATION: (9)..(9)
<223> OTHER INFORMATION: halouracil nucleotides
<220> FEATURE:
<221> NAME/KEY: misc_feature
<222> LOCATION: (11)..(11)
<223> OTHER INFORMATION: halouracil nucleotides
<220> FEATURE:
<221> NAME/KEY: misc_feature
<222> LOCATION: (14)..(14)
<223> OTHER INFORMATION: halouracil nucleotides
<220> FEATURE:
<221> NAME/KEY: misc_feature
<222> LOCATION: (20)..(20)
<223> OTHER INFORMATION: halouracil nucleotides
<220> FEATURE:
<221> NAME/KEY: misc_feature
<222> LOCATION: (22)..(22)
<223> OTHER INFORMATION: halouracil nucleotides

<400> SEQUENCE: 20
uaacacuguc ugguaacgau gu                                              22

<210> SEQ ID NO 21
<211> LENGTH: 22
<212> TYPE: DNA
<213> ORGANISM: Homo sapiens

<400> SEQUENCE: 21
uaauacugcc ugguaaugau ga                                              22

<210> SEQ ID NO 22
<211> LENGTH: 22
<212> TYPE: DNA
<213> ORGANISM: Artificial Sequence
<220> FEATURE:
<223> OTHER INFORMATION: an exemplary modified microRNA-200b nucleic
      acid with modified uracils
<220> FEATURE:
```

```
<221> NAME/KEY: misc_feature
<222> LOCATION: (1)..(1)
<223> OTHER INFORMATION: halouracil nucleotides
<220> FEATURE:
<221> NAME/KEY: misc_feature
<222> LOCATION: (4)..(4)
<223> OTHER INFORMATION: halouracil nucleotides
<220> FEATURE:
<221> NAME/KEY: misc_feature
<222> LOCATION: (7)..(7)
<223> OTHER INFORMATION: halouracil nucleotides
<220> FEATURE:
<221> NAME/KEY: misc_feature
<222> LOCATION: (11)..(11)
<223> OTHER INFORMATION: halouracil nucleotides
<220> FEATURE:
<221> NAME/KEY: misc_feature
<222> LOCATION: (14)..(14)
<223> OTHER INFORMATION: halouracil nucleotides
<220> FEATURE:
<221> NAME/KEY: misc_feature
<222> LOCATION: (17)..(17)
<223> OTHER INFORMATION: halouracil nucleotides
<220> FEATURE:
<221> NAME/KEY: misc_feature
<222> LOCATION: (20)..(20)
<223> OTHER INFORMATION: halouracil nucleotides

<400> SEQUENCE: 22
uaauacugcc ugguaaugau ga                                              22

<210> SEQ ID NO 23
<211> LENGTH: 23
<212> TYPE: DNA
<213> ORGANISM: Homo sapiens

<400> SEQUENCE: 23
uaauacugcc ggguaaugau gga                                             23

<210> SEQ ID NO 24
<211> LENGTH: 23
<212> TYPE: DNA
<213> ORGANISM: Artificial Sequence
<220> FEATURE:
<223> OTHER INFORMATION: an exemplary modified microRNA-200c nucleic
      acid with modified uracils
<220> FEATURE:
<221> NAME/KEY: misc_feature
<222> LOCATION: (1)..(1)
<223> OTHER INFORMATION: halouracil nucleotides
<220> FEATURE:
<221> NAME/KEY: misc_feature
<222> LOCATION: (4)..(4)
<223> OTHER INFORMATION: halouracil nucleotides
<220> FEATURE:
<221> NAME/KEY: misc_feature
<222> LOCATION: (7)..(7)
<223> OTHER INFORMATION: halouracil nucleotides
<220> FEATURE:
<221> NAME/KEY: misc_feature
<222> LOCATION: (14)..(14)
<223> OTHER INFORMATION: halouracil nucleotides
<220> FEATURE:
<221> NAME/KEY: misc_feature
<222> LOCATION: (17)..(17)
<223> OTHER INFORMATION: halouracil nucleotides
<220> FEATURE:
<221> NAME/KEY: misc_feature
<222> LOCATION: (20)..(20)
<223> OTHER INFORMATION: halouracil nucleotides

<400> SEQUENCE: 24
uaauacugcc ggguaaugau gga                                             23
```

```
<210> SEQ ID NO 25
<211> LENGTH: 23
<212> TYPE: DNA
<213> ORGANISM: Homo sapiens

<400> SEQUENCE: 25
guccaguuuu cccaggaauc ccu                                              23

<210> SEQ ID NO 26
<211> LENGTH: 23
<212> TYPE: DNA
<213> ORGANISM: Artificial Sequence
<220> FEATURE:
<223> OTHER INFORMATION: an exemplary modified microRNA-145 nucleic acid
      with modified uracils
<220> FEATURE:
<221> NAME/KEY: misc_feature
<222> LOCATION: (2)..(2)
<223> OTHER INFORMATION: halouracil nucleotides
<220> FEATURE:
<221> NAME/KEY: misc_feature
<222> LOCATION: (7)..(10)
<223> OTHER INFORMATION: halouracil nucleotides
<220> FEATURE:
<221> NAME/KEY: misc_feature
<222> LOCATION: (19)..(19)
<223> OTHER INFORMATION: halouracil nucleotides
<220> FEATURE:
<221> NAME/KEY: misc_feature
<222> LOCATION: (23)..(23)
<223> OTHER INFORMATION: halouracil nucleotides

<400> SEQUENCE: 26
guccaguuuu cccaggaauc ccu                                              23

<210> SEQ ID NO 27
<211> LENGTH: 22
<212> TYPE: DNA
<213> ORGANISM: Homo sapiens

<400> SEQUENCE: 27
uguaacagca acuccaugug ga                                               22

<210> SEQ ID NO 28
<211> LENGTH: 22
<212> TYPE: DNA
<213> ORGANISM: Artificial Sequence
<220> FEATURE:
<223> OTHER INFORMATION: an exemplary modified microRNA-194 nucleic acid
      with modified uracils
<220> FEATURE:
<221> NAME/KEY: misc_feature
<222> LOCATION: (1)..(1)
<223> OTHER INFORMATION: halouracil nucleotides
<220> FEATURE:
<221> NAME/KEY: misc_feature
<222> LOCATION: (3)..(3)
<223> OTHER INFORMATION: halouracil nucleotides
<220> FEATURE:
<221> NAME/KEY: misc_feature
<222> LOCATION: (13)..(13)
<223> OTHER INFORMATION: halouracil nucleotides
<220> FEATURE:
<221> NAME/KEY: misc_feature
<222> LOCATION: (17)..(17)
<223> OTHER INFORMATION: halouracil nucleotides
<220> FEATURE:
<221> NAME/KEY: misc_feature
<222> LOCATION: (19)..(19)
<223> OTHER INFORMATION: halouracil nucleotides

<400> SEQUENCE: 28
```

```
uguaacagca acuccaugug ga                                              22

<210> SEQ ID NO 29
<211> LENGTH: 22
<212> TYPE: DNA
<213> ORGANISM: Homo sapiens

<400> SEQUENCE: 29
ugagguagua gguuguauag uu                                              22

<210> SEQ ID NO 30
<211> LENGTH: 22
<212> TYPE: DNA
<213> ORGANISM: Artificial Sequence
<220> FEATURE:
<223> OTHER INFORMATION: an exemplary modified microRNA-let-7 nucleic
      acid with modified uracils
<220> FEATURE:
<221> NAME/KEY: misc_feature
<222> LOCATION: (1)..(1)
<223> OTHER INFORMATION: halouracil nucleotides
<220> FEATURE:
<221> NAME/KEY: misc_feature
<222> LOCATION: (6)..(6)
<223> OTHER INFORMATION: halouracil nucleotides
<220> FEATURE:
<221> NAME/KEY: misc_feature
<222> LOCATION: (9)..(9)
<223> OTHER INFORMATION: halouracil nucleotides
<220> FEATURE:
<221> NAME/KEY: misc_feature
<222> LOCATION: (13)..(14)
<223> OTHER INFORMATION: halouracil nucleotides
<220> FEATURE:
<221> NAME/KEY: misc_feature
<222> LOCATION: (16)..(16)
<223> OTHER INFORMATION: halouracil nucleotides
<220> FEATURE:
<221> NAME/KEY: misc_feature
<222> LOCATION: (18)..(18)
<223> OTHER INFORMATION: halouracil nucleotides
<220> FEATURE:
<221> NAME/KEY: misc_feature
<222> LOCATION: (21)..(22)
<223> OTHER INFORMATION: halouracil nucleotides

<400> SEQUENCE: 30
ugagguagua gguuguauag uu                                              22
```

What is claimed is:

1. A double-stranded nucleic acid comprising a modified microRNA nucleotide sequence that comprises uracil nucleic acids, wherein all the uracil nucleic acids including the seed region of the modified microRNA nucleotide sequence, which are complementary to a B-cell lymphoma 2 (BCL2) nucleotide sequence, are 5-fluorouracils, to combine the potency of microRNA nucleotide sequence and 5-fluorouracils, and wherein the modified microRNA nucleotide sequence binds to the B-cell lymphoma 2 (BCL2) nucleotide sequence that is complementary to the miR-129 microRNA nucleotide sequence set forth in SEQ ID NO: 1 or the miR-15a microRNA nucleotide sequence set forth in SEQ ID NO: 2.

2. A pharmaceutical composition comprising at least one double-stranded nucleic acid of claim 1.

3. The pharmaceutical composition of claim 2, wherein said modified microRNA nucleotide sequence comprises the miR-15a nucleotide sequence.

4. The pharmaceutical composition of claim 2, wherein said modified microRNA nucleotide sequence comprises the miR-129 nucleotide sequence.

5. The double-stranded nucleic acid of claim 1, wherein the modified microRNA nucleotide sequence comprises the miR-129 nucleotide sequence.

6. The double-stranded nucleic acid of claim 1, wherein modified microRNA nucleotide sequence comprises the miR-15a nucleotide sequence.

7. The double-stranded nucleic acid of claim 6, wherein the modified microRNA nucleotide sequence is UAGCAGCACAU$^F$AAU$^F$GGU$^F$U$^F$U$^F$GU$^F$G [SEQ ID NO. 7].

* * * * *